(12) United States Patent
Mack et al.

(10) Patent No.: US 6,723,538 B2
(45) Date of Patent: Apr. 20, 2004

(54) BISPECIFIC ANTIBODY AND CHEMOKINE RECEPTOR CONSTRUCTS

(75) Inventors: Matthias Mack, Munich (DE); Detlef Schlondorff, Munich (DE); Michael Spring, Eichenau (DE)

(73) Assignee: Micromet AG, Munich (DE)

( * ) Notice: Subject to any disclaimer, the term of this patent is extended or adjusted under 35 U.S.C. 154(b) by 37 days.

(21) Appl. No.: 09/948,004

(22) Filed: Sep. 5, 2001

(65) Prior Publication Data

US 2003/0017979 A1 Jan. 23, 2003

Related U.S. Application Data

(63) Continuation-in-part of application No. PCT/EP00/02154, filed on Mar. 10, 2000.

(30) Foreign Application Priority Data

Mar. 11, 1999 (DE) .......................... 199 10 891
Sep. 8, 2000 (EP) ............................. 00119694

(51) Int. Cl.[7] .................. C07K 16/28; C12N 15/62
(52) U.S. Cl. ................ 435/69.7; 530/387.1; 530/387.3; 530/388.22; 536/23.4; 536/23.5
(58) Field of Search ............... 530/387.1, 387.3, 530/388.22; 536/23.4, 23.5; 435/69.7

(56) References Cited

FOREIGN PATENT DOCUMENTS

| WO | WO 98/08957 | 3/1998 |
|---|---|---|
| WO | WO 98/18826 | 5/1998 |
| WO | WO 99/01127 | 1/1999 |
| WO | WO 00/04926 | 2/2000 |

OTHER PUBLICATIONS

Mack, et al., "A small bispecific antibody construct expressed as a functional single–chain molecule with high tumor cell cytotoxicity," *Proc. Natl. Acad. Sci.*, vol. 92, pp. 7021–7025, Jul. 1995.

Mack, et al., "High Accumulation of Leukocytes Expressing the Chemokine Receptor CCR5 in Inflammatory Joint Effusions," *Arthritis & Rheumatism Abstract Supp. 1998 Natl. Scientific Mtg.*, vol. 41, No. 9, Sep. 1998.

*Primary Examiner*—Prema Mertz
(74) *Attorney, Agent, or Firm*—Fish & Richardson P.C.

(57) ABSTRACT

The invention is directed to chimeric polypeptides, e.g., bispecific antibodies, comprising a chemokine receptor binding domain and a T cell surface polypeptide or cell toxin binding domain, nucleic acids that encode them, and methods of making and using them. The chimeric polypeptides of the invention can include, be bound to, or attached to, a cell toxin. The invention is also directed to pharmaceutical compositions and methods for making and using them, including the treatment of immunological disorders, such as autoimmune diseases, and for the targeted elimination of cells, e.g., T lymphocytes and other cells latently infected with a primate immunodeficiency virus, such as a human immunodeficiency virus, e.g., HIV-1.

11 Claims, 25 Drawing Sheets

Fig. 19C

BISPECIFIC ANTIBODY AND CHEMOKINE RECEPTOR CONSTRUCTS

RELATED APPLICATIONS

This application is a continuation-in-part application ("CIP") and under 35 USC §120 claims priority to Patent Convention Treaty (PCT) International Application Ser. No: PCT/EP00/02154, filed Mar. 10, 2000, which claims priority to DE 199 10 891.9, filed Mar. 11, 1999; and this application is a CIP of and under 35 USC §119 claims priority to EP application no. 00 11 9694.8, filed Sep. 08, 2000. The aforementioned applications are explicitly incorporated herein by reference in their entirety and for all purposes.

TECHNICAL FIELD

This invention relates generally to cell biology, virology and medicine. In particular, the invention is directed to chimeric polypeptides, e.g., bispecific antibodies, comprising a chemokine receptor binding domain and a T cell surface polypeptide, a cell toxin, or a cell toxin binding domain, nucleic acids that encode them, and methods of making and using them. The chimeric polypeptides of the invention can include, be bound to, or attached to, a cell toxin. The invention is also directed to making and using pharmaceutical compositions, for example, for the treatment of immunological (e.g., autoimmune) disorders and for the targeted elimination of cells, e.g., T lymphocytes and other cells latently infected with a primate immunodeficiency virus, such as a human immunodeficiency virus, e.g., HIV-1. The pharmaceutical compositions and methods of the invention can be used for the treatment, prevention and/or alleviation of inflammatory joint and renal diseases, inflammatory bowel diseases, multiple sclerosis, skin diseases, diabetes or transplant rejection.

BACKGROUND

Immunological diseases/disorders, like autoimmune diseases, inflammation disorders as well as infectious diseases are not only increasing but represent substantial threats to global health. For example, in Germany, about 1% of the population suffer from the autoimmune disease rheumatoid arthritis. In addition, there is a number of other joint diseases also leading to arthritis. Currently, three groups of drugs- non-steroidal anti-rheumatics, cortisone preparations and second-line agents- and TNFα blocking agents are used for treating inflammatory joint diseases. Up to now, the therapy has focused on the local injection of cortisone preparations in combination with a systemic administration of anti-phlogistics or second-line agents.

Non-steroidal anti-rheumatics have a mild analgetic and anti-inflammatory effect, but they have many side effects when applied frequently (e.g. gastric ulcers, nephroses). In high dosages, cortisone preparations have a strong decongestant and analgetic effect, however, leading to a quick relapse after discontinuation of the therapy. Moreover, cortisone preparations cannot stop the destruction process of the joint disease. A long-term therapy with cortisone usually entails severe side effects, such as infections, Cushing's phenomenon, osteoporosis, parchment-like skin, metabolic and hormonal disorders. The local injection of cortisone also has the essential disadvantage that the activity of the migrated white blood cells is only reduced. As the infiltrating cells are not destroyed, a quick relapse occurs after discontinuation of the therapy. As mentioned above, the same applies to the systemic application. Rarely, inflammation due to the irritative effect of cortisone crystals is aggravated after injection of cortisone. The duration of effect of a cortisone injection varies tremendously and ranges from primary ineffectiveness to a duration of effect of several weeks.

In rheumatology, second-line agents are used to achieve a long-term suppression of the inflammation and a reduction in cortisone preparations. Due to the considerable toxicity (e.g., allergies, infections, malignant diseases, renal insufficiency, blood pressure crises, pulmonary diseases) it is necessary for medical specialists to attend closely to the patients. After beginning treatment, no therapeutic effect may be apparent for the first three months. Currently, there are 4 or 5 of such second-line agents at disposal, which are used individually at first or are combined if the therapy is not effective. Mostly, there is hardly anything known about the mode of action of second-line agents. It is not yet entirely clear whether the application of second-line agents can diminish the destruction of the joint.

In recent years, a new group of substances has been introduced into the treatment of rheumatoid arthritis, which is based on the blocking of cell signal substances, particularly TNFα, by means of monoclonal antibodies or soluble receptor constructs.

In addition, there are patients that do not respond to currently available therapies. In other cases, the conventional therapy has to be stopped due to intolerable side effects.

A similar situation exists for many other inflammatory and autoimmune diseases like inflammatory renal diseases, inflammatory bowel diseases, multiple sclerosis and transplant rejection, where current treatments have many limitations. For example, agents used in inflammatory and autoimmune diseases include anti-inflammatory and immunosuppressive agents like azathioprine, cyclophosphamide, glucocorticoids like prednisone; immunosuppressants like cyclosporin A, Tacrolimus (FK506), Sirolimus (Rapamycin); and protein drugs like calcineurin, beta-interferon, anti-TNF alpha monoclonal antibodies (remicade). These agents show general immunomodulating effects and therefore efficacy and side effects profiles can pose severe limitations for the treatment options; see, e.g., Harrison's Principles of Internal Medicine, eds. Fauci et al., 14th edition, McGraw-Hill publisher.

Inflammatory bowel diseases, such as Crohn's disease, ulcerative colitis, are treated with the anti-inflammatory agents sulfazsalazine (Azulfidine) and glucocorticoids, like prednisone and, in selected cases, with TNF-α blocking agents. In ulcerative colitis immunosuppressive therapy with drugs such as azathioprine is well established, in severely ill patients the potent immunosuppressive agent cyclosporine is used (see, e.g., Harrison's Principles of Internal Medicine, eds. Fauci et al., 14th edition, McGraw-Hill publisher). In many cases no sufficient reduction of disease activity is achieved with current drugs, such that even surgical intervention is sometimes necessary.

Inflammatory renal diseases (nephritis) are treated with e.g. glucocorticoids, alkylating agents and/or plasmapheresis. Additional diseases with similar treatment options include systemic lupus erythematosus (SLE), Sjogren's syndrome, polymyositis, dermatomyositis, mixed connective tissue disease, anti-phospholipid-antibody syndrome.

For some of these diseases, few therapeutic options have been available up to now. All these diseases share an inflammatory component. However, the inflammatory component cannot be sufficiently suppressed by the currently available drugs. For some drugs, e.g. alkylating agents a maximal lifetime dose per patient cannot be exceeded.

Transplant rejection is treated using immunosuppressive agents including azathioprine, mycophenolate mofetil, glucocorticoids, cyclosporine, Tacrolimus (FK506), Sirolimus (Rapamycin). A combination of steroids and a low dose of mouse monoclonal antibody OKT3 binding to CD3 on T-cells is used to anergize and deplete T-cells. Therapy is continued using immunosuppressants like cyclosporine. Mouse anti-human antibodies (MAHAs) have common side effects and limit the use of OKT3 (Fauci et al., supra, pp. 2374–2381).

Approaches to treat multiple sclerosis include treatments which effect the overall immune system like anti-inflammatory agents including azathioprine, cyclophosphamide, prednisone, corticosteroids, cyclosporin A, calcineurin, Rapamycin, beta-interferon (see, e.g., Fauci et al., supra, pp. 2415–2419; Wang (2000) J. Immunol. 165:548–557). In addition, a number of non-specific treatments are administered that may improve the quality of life including physical therapy and psycho-pharmacological agents. None of the treatment options mentioned above has a curative effect. Even the most promising compound, β-interferon, leads only to a slower disease progression, while exhibiting significant side effects.

Furthermore, human immunodeficiency virus-type 1 (HIV-1), the most common cause of AIDS, has infected more than 50 million individuals (including those who have died), and the rate of new infections is estimated at nearly 6 million per year (AIDS Epidemic Update: December 1999 (UNAIDS, Geneva, 1999), www.unaids.org). Equally disturbing are the uncertainties of the epidemic to come. Although sub-Saharan Africa remains the global epicenter, rates of infection have increased in recent times in the former Soviet Union and parts of south and southeast Asia, including India and China, where literally hundreds of millions of individuals are potentially at risk. In the United States, new waves of infection have been recognized in women, minorities, and younger generations of gay men. Combination antiretroviral therapy has afforded many people clinical relief, but the costs and toxicities of treatment are substantial, and HIV-1 infection remains a fatal disease. Moreover, the vast majority of infected people worldwide do not have access to these agents. Thus, although the demographics (and, in some instances, the natural history) of AIDS have changed, the epidemic is far from over; instead, it is evolving, expanding, and posing ever greater challenges.

Human immunodeficiency virus (HIV) cannot enter human cells unless it first binds to two key molecules on the cell surface, CD4 and a co-receptor. The co-receptor that is initially recognized is chemokine receptor 5 (CCR5). Later in the life cycle of the virus, another chemokine receptor, CXCR4, becomes the co-receptor for HIV-1; see, e.g., D'Souza, Nature Med. 2:1293 (1996); Premack, Nature Med. 2:1174; Fauci, Nature 384:529 (1996).

The HIV-1 strains that cause most transmissions of viruses by sexual contact are called M-tropic viruses. These HIV-1 strains, also known as NSI primary viruses, can replicate in primary CD4+ T-cells and macrophages and use the chemokine receptor 5 (CCR5), and, less often, CCR3, as their entry co-receptor. The T-tropic viruses, sometimes called SI primary, can also replicate in primary CD4+ T-cells, but can, in addition, infect established CD4+ T-cell lines in vitro, which they do via the chemokine receptor CXCR4 (fusin). Many of these T-tropic strains can use CCR5 in addition to CXCR4, and some can enter macrophages via CCR5, at least under certain in vitro conditions; see, e.g., D'Souza, Nature Med. 2, 1293 (1996); Premack, Nature Med. 2, 1174; Fauci, Nature 384, 529 (1996).

Whether other co-receptors contribute to HIV-1 pathogenesis is unresolved, but the existence of another co-receptor for some T-tropic strains can be inferred from in vitro studies. Because M-tropic HIV-1 strains are implicated in about 90% of sexual transmissions of HIV, CCR5 is the predominant co-receptor for the virus in patients; transmission (or systemic establishment) of CXCR4-using (T-tropic) strains is rare (D'Souza, Nature Med. 2, 1293 (1996); Premack, Nature Med. 2, 1174; Fauci, Nature 384, 529 (1996), Paxton, Nature Med. 2, 412 (1996); Liu, Cell 86, 367 (1996); Samson, Nature 382, 722 (1996); Dean, Science 273, 1856 (1996); Huang, Nature Med. 2, 1240 (1996)). However, once SI viruses evolve in vivo (or if they are transmitted), they are especially virulent and cause faster disease progression; see, e.g., D'Souza, Nature Med. 2, 1293 (1996); Premack, Nature Med. 2, 1174; Fauci, Nature 384, 529 (1996), Schuitemaker, J. Virol. 66, 1354 (1992); Connor, J. Virol. 67, 1772 (1993); Richman, J. Infect. Dis. 169, 968 (1994); R. I. Connor (1997) J. Exp. Med. 185:621; Trkola, Nature 384, 184 (1996).

The numbers and identity of co-receptor molecules on target cells, and the ability of HIV-1 strains to likely enter cells via the different co-receptors, seem to be critical determinants of disease progression. These factors are major influences on both host- and virus-dependent aspects of HIV-1 infection. For example, a homozygous defect (delta 32) in CCR5 correlates strongly with resistance to HIV-1 infection in vivo and in vitro. Individuals who are heterozygous for a defective CCR5 allele are not protected against infection and have only a modestly slowed disease progression (Paxton, Nature Med. 2, 412 (1996); Liu, Cell 86, 367 (1996); Samson, Nature 382, 722 (1996); Dean, Science 273, 1856 (1996); Huang (1996) Nature Med. 2:1240).

However, other factors can influence the level of CCR5 expression on activated CD4+ T-cells and thereby affect the efficiency of HIV-1 infection in vitro (Trkola, Nature 384, 184 (1996); Bleul, Proc. Natl. Acad. Sci. U.S.A. 94, 1925 (1997)). For reasons that are not yet clear, the amount of CCR5 expression on the cell surface (as measured by MIP-1 binding) varies by 20-fold on CD4+ T-cells from individuals with two wild-type CCR5 alleles (Trkola, Nature 384, 184 (1996)). Staining with a CCR5-specific monoclonal antibody indicates a similar large variability (Wu, J. Exp. Med. 186:1373–81 (1997)). Such variation may far outweigh any effect of one defective allele for CCR5. The causes of this variation should be the subject of intensive studies, as they point to controllable factors that could increase resistance to disease.

Most primary, clinical isolates of primate immunodeficiency viruses use the chemokine receptor CCR5 for entry (see, e.g., Feng, Science 272, 872 (1996); Choe, Cell 85, 1135 (1996); Deng, Nature 381, 661 (1996); Dragic et al., Nature 381, p. 667; Doranz, Cell 85, 1149 (1996); Alkhatib, Science 272, 1955 (1996)). For most HIV-1 isolates that are transmitted and that predominate during the early years of infection, CCR5 is an obligate co-receptor, and rare individuals that are genetically deficient in CCR5 expression are relatively resistant to HIV-1 infection (see, e.g., Connor, J. Exp. Med. 185, 621 (1997); Zhang, Nature 383, 768 (1996); Björndal, J. Virol. 71, 7478 (1997); Dean, Science 273, 1856 (1996); Liu, Cell 86, 367 (1996); Paxton, Nature Med. 2, 412 (1996); Samson, Nature 382, 722 (1996)). HIV-1 isolates arising later in the course of infection often use other chemokine receptors, frequently CXCR4, in addition to CCR5. Studies of chimeric envelope glycoproteins demonstrated that the third variable (V3) loop of gp 120 is a major determinant of which chemokine receptor is used as a viral entry co-receptor (see, e.g., Cocchi, Nature Med. 2, 1244 (1996); Bieniasz, EMBO J. 16, 2599 (1997); Speck, J. Virol. 71, 7136 (1997)). V3-deleted versions of gp120 do not bind CCR5, even though CD4 binding occurs at wild-type levels. Antibodies to the V3 loop interfere with gp120-CCR5 binding (see, e.g., Trkola, Nature 384, 184 (1996); Wu, Nature 384, 179 (1996); Lapham, Science 274, 602 (1996); Bandres, J. Virol. 72, 2500 (1998); Hill, Science 71, 6296 (1997)). These results support an involvement of the V3 loop in chemokine receptor binding.

Latency of HIV is established very early in the course of an infection, when M-tropic strains predominate. M-tropic strains depend on the presence of CCR5 on the target cell for infection. The importance of CCR5 as an essential co-receptor for M-tropic HIV-1 is emphasized by the fact that individuals lacking CCR5 due to a homozygous 32 base pair deletion (delta32) are highly resistant to HIV-1 infection. In contrast to other markers like CD4 or CD45RO, CCR5 is only present on a subset of lymphocytes and other cells that are prone to HIV-1 infection (Rottmann (1997) Am. J. Pathol. 151:1341–1351; Naif (1998) J. Virol. 72:830–836; Lee (1999) Proc. Natl Acad. Sci. USA 96:5315–5220).

Several approaches have been postulated to eliminate latent infected cells. One strategy is to drive the latently infected cells to virus production and subsequent cell death. In this context, one approach is IL-2 (or TNF-alpha or IL-6) administration in the presence of HAART until the viral reservoir is exhausted (Chun (1998) J. Exp. Med. 188, 83–91; Chun (1999) Nat. Med. 5, 651–655; Stellbrink (1999) Abstracts of the 6th Conference on Retroviruses and Opportunistic Infections (Foundation for Retrovirology and Human Health, Alexandria, Va.), abstr. 356. p. 135; Imamichi (1999) Abstracts of the 6th Conference on Retroviruses and Opportunistic Infections (Foundation for Retrovirology and Human Health, Alexandria, Va.), abstr. 358, p. 135). These cells are believed to die after activation. Whether the entire pool of latent infected cells can be exhausted is questionable.

Another strategy tried was to specifically kill latently infected cells based on gp-120 expression on the cell surface. Immunotoxins recognizing gp-120 have been proposed but failed for two reasons. The one construct tested in humans was a protein consisting of soluble CD4 linked to *Pseudomonas aeroginosa* exotoxin A (PE). The clinical results were disappointing due to dose-limiting hepatotoxicity without showing signs of efficacy and the program was terminated (Ashorn (1990) Proc. Natl Acad. Sci 87, 8889–8893; Berger (1998) Proc. Natl Acad. Sci. 95, 11511–11513). The second reason for failure was that latent infected cells do not express viral surface glycoproteins, e.g. gp-120 and gp-41. Thus, approaches targeting gp-120 or gp-41 for the elimination of latently infected cells cannot work.

Other approaches to eliminate latent infected cells are based on eliminating the entire CD4+ T-cell compartment (Berger (1998) Proc. Natl Acad. Sci. 95, 11511–11513), or the CD25-positive compartment (Bell (1993) Proc. Natl Acad. Sci. 90, 1411–1415), or the CD45RO memory cell compartment (McCoig (1999) Proc. Natl. Acad. Sci 96, 11482–11485). However these markers do not adequately include all potentially infected cells. Such cells also include, besides CD4-positive cells, macrophages, and non-hematopoietic cells.

In Wu, et al., WO 98/18826, an antibody directed against the mammalian (e.g. human) chemokine receptor 5 (CCR5) is described and said antibody is proposed in a method of inhibiting the interaction of cell bearing CCR5 with a potential ligand, like HIV. It is proposed that said method inhibits an HIV infection. Furthermore, treatment options for inflammatory diseases, autoimmune diseases and graft rejection are proposed. Yet, all these treatment options are based on the assumption that specific antibodies, like the immunoglobulin molecules themselves, or functional portions thereof, interfere with receptor-ligand interactions. However, whether these antibodies are capable of depleting the relevant cells is questionable. Furthermore, WO 98/18826 merely envisages the prevention of an interaction of HIV and the CCR5 receptor and thereby preventing an HIV infection.

Leukocytes, in particular T-cells, are believed to be the key regulators of the immune response to infective agents and are critical components for the initiation and maintenance of inflammatory processes, like inflammatory bowel disease inflammatory renal diseases, inflammatory joint disease, autoimmune disorders, like multiple sclerosis and arthritis, skin diseases, like psoriatic lesions, diabetes and in transplant rejection.

Thus, there exists a need for novel means and methods which can lead to the suppression of activated leukocytes involved in immunological pathologies, like autoimmune diseases, inflammation process and/or viral infections of immune cells. The present invention fulfills this and other needs.

SUMMARY

The invention provides a chimeric polypeptide, e.g., a bispecific antibody, comprising a first polypeptide domain comprising at least one moiety that specifically binds to a chemokine receptor; and, a second polypeptide domain comprising at least one moiety that specifically binds to a T cell surface polypeptide or a cell toxin, or, a cell toxin. In one aspect of the invention, the chemokine receptor is a chemokine receptor 5 (CCR5), such as a human chemokine receptor 5 (CCR5). In one aspect, the moiety that specifically binds to the chemokine receptor 5 (CCR5) can comprise a RANTES ("regulated on activation normal T cell expressed and secreted") polypeptide, or a fragment thereof capable of binding to a CCR5 receptor. Alternatively, the moiety that specifically binds to the CCR5 chemokine receptor can comprise a MIP-1α, or a fragment thereof capable of binding to a CCR5 receptor. In another aspect, the moiety that specifically binds to the CCR5 chemokine receptor can comprise a MIP-1β, a MCP-2, or a MCP-3 or a fragment thereof, capable of binding to the CCR5 receptor.

In one aspect of the chimeric composition of the invention, the moiety that specifically binds to the chemokine receptor comprises an IP-10 (CXCL-10) (see, e.g., Agostini (2001) Am. J. Pathol. 158:1703–1711; Flier (1999) J. Invest. Dermatol. 113:574–578), or a Mig (CXCL9) (see, e.g., Farber (1997) J. Leukoc. Biol. 61:246–257), or an I-TAC (CXCL11) chemokine ligand (see, e.g., Gasperini (1999) J. Immunol. 162:4928–4937), or a fragment thereof (see Table IV), capable of binding to the CXCR3 chemokine receptor.

In alternative aspects, the chemokine receptor is CXCR4 (see, e.g., Vila-Coro (1999) FASEB J. 13:1699–1710), CXCR5 (see, e.g., Legler (1998) J. Exp. Med. 187:655–660), CXCR6 (see, e.g., Luttichau (2001) Eur. J. Immunol. 31:1217–1220), CCR1 (see, e.g., Hesselgesser (1998) J. Biol. Chem. 273:15687–15692), CCR2 (see, e.g., Monteclaro (1997) J. Biol. Chem. 272:23186–23190), CCR3 (see, e.g., Dairaghi (1997) J. Biol. Chem. 272:28206–28209), CCR4 (see, e.g., Imai (1997) J. Biol. Chem. 272:15036–15042), CCR5 (see, e.g., Ganju (2000) J. Biol. Chem. 275:17263–17268), CCR6 (see, e.g., Baba (1997) J. Biol. Chem. 272:14893–14898), CCR7 (see, e.g., Kim (1999) Cell Immunol. 193:226–235), CCR8 (see, e.g., Roos (1997) J. Biol. Chem. 272:17251–17254), CCR9 (see, e.g., Norment (2000) J. Immunol. 164:639–648), CCR10 (see, e.g., Bonini (1997) DNA Cell Biol. 16:1249–1256), XCR1 (GPR5) (see, e.g., Shan (2000) Biochem. Biophys. Res. Commun. 268:938–941), or CX3CR1 (see, e.g., Combadiere (1998) Biochem. Biophys. Res. Commun. 253:728–732); see Table IV, which includes the corresponding chemokine ligands. The T cell surface polypeptide can comprise a CD3 polypeptide.

In one aspect, the chimeric composition of the invention comprises a cell toxin, or a fragment or domain thereof that remains toxic to cells. The cell toxin can comprise a Pseudomonas exotoxin, or toxic fragment thereof. The Pseudomonas exotoxin can comprise a PE38 exotoxin, a PE40 exotoxin or a PE37 exotoxin. Alternatively, the cell toxin can comprise a diptheria toxin. The cell toxin can be non-covalently or covalently, directly or indirectly, attached or associated with the chimeric composition. In one aspect, the toxin is cross-linked to the chimeric polypeptide. Alternatively, the toxin can comprise a recombinant fusion protein, as all or a portion of the chimeric polypeptide can comprise a recombinant protein, e.g., it can be a fusion protein. In one aspect, the moiety that specifically binds to a chemokine receptor comprises an antigen binding domain derived from an antibody that specifically binds to the chemokine receptor. The moiety that specifically binds to a T cell surface polypeptide can comprise an antigen binding domain derived from an antibody that specifically binds to the T cell surface polypeptide. The moiety that specifically binds to a cell toxin can comprise an antigen binding domain derived from an antibody that specifically binds to the cell toxin.

The invention also provides a recombinant fusion protein comprising a first polypeptide domain comprising at least one moiety that specifically binds to a chemokine receptor; and, a second polypeptide domain comprising at least one moiety that specifically binds to a T cell surface polypeptide or a cell toxin, or, a cell toxin.

The invention also provides a bispecific antibody comprising a first antigen binding domain that specifically binds to a chemokine receptor; and, a second antigen binding domain that specifically binds to a T cell surface polypeptide, a cell toxin, or a third antigen binding domain that specifically binds to or is linked to a T cell surface polypeptide or a cell toxin. The bispecific antibody is not limited to two binding domains. The T cell surface polypeptide can comprise a CD3 antigen.

In one aspect of the bispecific antibody of the invention, the bispecific antibody is a single chain antibody construct. The single chain antibody construct can comprise a $V_L$ and a $V_H$ domain capable of specifically binding the chemokine receptor and a $V_H$ and a $V_L$ domain capable of specifically binding a T cell surface polypeptide. In one aspect, the antigen binding domain that specifically binds to a chemokine receptor can comprise a murine anti-human CCR5 antibody MC-1. In one aspect, the $V_L$ and $V_H$ domains are arranged in the order $V_L$(MC-1)-$V_H$(MC-1)-$V_H$(CD3)-$V_L$(CD3). The $V_L$(MC-1) domain can comprise an amino acid sequence as set forth in SEQ ID NO:12. The $V_H$(MC-1) domain can comprise an amino acid sequence as set forth in SEQ ID NO:16. The $V_H$(CD3) domain can comprise an amino acid sequence as set forth in SEQ ID NO:26. The $V_L$(CD3) domain can comprise an amino acid sequence as set forth in SEQ ID NO:28. The amino acid sequence of the bispecific antibody can be encoded by a nucleic acid as set forth in SEQ ID NO: 17, or comprising an amino acid sequence as set forth in SEQ ID NO: 18.

In one aspect of the bispecific antibody, the second antigen binding domain specifically binds to a cell toxin, or, the second antigen binding domain specifically binds to another domain (e.g., an antibody) that can specifically bind a toxin (or a cell surface protein). Alternatively, the antibody is covalently bound (directly or indirectly) to a cell toxin. The antibody can be bound to a second antibody that binds to a CD3 antigen or a cell toxin.

The invention provides a nucleic acid encoding a chimeric polypeptide (e.g., a bispecific antibody) comprising a first polypeptide domain comprising at least one moiety that specifically binds to a chemokine receptor; and, a second polypeptide domain comprising at least one moiety that specifically binds to a T cell surface polypeptide or a cell toxin, or, a cell toxin.

The invention provides a vector comprising a nucleic acid encoding a chimeric polypeptide (e.g., a bispecific antibody) comprising a first polypeptide domain comprising at least one moiety that specifically binds to a chemokine receptor; and, a second polypeptide domain comprising at least one moiety that specifically binds to a T cell surface polypeptide or a cell toxin, or, a cell toxin.

The invention provides a transformed cell comprising a nucleic acid encoding a chimeric polypeptide (e.g., a bispecific antibody) comprising a first polypeptide domain comprising at least one moiety that specifically binds to a chemokine receptor; and, a second polypeptide domain comprising at least one moiety that specifically binds to a T cell surface polypeptide or a cell toxin, or, a cell toxin.

The invention provides a pharmaceutical composition comprising a chimeric polypeptide of the invention, a nucleic acid of the invention, or a vector of the invention, or a transformed cell of the invention; and, a pharmaceutically acceptable excipient.

The invention provides a kit comprising a chimeric polypeptide (e.g., a bispecific antibody) of the invention, a nucleic acid of the invention, a vector of the invention, a transformed cell of the invention, or a pharmaceutical composition of the invention. The kit can further comprise pharmaceutically acceptable excipients. The kits can further comprise instructions on the specific uses of the pharmaceuticals of the invention, as set forth herein. The kit can further comprise ancillary or other drugs, e.g., where the kit is intended to be used to treat HIV-1 (e.g., AIDS), drugs employed in HAART also can be included in the kit.

The invention provides a use of a chimeric polypeptide (e.g., a bispecific antibody) or a nucleic acid of the invention (e.g., a vector of the invention) to prepare a pharmaceutical composition for the elimination of cells that are latently infected with a primate (e.g., human) immunodeficiency virus, e.g., HIV-1, or a lentivirus.

The invention provides a use of a chimeric polypeptide (e.g., a bispecific antibody) or a nucleic acid of the invention (e.g., a vector of the invention) to prepare a pharmaceutical composition for the treatment of an immunological disorder, such as an autoimmune disease, an allergic disease, a skin disease, an inflammatory disease, diabetes, graft versus host disease and transplant rejections. In alternative aspects, the autoimmune disease is, e.g., multiple sclerosis, type I diabetes and rheumatoid arthritis. In alternative aspects, the skin disease is a skin inflammation, an atopic dermatitis and psoriasis. In alternative aspects, the inflammatory disease is an inflammatory joint disease, such as arthritis (e.g., chronic arthritis), an inflammatory renal disease and an inflammatory bowel disease.

The invention provides a method for eliminating a cell infected with a primate immunodeficiency virus comprising administering a composition comprising a chimeric polypeptide (e.g., a bispecific antibody) or a nucleic acid of the invention (e.g., a vector of the invention), in amounts sufficient to kill the cell. In one aspect, the primate immunodeficiency virus is a human immunodeficiency virus, such as HIV-1. The cell can be infected (e.g., latently infected) with a pathogen, e.g., a virus, such as a primate immunodeficiency virus.

The invention provides a method for the treatment of a primate immunodeficiency virus comprising the following steps: (a) providing a pharmaceutical composition comprising a chimeric polypeptide (e.g., a bispecific antibody) or a nucleic acid of the invention (e.g., a vector of the invention), (b) administering the pharmaceutical composition in amounts sufficient to treat the primate immunodeficiency virus. The treatment can further comprise administration of other drugs, e.g., those employed in HAART, or other treatments.

The invention provides a method for the treatment of an inflammatory renal disease comprising the following steps: (a) providing a pharmaceutical composition comprising a chimeric polypeptide (e.g., a bispecific antibody) or a nucleic acid of the invention (e.g., a vector of the invention), (b) administering the pharmaceutical composition in amounts sufficient to treat the inflammatory renal disease.

The invention provides a method for the treatment of an allergic reaction comprising the following steps: (a) providing a pharmaceutical composition comprising a chimeric polypeptide (e.g., a bispecific antibody) or a nucleic acid of the invention (e.g., a vector of the invention), (b) administering the pharmaceutical composition in amounts sufficient to treat the allergic reaction.

The invention provides a method for the treatment of an inflammatory bowel disease comprising the following steps: (a) providing a pharmaceutical composition comprising a chimeric polypeptide (e.g., a bispecific antibody) or a nucleic acid of the invention (e.g., a vector of the invention), (b) administering the pharmaceutical composition in amounts sufficient to treat the inflammatory bowel disease.

The invention provides a method for the treatment of multiple sclerosis comprising the following steps: (a) providing a pharmaceutical composition comprising a chimeric polypeptide (e.g., a bispecific antibody) or a nucleic acid of the invention (e.g., a vector of the invention), (b) administering the pharmaceutical composition in amounts sufficient to treat the multiple sclerosis.

The invention provides a method for the treatment of a skin disease comprising the following steps: (a) providing a pharmaceutical composition comprising a chimeric polypeptide (e.g., a bispecific antibody) or a nucleic acid of the invention (e.g., a vector of the invention), (b) administering the pharmaceutical composition in amounts sufficient to treat the skin disease.

The invention provides a method for the treatment of diabetes comprising the following steps: (a) providing a pharmaceutical composition comprising a chimeric polypeptide (e.g., a bispecific antibody) or a nucleic acid of the invention (e.g., a vector of the invention), (b) administering the pharmaceutical composition in amounts sufficient to treat the diabetes.

The invention provides a method for the treatment of a transplant rejection comprising the following steps: (a) providing a pharmaceutical composition comprising a chimeric polypeptide (e.g., a bispecific antibody) or a nucleic acid of the invention (e.g., a vector of the invention), (b) administering the pharmaceutical composition in amounts sufficient to treat the transplant rejection.

The invention provides a method for the treatment of inflammatory joint disease comprising the following steps: (a) providing a pharmaceutical composition comprising a chimeric polypeptide (e.g., a bispecific antibody) or a nucleic acid of the invention (e.g., a vector of the invention), (b) administering the pharmaceutical composition in amounts sufficient to treat the inflammatory joint disease. The inflammatory joint disease can comprise arthritis, such as rheumatoid arthritis.

The invention provides a method of making a chimeric composition that can bind to a chemokine receptor and a cell toxin comprising the following steps: (a) providing a first polypeptide comprising at least one moiety that specifically binds to a chemokine receptor and at least one moiety that specifically binds to a second polypeptide comprising an antigen binding domain, wherein the antigen comprises a cell toxin, and a compound comprising a cell toxin; (b) contacting the first and second polypeptide with the compound in vivo or in vitro under conditions wherein the first polypeptide specifically binds to the second polypeptide, and the second polypeptide specifically binds to the compound, thereby making the chimeric composition.

The invention provides a method of making a chimeric composition that can bind to a chemokine receptor and a T cell surface antigen comprising the following steps: (a) providing a first polypeptide comprising at least one moiety that specifically binds to a chemokine receptor and at least one moiety that specifically binds to a second polypeptide comprising an antigen binding domain, wherein the antigen comprises a T cell surface antigen binding domain; (b) contacting the first polypeptide with the second polypeptide in vivo or in vitro under conditions wherein the first polypeptide specifically binds to the second polypeptide, thereby making a chimeric composition. The T cell surface antigen can comprise a CD3 antigen.

The chimeric composition can further comprise a cell toxin covalently bound to the chimeric composition. The cell toxin can be a truncated sequence, e.g., a domain, that remains toxic to the cell, e.g., a Pseudomonas exotoxin A (PE38).

The present invention relates to the use of an antibody and/or a chemokine construct which binds to a chemokine receptor. These compositions are used to eliminate cells that are latently infected with a primate immunodeficiency virus; accordingly, the invention is also directed to pharmaceuticals comprising these compositions. The invention is also directed to use of these compositions for the preparation pharmaceutical compositions. The pharmaceutical compositions and methods using these pharmaceuticals for the treatment, prevention and/or alleviation of inflammatory renal diseases, inflammatory joint diseases, inflammatory bowel diseases, multiple sclerosis, skin diseases, diabetes or transplant rejection.

Furthermore, the invention relates to antibody constructs and/or chemokine constructs, in particular, to constructs wherein said antibody construct comprises a binding site for a chemokine receptor 5 (CCR5) and a binding site for CD3, wherein said chemokine construct comprises RANTES ("regulated on activation normal T cell expressed and secreted") and a toxin. The invention also describes polynucleotides encoding said antibody or chemokine constructs, and vectors and hosts comprising said nucleic acid molecules. Additionally, the present invention relates to compositions comprising said antibody constructs, chemokine constructs, polynucleotides, vectors and/or hosts. The composition can be a pharmaceutical composition. Described is also the use of antibody constructs, the chemokine constructs, the polynucleotides, the hosts and/or the vectors for the preparation of a pharmaceutical composition for treating, preventing and/or alleviating an immunological disorder or for eliminating latently infected cells, wherein said cells are infected with a primate immunodeficiency virus, like HIV-1.

The present invention also relates to a method for treating, preventing and/or alleviating an immunological disorder or for the elimination cells that are latently infected with a primate immunodeficiency virus, such as HIV-1. Furthermore, the invention provides for a kit comprising the compounds of the invention. The kit can also include instructions on the use of pharmaceuticals in the kit.

Several documents are cited throughout the text of this specification. Each of the documents cited herein (including any manufacturers specifications, instructions, etc.) and all publications, patents, patent applications, GenBank sequences and ATCC deposits, cited herein are hereby expressly incorporated by reference for all purposes.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
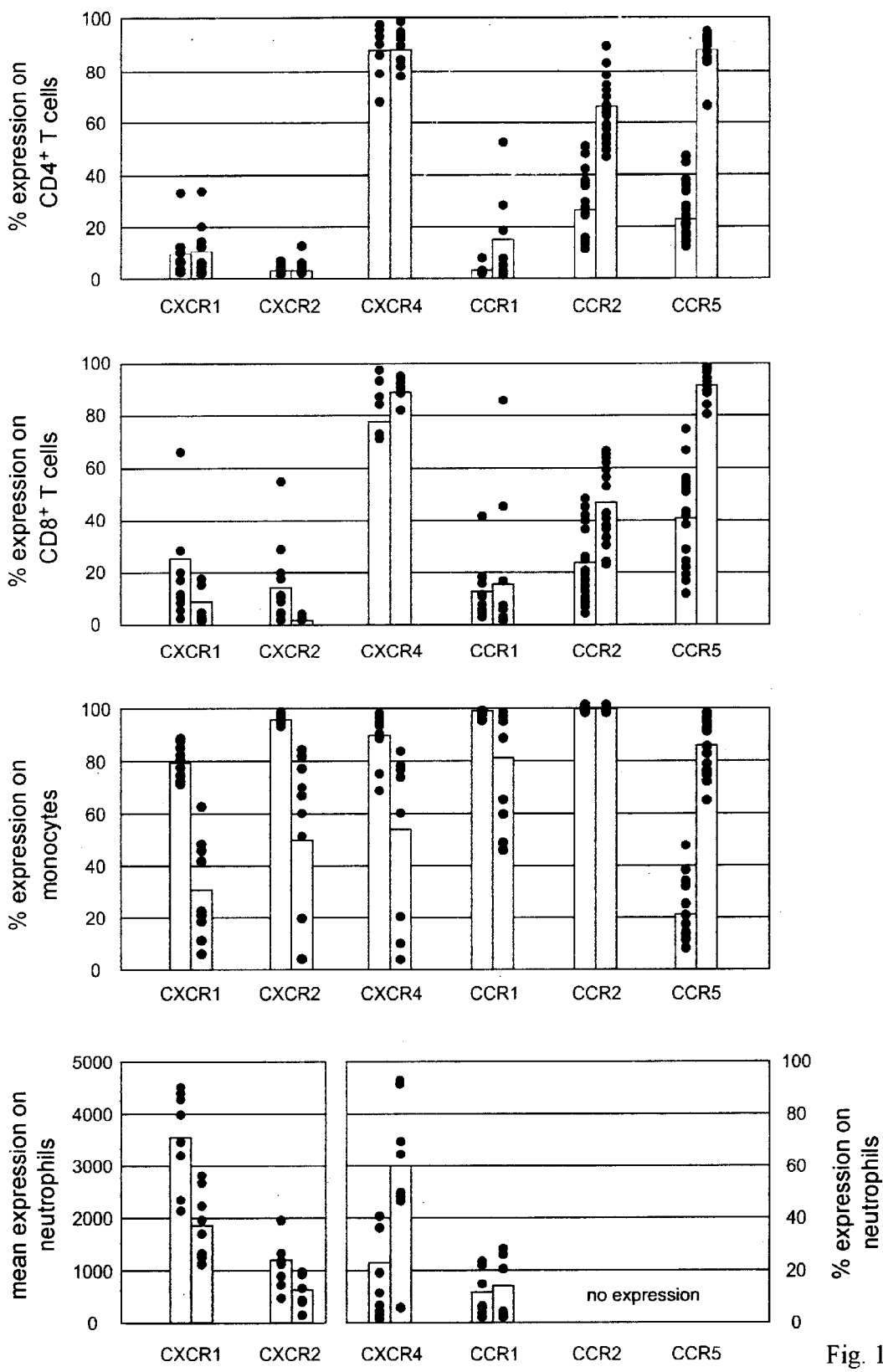
FIG. 1 panels summarize data showing the expression of various chemokine receptors (indicated on the x-axis) on T cells (first and second panel), monocytes (third panel) and neutrophils (fourth panel) in the peripheral blood (white columns) and the synovial fluid (gray columns) of patients with arthritis other than gout; as described in detail in the Examples, below. Each dot represents one patient and mean values are given as bars. Expression of CXCR1 and CXCR2 on neutrophils is given as fluorescence intensity on the y-axis, while in all other cases the percentage of receptor positive cells is depicted.

The invention provides chimeric polypeptides (e.g., chimeric antibodies and chemokines constructs), nucleic acids and vectors encoding them, and pharmaceuticals comprising these compositions for the prevention and treatment of infections, e.g., infectious diseases, including viral infections, such as HIV-1, and autoimmune diseases. The binding of the antibody and/or chemokine constructs of the present invention to a chemokine receptor results in the depletion and/or destruction of a target cell. These target cells include infected cells, such as cells latently infected with primate (e.g., human) immunodeficiency viruses, including HIV-1. Target cells can also include lymphocytes responsible for autoimmune disease.

As discussed herein, it was surprisingly be shown that highly specific antibodies directed against a chemokine receptor were not able to destroy, lyse and/or deplete cells which express said chemokine receptor. However, the antibody constructs or chemokine constructs as described and disclosed in the present invention specifically interacted with chemokines-receptor positive cells and were able to deplete these cells. While the invention is not limited by any particular mechanism of action, this depletion/destruction may, e.g., be achieved by the attraction of specific effector cells, such as monocytes, macrophages, lymphocytes (e.g., T-cells, such as cytotoxic T-cells) or dendritic cells. Even if monoclonal antibodies had been shown to be successful in the destruction/depletion of malignant cells (see, e.g., Maloney (1999), Sem. Oncol. 26, 76–78), they appear to be ineffective against certain subtypes of leukocytes (comprising lymphocytes, polynuclear leukocytes and monocytes), especially CCR5$^+$ monocytes, T-cells and dendritic cells as documented in the examples, below.

In accordance with the present invention, the term "antibody and/or chemokine construct" not only comprises the molecules and multifunctional constructs and compounds as described herein, but also comprises functional fragments thereof. Functional fragments of the constructs are meant to be fragments which are capable of binding to/interacting with a desired molecule on a target cell, e.g., a chemokine receptor on a target cell, thus providing means for depleting, lysing and/or destroying the target cell.

Specific chemokine receptors that are targeted by the compositions of the invention, in accordance with the present invention comprise, but are not limited to, CXCR3, CXCR4, CXCR5, CXCR6, CCR1, CCR2, CCR3, CCR4, CCR5, CCR6, CCR7, CCR8, CCR9, XCR1, CCR10 and CX3CR1. Chemokines and/or chemokine ligands binding to the chemokine receptors are well known in the art; examples of receptors and corresponding ligands are shown, inter alia, in Table 4. Furthermore, chemokines and their corresponding receptors (targeted by the compositions of the invention), are disclosed in, e.g., U.S. Pat. Nos. 6,174,995; 6,172,061; 6,166,015; Murphy (2000) Pharm. Reviews 52:145–176. The moiety that specifically binds to a chemokine receptor can be a polypeptide or any other molecule, such as a synthetic chemical, that specifically binds to a chemokines receptor.

The present invention also relates to the use of a chimeric polypeptide, e.g., an antibody and/or chemokine construct, which binds to a chemokine receptor and depletes the cells expressing the receptor for the treatment, prevention and/or alleviation of inflammatory renal diseases, inflammatory joint diseases, inflammatory bowel diseases, multiple sclerosis, skin diseases, allergic reactions diabetes or transplant rejection. Skin diseases comprise, inter alia, psoriatic disorders, atopic dermatitis or chronically inflamed skin. CCR6 expression is upregulated in PBMCs derived from patients with psoriasis. In addition, CCR6 ligand, CCL20, (equivalent to MIP3alpha) and CCR6 are upregulated in psoriatic skin. Furthermore, CCL20 expressing keratinocytes colocalize with skin infiltrating T-cells (Homey (2000) J. Immunol. 164, 6621–6632).

CCR10 (known previously as orphan G-protein-coupled receptor GPR2) is expressed by melanocytes, dermal fibroblasts, dermal endothelial cells, T-cells and skin-derived Langerhans cells but not keratinocytes. CCR10 ligand (CCL27; CTACK, see, e.g., Pan (2000) J. Immunol. 165:2943–2949) has a skin associated expression pattern (Homey (2000) J. Immunol. 164, 3465–3470; Charbonnier (1999) J. Exp. Med 190, 1755–1768). Another CCR10 ligand, mucosa-associated epithelial chemokine (MEC), is a novel chemokine whose mRNA is most abundant in salivary gland, with strong expression in other mucosal sites, including colon, trachea, and mammary gland (see, e.g., Pan (2000) supra). Another CCR10 ligand is CCL28, see, e.g., Wang (2000) J. Biol. Chem. 275:22313–22323.

CCR4 and its ligand (TARC, MDC) are upregulated in chronically inflamed skin. Moreover CCR4 is a homing receptor for T-cells entering the skin. CCR4+ T-cells are only a small subpopulation of all T cells and therefore depletion of CCR4+ T-cells is indicated for various inflammatory skin diseases (Campbell (1999) Nature 400, 776–780).

CCR3 and exotoxin expression is enhanced in atopic dermatitis and may contribute to the initiation and maintenance of inflammation (Yawalkar (1999) J. Invest. Dermatol. 113, 43–48). CCR3 is expressed in epidermis of inflammatory skin lesions such as atopic dermatitis (see, e.g., Wakugawa (2001) J. Dermatol. Sci. 25:229–235). CCR3 is known to be a ligand for chemokines such as RANTES, eotaxin and monocyte-chemotactic protein-3 (MCP-3). The compositions of the invention are also used for the preparation of pharmaceutical compositions to treat or prevent infections, inflammatory and other conditions.

Virtually all T-cells in rheumatoid arthritis, synovial fluid and in various inflamed tissues such as ulcerative colitis, chronic vaginitis and sarcoidosis express CXCR3 (see, e.g., Agostini (1998) J. Immunol. 161:6413–6420), whereas fewer T-cells within normal lymph nodes are CXCR3 positive. Thus, chimeric polypeptides of the invention targeting this CXCR3 chemokine receptor are used in the treatment or prevention of these conditions.

For multiple sclerosis, it was shown that CCR5 and CXCR3 are predominantly expressed on T-cells infiltrating demyelinating brain lesions, as well as in the peripheral blood of affected patients. The corresponding ligands MIP-1α and IP-10 were also detectable in the plaques (Balashov (1999) Proc. Natl. Acad. Sci. 96, 6873–6878). Elimination of the T-cells would block the T-cell arm of this autoimmune disease. Thus, chimeric polypeptides of the invention targeting CCR5 or CXCR3 chemokine receptors are used in the treatment or prevention of these conditions.

Diabetes type I is considered to be a T-cell mediated autoimmune disease. The expression of CCR5 receptor in the pancreas was associated with the progression of type I diabetes in relevant animal models (Cameron (2000) J. Immunol. 165, 1102–1110). In particular, the CCR5 expression was associated with the development of insulinitis and spontaneous type I diabetes. Specific chemokines are associated with T-cell migration in diabetes type I relevant animal model: RANTES, MCP-1, MCP-3, MCP-5, IP10. These chemokines lead to a Th1 immune response (Bradley (1999) J. Immunol. 162:2511–2520). Thus, chimeric polypeptides of the invention targeting receptors for RANTES, MCP-1, MCP-3, MCP-5, IP10 are used in the treatment or prevention of these conditions.

The above mentioned inflammatory bowel disease may comprise Morbus Crohn and colitis ulcerosa. CCR9 is expressed on T-cells homing to the intestine and may be implied in Morbus Crohn and colitis ulcerosa. All intestinal lamina propria and intraepithelial lymphocytes express CCR9 (Zabel (1999) J. Exp. Med. 190, 1241–1256). Thus, chimeric polypeptides of the invention targeting CCR9 receptors are used in the treatment or prevention of these conditions.

Additionally, the antibody-and/or chemokine construct as described in context of the present invention is also useful for avoiding complications during and/or after transplants, i.e. to avoid transplant rejections and graft versus host disease. CCR7 is expressed on naïve T-cells and dendritic cells and mediates cell migration to lymphatic organs. Elimination of CCR7+ cells would therefore prevent an immune response to novel antigens, e.g., following transplantation. Such a treatment would not be generally immune suppressing but selective for novel antigens and limited for the duration of the administration of drugs of the invention depleting CCR7+ cells (Forster (1999) Cell 99, 23–33). CXCR5 is expressed on naïve B cells in the peripheral blood and tonsils and memory T-cells. Elimination of CXCR5+ B-cells would prevent the establishment of a humoral response. Furthermore, elimination of memory T-cells would reduce the cellular component of the immune response (Murphy (2000) Pharmacological Reviews 52:145–176).

In order to provide pharmaceutical compositions for the treatment of allergies and/or allergic reactions, the antibody-and/or chemokine constructs as described herein may be employed. It was shown that CCR3 which binds exotoxin and RANTES, is expressed on eosinophils, Th2 cells, mast cells, basophils, which are involved in allergic reactions (Romangnani (1999) Am. J. Pathol. 155, 1195–1204). Thus, chimeric polypeptides of the invention targeting CCR3 receptors are used in the treatment or prevention of allergies and/or allergic reactions.

As far as the above mentioned renal or kidney diseases are concerned, it has been shown that CCR5 positive T-cells may play a role in interstitial processes leading to fibrosis. CCR5 positive cells have been identified in the interstitial infiltrate of various glomerular and interstitial diseases, as well as transplant rejection. Said disease comprises acute and chronic nephritis, IgA nephropathy, and others (Segerer (1999), Kidney Int. 56, 52–64). Thus, chimeric polypeptides of the invention targeting CCR5 receptors are used in the treatment or prevention renal or kidney diseases.

In one embodiment of the present invention, the invention provides for the use of an antibody and/or chemokine construct which binds to a chemokine receptor for the preparation of a pharmaceutical composition as described hereinabove, wherein said chemokine receptor is the chemokine receptor 5 (CCR5). The CCR5 can be human CCR5.

The chemokine receptor CCR5 is a member of a large family of G protein coupled seven transmembrane domain receptors that binds the proinflammatory chemokines RANTES, MIP1-α, MIP1-β and MCP-2. Chemokines act in concert with adhesion molecules to induce the extravasation of leukocytes and to direct their migration to sites of tissue injury. The human RANTES polypeptide, and variations thereof, is described, e.g., in U.S. Pat. Nos. 5,965,697; 6,168,784.

The CCR5 is expressed on a minority of T-cells and monocytes and is further the major co-receptor for M-trophic HIV-1 strains that predominate early in the course of an HIV-infection. The pharmaceutical composition of the invention is particularly useful in the depletion of CCR5$^+$ leukocytes and in the elimination of cells latently infected with HIV-1 (as demonstrated in by data discussed in Examples, below). Depletion of CCR5$^+$ cells by the compositions and methods of the invention will reduce the number of cells latently infected with HIV; thus, the pharmaceuticals and methods of the invention are particularly useful in combination with active anti-viral, preferably anti-retroviral therapy.

Regarding the expression of CCR5 in different tissues and in different diseases, immunochemical analysis of the expression of the beta-chemokine receptors in post-mortem CNS tissue from patients with multiple sclerosis revealed that in chronic active multiple sclerosis (MS) lesions expression of CCR2, CCR3 and CCR5 was associated with foamy macrophages and activated microglia while low levels of these chemokine receptors were expressed by microglial cells in control CNS tissue. CCR2 and CCR5 were also present on large numbers of infiltrating lymphocytes and in 5/14 cases of MS CCR3 and CCR5 were also expressed on astrocytes. The elevated expression of CCR2, CCR3 and CCR5 in the CNS in MS suggests these beta-chemokine receptors and their ligands play a role in the pathogenesis of MS, see, e.g., Simpson (2000) Neuroimmunol. 108:192–200. Accordingly, the compositions and methods of the invention can be used to ameliorate MS.

High expression of CCR3 and CCR5 was also observed in T cells and B cells of lymph nodes derived from patients with Hodgkin's disease. While CCR3 was equally distributed in CD4+ and CD8+ cells, CCR5 was mainly associated with CD4+ cells. These data suggest that chemokines are involved in the formation of the non-neoplastic leukocytic infiltrates in Hodgkin disease; see, e.g., Buri (2001) Blood 97:1543–1548. Accordingly, the compositions and methods of the invention can be used to ameliorate Hodgkin's disease.

Periodontal disease is a peripheral infection involving species of gram-negative organisms. In patients with moderate to advanced periodontal disease CCR5 chemokine receptor expressing cells were found in the inflammatory infiltrates. see, e.g., Gamonal (2001) J. Periodontal. Res. 36:194–203; Taubman (2001) Crit. Rev. Oral. Biol. Med. 12:125–35. Accordingly, the compositions and methods of the invention can be used to ameliorate moderate to advanced periodontal disease.

In a model of transient immune complex glomerulonephritis (IC-GN), CCR1, CCR2, and CCR5 were expressed early and were already down-regulated at the peak of proteinuria and leukocyte infiltration. Expression of CCR5 was located to the glomerulus by in situ hybridization and quantitative reverse transcription-PCR of isolated glomeruli (Anders, J. Am. Soc. Nephrol., 2001, 12, 919–31). In kidneys of 38 patients with several renal diseases, CCR1- and CCR5-positive macrophages and T cells were detected in both glomeruli and interstitium as shown by immunohistochemistry. Renal CCR5-positive cells were dramatically decreased during convalescence induced by glucocorticoids (Furuichi, Am. J. Nephrol., 2000, 20, 291–9). Accordingly, the compositions and methods of the invention can be used to ameliorate glomerulonephritis.

In another aspect of the invention, the antibody construct is a bispecific antibody that binds to a desired chemokine receptor, such as a CCR5 or CCR3, as a first antigen and a CD3 antigen of an effector cell as a second antigen. The CD3 antigen can be on the surface of a T-cell, such as a cytotoxic T-cell. CD3 is an antigen that is expressed on T cells and may be part of a multimolecular (T-) cell receptor complex.

Bispecific antibodies may be constructed by hybrid-hybridoma techniques, by covalently linking specific antibodies or by other approaches, like the diabody approach (Kipriyanow, Int. J. Cancer 77 (1998), 763–773). In one aspect of the invention, the bispecific antibody is a single chain antibody construct.

As is well known, Fv, the minimum antibody fragment which contains a complete antigen recognition and binding site, consists of a dimer of one heavy and one light chain variable domain ($V_H$ and $V_L$) in non-covalent association. In this configuration that corresponds to the one found in native antibodies the three complementarity determining regions (CDRs) of each variable domain interact to define an antigen binding site on the surface of the $V_H$-$V_L$ dimer. Collectively, the six CDRs confer antigen binding specificity to the antibody. Frameworks (FRs) flanking the CDRs have a tertiary structure that is essentially conserved in native immunoglobulins of species as diverse as human and mouse. These FRs serve to hold the CDRs in their appropriate orientation. The constant domains are not required for binding function, but may aid in stabilizing $V_H$-$V_L$ interaction. Even a single variable domain (or half of an Fv comprising only three CDRs specific for an antigen) has the ability to recognize and bind antigen, although usually at a lower affinity than an entire binding site (Painter, Biochem. 11 (1972), 1327–1337). Hence, said domain of the binding site of the antibody construct as defined and described in the present invention can be a pair of $V_H$-$V_L$, $V_H$-$V_H$ or $V_L$-$V_L$ domains of different immunoglobulins. The order of $V_H$ and $V_L$ domains within the polypeptide chain is not decisive for the present invention, the order of domains given hereinabove may be reversed usually without any loss of function. It is important, however, that the $V_H$ and $V_L$ domains are arranged so that the antigen binding site can properly fold.

Different parts of the antibodies/immunoglobulins can be joined by means of conventional methods or constructed as a contiguous protein by means of recombinant DNA techniques, e.g. in such a way that a nucleic acid molecule coding for a chimeric or humanized antibody chain is expressed in order to construct a contiguous protein (e.g., see Mack (1995) Proc. Natl. Acad. Sci. USA 92:7021–7025).

In one aspect, a single-chain antibody with the following Fv fragments is used: sc-Fv fragment of a monoclonal antibody against the chemokine receptor, such as, e.g., CCR5, and an sc-Fv fragment of a monoclonal antibody against a T cell surface polypeptide, e.g., a CD3. In this case, both the Fv fragment directed against the chemokine receptor and the Fv fragment against CD3 may be located in N-terminal position. The Fv fragment against CCR5 may be in N-terminal position. The order of the VL and VH antibody domains can be variable in both constructs, in one aspect, the order of the Fv fragment against CCR5 is VL-VH and the one of the Fv fragment against CD3 is VH-VL. The linkers between the variable domains as well between the two Fv fragments may consist of peptide linkers, preferably of a hydrophilic flexible glycine- and serine-containing linker of 1 to 25 amino acids. An additional epitope tag, e.g., a histidine chain of, e.g., 6×His, in C- or N-terminal position, can be used to simplify purification and detection.

Compared to conventional bispecific antibodies, bispecific single-chain antibodies have the advantage that they consist of only one protein chain and thus their composition is exactly defined. They have a low molecular weight of normally <60 kD and can be produced easily and on a large scale in suitable cell lines, e.g. in CHO cells, using recombinant techniques. The most essential advantage, however, is that they have no constant antibody domains and thus only activate T-lymphocytes to lysis when these are bound to their target cells, i.e. to the chemokine-receptor expressing cells. Therefore, single-chain antibodies are often superior to conventional bispecific antibodies as their clinical use entails fewer or less severe side effects.

Therefore, in one aspect, the single chain antibody construct comprises $V_L$ and $V_H$ domains of a antibody specific for a chemokine receptor, such as a human CCR5, and $V_H$ and $V_L$ domains of an antibody specific for a T cell surface polypeptide, e.g., a CD3 antigen.

One exemplary antibody specific for the human CCR5 is the murine anti-human CCR5 antibody MC-1, described, inter alia, in Mack (1998) J. Exp. Med. 187:1215–1224, and in the appended examples. MC-1 is the "parental" antibody that detects CCR5 whose binding fragment was employed in the chimeric construct of invention. As discussed in detail in Example 11, below, MC-1 was shown to bind specifically to the first part of the second extracellular loop of human CCR5 and did not cross-react with CCR5 derived from rhesus macaques.

Other α-CCR5 antibodies, like MC-5 (as characterized in the appended examples and disclosed in Segerer (1999), loc. cit.) also may be employed in the context of this invention. The antibody specific for the T cell surface polypeptide, such as a CD3 antigen, may be selected from the group consisting of antibodies recognizing the gamma, delta, epsilon, zeta chains, such as the CD3 zeta chain (Jakobs (1997) Cancer Immunol Immunother. 44, 257–264; Mezzanzanica (1991) Cancer Res 51, 5716–5721). Examples of anti-epsilon chain antibodies are OKT3 (WO 91/09968, Kung (1979) Science 206:347–349; Van Wauwe, J. Immunol. 124, 2708–2713 (1980); Transy, Eur. J. Immunol. 19, 947–950 (1989); Woodle, J. Immunol. 148, 2756–2763 (1992); Ada, Human. Antibod. Hybridomas, 41–47 (1994)) and TR66 (Traunecker (1991) EMBO J. 10, 3655–3659). Examples of monoclonal antibodies against the CD3 zeta chain are H2D9, TIA2 (both Becton Dickinson), G3 (Serotec Ltd.).

In one embodiment of the use of the present invention, the $V_L$ and $V_H$ domains of the single chain antibody as described above are arranged in the order $V_L$(MC-1)-$V_H$(MC-1)-$V_H$(MC-1)-$V_H$(CD3)-$V_L$(CD3). In alternative aspects, the $V_L$(MC-1) comprises the acid sequence as depicted in SEQ ID NO:12, wherein said $V_H$(MC-1) comprises the amino acid sequence as depicted in SEQ ID NO: 16, wherein said $V_H$(CD3) comprises the amino acid sequence as depicted in SEQ ID NO:26 and/or wherein said $V_L$(CD3) comprises in SEQ ID NO:28. Specific CDR parts of the MC-1 antibody are shown in SEQ ID NO:29 to SEQ ID NO:34, wherein SEQ ID NO: 29 shows the CDR1 of $V_L$ MC-1, SEQ ID NO: 30 shows the CDR2 of $V_L$ MC-1, SEQ ID NO: 31 shows the CDR3 of $V_L$-MC-1, SEQ ID NO: 32 shows the CDR1 of $V_H$ MC-1, SEQ ID NO: 33 shows the CDR2 of $V_H$ MC-1 and SEQ ID NO:34 depicts the CDR 3 of $V_H$ MC-1. Said bispecific antibody may, inter alia, comprise an amino acid sequence encoded by the nucleic acid sequence as depicted in SEQ ID NO: 17 or comprises the amino acid sequence as depicted in SEQ ID NO: 18.

In another embodiment of the invention, the antibody construct is a bispecific antibody that binds to a chemokine receptor as a first antigen and a toxin as a second antigen. The antibody may be covalently bound to the toxin, and the antibody-toxin construct may be constructed by chemical coupling, producing a fusion protein or a mosaic protein from the antibody and from a modified or unmodified prokaryotic or eukaryotic toxin. Furthermore, the antibody may be joined to a toxin via multimerization domains.

In a further embodiment of the present invention, the antibody construct can, via a multimerization domain, be bound in vitro and/or in vivo to a second antibody construct which binds to a CD3 antigen and/or a toxin. The multimerization may, inter alia, be obtained via hetero(di) merization. For example, the hetero(di)merization region of constant immunoglobulin domains may be employed. Other multi- and/or heterodimerization domains are known in the art and are based on leucine zippers, α- and β-chains of T-cell receptors or MHC-class II molecules. Furthermore, jun- and fos-based domains may be employed (de Kuif (1996) J. Biol. Chem. 271:7630–7634; Kostelny (1992), J. Immunol. 148, 1547–1553). Additional examples of multimerization domains are p53- and MNT-domains as described, e.g., in Sakamoto (1994) Proc. Natl. Acad. Sci. USA 91, 8974–8978; Lee (1994) Nat. Struct. Biol. 1, 877–890; Jeffrey (1995) Science 267, 1498–5102 or Nooren (1999) Nat. Struct. Biol. 6, 755–759.

In another embodiment of the invention, the chimeric polypeptide of the invention, e.g., a chemokine construct, is a fusion construct of a modified or an unmodified chemokine with a modified or an unmodified toxin. The construct may be bound in vitro and/or in vivo, e.g., by a multimerization domain, to an antibody construct which binds to a T cell surface polypeptide, e.g., a CD3 antigen, and/or to a toxin. Suitable multimerization domains have been described in the art and are described herein. The chemokine-toxin constructs may, inter alia, result from chemical coupling, may be recombinantly produced (as shown in the appended examples), or may be produced as a fusion protein from a chemokine and a modified or unmodified prokaryotic or eukaryotic toxin. In one aspect, the moiety that specifically binds to a chemokine receptor, e.g., a chemokine or fragment thereof, binds to a human chemokine receptor, e.g., CCR5, and comprises, inter alia, RANTES, MIP-1α, MIP-1β, MCP-2, MCP-3 or (a) fragment(s) thereof which are capable of binding to the desired chemokine receptor.

The compositions of the invention can comprise any cytotoxic agent. For example, in one aspect, the toxin may be a polypeptide toxin, e.g., a Pseudomonas exotoxin, like PE38, PE40 or PE37, or a truncated version thereof, or a ribosome inactivating protein gelonin (e.g., Boyle (1996) J. Immunol. 18:221–230), and the like. The compositions of the invention can be conjugated to any cytotoxic pharmaceuticals, e.g., radiolabeled with a cytotoxic agents, such as, e.g., $^{131}$I (e.g., Shen (1997) Cancer 80(12 Suppl):2553–2557), copper-67 (e.g., Deshpande (1988) J. Nucl. Med. 29:217–225).

Furthermore, and in accordance with the present invention, the chemokine construct may comprise the chemokine covalently bound to an antibody construct which binds to an antibody construct capable of binding to a T cell surface polypeptide, e.g., a CD3 antigen, and/or which is a covalently bound to a toxin.

In one embodiment of the present invention, the antibody and/or chemokine construct is a heterominibody construct comprising at least an antibody and/or a chemokine which binds to a chemokine receptor, such as the CCR5 or CCR3 receptor, e.g., a human CCR5 or CCR3 receptor. The heterominibody construct may comprise at least one toxin; in one aspect the heterominibody construct binds to the chemokine receptor as defined hereinabove and/or to a T cell surface polypeptide, e.g., a CD3 antigen, of an effector cell. Exemplary chemokines are mentioned hereinabove; exemplary toxins are described hereinabove, which may be modified or unmodified. Chemokines are well known in the art and described, inter alia, in Murphy (1999), loc. cit. Therefore, the chemokine can be selected from the group consisting of RANTES, MIP-1β, MIP-1α, MCP-2, and MCP-3 or a functional fragment thereof. In one aspect, the chemokine is RANTES. Functional fragments of chemokines are fragments that are capable of binding to or interacting with the chemokine receptor, e.g., a human CCR5. Heterominibodies are known in the art and their production is described, inter alia, in WO 00/06605. The heterominibody may be a multifunctional compound comprising at least one antibody and/or chemokine binding to or interacting with a chemokine receptor, such as human CCR5 or CCR3, may (additionally) comprise a toxin as defined herein and/or a binding site for a T cell surface polypeptide, e.g., the CD3 antigen.

In one embodiment, the antibody- or chemokine construct is a fusion (poly)peptide or a mosaic (poly)peptide. The fusion (poly)peptide may comprise merely the domains of the constructs as described herein, as well as (a) functional fragment(s) thereof. However, it is also envisaged that said fusion (poly)peptide comprises further domains and/or functional stretches. Therefore, said fusion (poly)peptide can comprise at least one further domain, this domain being linked by covalent or non-covalent bonds. The linkage as well as the construction of such constructs, can be based on genetic fusion according to the methods known in the art (e.g., Sambrook et al., loc. cit., Ausubel, "Current Protocols in Molecular Biology", Green Publishing Associates and Wiley Interscience, N.Y. (1989)) or can be performed by, e.g., chemical cross-linking as described in, e.g., WO 94/04686. The additional domain present in the construct may be linked by a flexible linker, such as a (poly)peptide linker, wherein the (poly)peptide linker can comprises plural, hydrophilic, peptide-bonded amino acids of a length sufficient to span the distance between the C-terminal end of said further domain and the N-terminal end of the peptide, (poly)peptide or antibody or vice versa. The linker may, inter alia, be a Glycine, a Serine and/or a Glycine/Serine linker. Additional linkers comprise oligomerization domains. Oligomerization domains can facilitate the combination of two or several autoantigens or fragments thereof in one functional molecule. Non-limiting examples of oligomerization domains comprise leucine zippers (like jun-fos, GCN4, E/EBP; Kostelny, J. Immunol. 148 (1992), 1547–1553; Zeng, Proc. Natl. Acad. Sci. USA 94 (1997), 3673–3678, Williams, Genes Dev. 5 (1991), 1553–1563; Suter, "Phage Display of Peptides and Proteins", Chapter 11, (1996), Academic Press), antibody-derived oligomerization domains, like constant domains CH1 and CL (Mueller, FEBS Letters 422 (1998), 259–264) and/or tetramerization domains like GCN4-LI (Zerangue, Proc. Natl. Acad. Sci. USA 97 (2000), 3591–3595).

Furthermore, the antibody- or chemokine construct to be used in the present invention, as described herein, may comprise at least one further domain, inter alia, domains which provide for purification means, like, e.g. histidine stretches. The further domain(s) may be linked by covalent or non-covalent bonds.

The linkage can be based on genetic fusion according to the methods known in the art and described herein or can be performed by, e.g., chemical cross-linking as described in, e.g., WO 94/04686. The additional domain present in the construct as described and disclosed in the invention may be linked by a flexible linker, such as a polypeptide linker to one of the binding site domains; the polypeptide linker can comprise plural, hydrophilic or peptide-bonded amino acids of a length sufficient to span the distance between the C-terminal end of one of said domains and the N-terminal end of the other of said domains when said polypeptide assumes a conformation suitable for binding when disposed in aqueous solution. The polypeptide linker can be a polypeptide linker as described. The polypeptide of the invention may further comprise a cleavable linker or cleavage site for proteinases, such as enterokinase It is also envisaged that said constructs disclosed for uses, compositions and methods of the present invention comprises (a) further domain(s) which may function as immunomodulators. The immunomodulators comprise, but are not limited to cytokines, lymphokines, T cell co-stimulatory ligands, etc.

Adequate activation resulting in priming of naive T-cells is critical to primary immunoresponses and depends on two signals derived from professional APCs (antigen-presenting cells) like dendritic cells. The first signal is antigen-specific and normally mediated by stimulation of the clonotypic T-cell antigen receptor (TCR) that is induced by processed antigen presented in the context of MHC class-I or MHC class-II molecules. However, this primary stimulus is insufficient to induce priming responses of naive T-cells, and the second signal is required which is provided by an interaction of specific T-cell surface molecules binding to co-stimulatory ligand molecules on antigen presenting cells (APCs), further supporting the proliferation of primed T-cells. The term "T-cell co-stimulatory ligand" therefore denotes in the light of the present invention molecules, which are able to support priming of naive T-cells in combination with the primary stimulus and include, but are not limited to, members of the B7 family of proteins, including B7-1 (CD80) and 137-2 (CD86).

The antibody- and/or chemokine construct described herein may comprise further receptor or ligand function(s), and may comprise immuno-modulating effector molecule or a fragment thereof. An immuno-modulating effector molecule positively and/or negatively influences the humoral and/or cellular immune system, particularly its cellular and/or non-cellular components, its functions, and/or its interactions with other physiological systems. The immuno-modulating effector molecule may be selected from the group consisting of cytokines, chemokines, macrophage migration inhibitory factor (MIF; as described, inter alia, in Bernhagen (1998), Mol Med 76(3–4); 151–61 or Metz (1997), Adv Immunol 66, 197–223), T-cell receptors and soluble MHC molecules. Such immuno-modulating effector molecules are well known in the art and are described, inter alia, in Paul, "Fundamental immunology", Raven Press, New York (1989). In particular, known cytokines and chemokines are described in Meager, "The Molecular Biology of Cytokines" (1998), John Wiley & Sons, Ltd., Chichester, West Sussex, England; (Bacon (1998). Cytokine Growth Factor Rev 9(2):167–73; Oppenheim (1997). Clin Cancer Res 12, 2682–6; Taub, (1994) Ther. Immunol. 1(4), 229–46 or Michiel, (1992). Semin Cancer Biol 3(1), 3–15).

Antibody and/or chemokine constructs of the present invention can comprise (an) additional functional domain(s) and may, inter alia, be multifunctional compounds, like heterominibodies, as described herein.

The constructs of the present invention may comprise domains originating from one species, e.g., from mammals, such as human. However, chimeric and/or humanized constructs are also envisaged and within the scope of the present invention.

In one embodiment, the construct of the invention comprises a cross-linked (poly)peptide construct. As described herein, the cross-linking may be based on methods known in the art, which comprise recombinant as well as biochemical methods.

In embodiment of the present invention, the chimeric polypeptide, e.g., an antibody construct or a chemokine construct, comprises at least one toxin. The toxin may be Pseudomonas exotoxin A, diphtheria toxin and similar toxins. It is envisaged that truncated toxins are employed, like the PE38 or the PE40 of Pseudomonas toxin described in the appended examples. The toxin may be bound to said antibody or chemokine by means as described herein. It is also envisaged that said toxin is bound to the chimeric polypeptide (e.g., antibody/chemokines) by means of a short peptide linker. The linker can comprise a flexible and hydrophilic amino acid sequence, e.g., of glycines and serines. The linker can has a length of 1 to about 20 amino acids, or more.

Several fusion proteins with a truncated version of Pseudomonas exotoxin A have been designed. Most of them have been used to target and destroy malignant cells. This toxin becomes activated upon proteolytic cleavage. A truncated version of the toxin (PE38) may be employed for the constructs of the present invention, as the full-length protein binds with its fist domain to the ubiquitous α2-macroglobulin receptor and is therefore toxic to most eukaryotic cells. Yet, this problem may be overcome by replacing the first domain of Pseudomonas exotoxin A by a specific sequence in order to alter the binding specificity of the toxin.

In one aspect, the present invention relates to the use of a chemokine construct which binds to a chemokine receptor for the preparation of a pharmaceutical composition for the elimination of cells which are latently infected with a primate immunodeficiency virus, wherein the chemokine construct comprises a amino acid sequence as depicted in SEQ ID NO:24 or as encoded by the nucleotide sequence as depicted in SEQ ID NO:23.

As mentioned herein, in one embodiment the chimeric polypeptide of the invention (e.g., antibody and/or chemokine constructs) can bind to or interact with a T cell surface polypeptide, e.g., the CD3 antigen. The T cell surface polypeptide (e.g., CD3 antigen) can be on the surface of an effector cell, such as a T-cell, e.g., a cytotoxic T-cell. In one embodiment, the antibody construct can comprises a binding site for CCR5 and a binding site for CD3. In one aspect, the chemokine construct comprises RANTES and a toxin, e.g., a polypeptide toxin, e.g., a truncated Pseudomonas exotoxin A (PE38), or equivalent thereof. The chimeric polypeptides of the present invention, therefore, can comprise antibody constructs comprising a binding site for CCR5 and a binding site for CD3 as well as to chemokine constructs comprising RANTES and the truncated Pseudomonas exotoxin A (PE38).

The present invention also relates to a polynucleotide encoding an antibody-construct as defined hereinabove or a polynucleotide encoding a chemokine construct as defined herein, wherein the polynucleotide can comprise a nucleic acid molecule encoding a polypeptide as depicted in SEQ ID NO:18 or SEQ ID NO:24; a polynucleotide comprising a nucleic acid molecule as depicted in SEQ ID NO:17 or SEQ ID NO:23; or a polynucleotide hybridizing under stringent conditions to a nucleic acid molecule as depicted in SEQ ID NO:17 or SEQ ID NO:23, such as a complementary strand of on of these polynucleotides.

With respect to the polynucleotides/nucleotide sequences of the invention, the term "hybridizing" in this context is understood as referring to conventional hybridization conditions, preferably such as hybridization in 50% formamide/6×SSC/0.1% SDS and 100 µg/ml ssDNA, in which temperatures for hybridization are above 37° C. and temperatures for washing in 0.1×SSC/0.1% SDS are above 55° C. Most preferably, the term "hybridizing" refers to stringent hybridization conditions, for example such as described in Sambrook., "Molecular Cloning: A Laboratory Manual", Cold Spring Harbor Laboratory Press, Cold Spring Harbor, N.Y., 1989. It is envisaged that the polynucleotides identified by hybridization, as described above, are highly homologous to the polynucleotides as defined herein (e.g., SEQ ID NO: 17 or SEQ ID NO: 23) and comprise a homology of at least about 95%, at least about 97%, or about 99% with the polynucleotides of SEQ ID NO: 17 or SEQ ID NO: 23.

Polynucleotides as defined and characterized by hybridization to SEQ ID NO: 17 or SEQ ID NO: 23, therefore, may encode for polypeptides being highly homologous to the polypeptides as defined in SEQ ID NO: 18 or SEQ ID NO: 24. The person skilled in the art can easily test the capacity of such homologous polypeptides to bind to chemokine receptors, such as a human CCR5 or CCR3 receptor, and the like, and/or to eliminate, deplete and/or destroy cells, such as infected cells, for example, cells which are infected by a primate immunodeficiency virus, like HIV-1, or eliminate, deplete and/or destroy target cells involved in immunological disorders, as disclosed herein. The person skilled in the art can easily adopt the in vitro, in vivo and ex vivo experiments of the appended examples to verify the binding and/or depletion properties of such constructs.

Furthermore, the polynucleotide/nucleic acid molecules of the invention may contain, for example, thioester bonds and/or nucleotide analogues. The modifications may be useful for the stabilization of the nucleic acid molecule, e.g., against endo- and/or exonucleases in the cell. These nucleic acid molecules may be transcribed by an appropriate vector containing a chimeric gene which allows for the transcription of said nucleic acid molecule in the cell. The polynucleotide/nucleic acid molecules of the invention may be a recombinantly produced chimeric nucleic acid molecule comprising any of the aforementioned nucleic acid molecules either alone or in combination. The polynucleotide may be, e.g., DNA, cDNA, RNA or synthetically produced DNA or RNA or a recombinantly produced chimeric nucleic acid molecule comprising any of those polynucleotides either alone or in combination. The polynucleotide can be part of a vector, e.g., an expression vector, including, e.g., recombinant viruses. The vectors may comprise further genes, such as marker genes, that allow for the selection of the vector in a suitable host cell and under suitable conditions.

In one aspect, the polynucleotides of the invention are operatively linked to expression control sequences allowing expression in prokaryotic or eukaryotic cells. Expression of the polynucleotide comprises transcription of the polynucleotide into a translatable mRNA. Regulatory elements ensuring expression in cells, including eukaryotic cells, such as mammalian cells, are well known to those skilled in the art. They usually comprise regulatory sequences ensuring initiation of transcription, and, optionally, poly-A signals ensuring termination of transcription and stabilization of the transcript. Additional regulatory elements may include transcriptional as well as translational enhancers, and/or naturally-associated or heterologous promoter regions. Exemplary regulatory elements permitting expression in prokaryotic host cells comprise, e.g., the PL, lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. The nucleic acids of the invention can also comprise, in addition to elements responsible for the initiation of transcription, other elements, such regulatory elements and transcription termination signals, such as the SV40-poly-A site or the tk-poly-A site (termination sequences are typically downstream of the polynucleotide coding sequence). Furthermore, depending on the expression system used, nucleic acid sequences encoding leader sequences capable of directing the polypeptide to a cellular compartment, or secreting it into the medium, may be added to the coding sequence of the polynucleotide of the invention; such leader sequences are well known in the art; see also, e.g., the appended examples. The leader sequence(s) is (are) assembled in appropriate phase with translation, initiation and termination sequences. In one aspect, the leader sequence is capable of directing secretion of translated chimeric protein, or a portion thereof, into the periplasmic space or extracellular medium. Optionally, the heterologous sequence can encode a fusion protein including an N-terminal identification peptide imparting desired characteristics, e.g., stabilization or simplified purification of expressed recombinant product; see supra. In this context, suitable expression vectors are known in the art such as Okayama-Berg cDNA expression vector pcDV1 (Pharmacia), pCDM8, pRc/CMV, pcDNA1, pcDNA3 (Invitrogene), or pSPORT1 (GIBCO BRL). Expression control sequences can be eukaryotic promoter systems in vectors capable of transforming or transfecting eukaryotic host cells; control sequences for prokaryotic hosts may also be used. Once the vector has been incorporated into the appropriate host, the host can be maintained under conditions suitable for high level expression of the nucleotide sequences; and, as desired, the collection and purification of the polypeptide of the invention may follow; see, e.g., the appended examples.

As described above, the polynucleotide of the invention can be used alone or as part of a vector (e.g., an expression vector or a recombinant virus), or in cells, to express the chimeric polypeptides of the invention (e.g., antibody- and/or chemokine constructs); these polynucleotides can be used for, e.g., the treatment of immunological disorders or to treat infections, e.g., in anti-viral therapy. The polynucleotides or vectors containing the DNA sequence(s) encoding any one of the chimeric polypeptides of the invention can be introduced into the cells, which in turn produce the polypeptide of interest. In one aspect, the polynucleotides and vectors are used for gene therapy. Gene therapy, which is based on introducing therapeutic genes into cells by ex vivo or in vivo techniques, is one of the most important applications of gene transfer. Suitable vectors, methods or gene-delivery systems for in vitro, ex vivo or in vivo gene therapy are described in the literature and are known to the person skilled in the art; see, e.g., Giordano (1996) Nature Medicine 2:534–539; Schaper, Circ. Res. 79 (1996), 911–919; Anderson, Science 256 (1992), 808–813; Verma, Nature 389 (1994), 239; Isner, Lancet 348 (1996), 370–374; Muhlhauser, Circ. Res. 77 (1995), 1077–1086; Onodera, Blood 91 (1998), 30–36; Verma, Gene Ther. 5 (1998), 692–699; Nabel, Ann. N.Y. Acad. Sci. 811 (1997), 289–292; Verzeletti, Hum. Gene Ther. 9 (1998), 2243–51; Wang, Nature Medicine 2 (1996), 714–716; WO 94/29469; WO 97/00957, U.S. Pat. Nos. 5,580,859; 5,589,466; or, Schaper, Current Opinion in Biotechnology 7 (1996), 635–640, and references cited therein. The polynucleotides and vectors of the invention may be designed for direct introduction or for introduction via liposomes, or viral vectors (e.g., adenoviral, retroviral) into the cell. The cell can be a germ line cell, an embryonic cell, or an egg cell, or a cell derived therefrom, e.g., a stem cell. An exemplary embryonic stem cell is described, e.g., in Nagy (1993) Proc. Natl. Acad. Sci. USA 90:8424–8428.

The present invention is directed to vectors, e.g., plasmids, cosmids, viruses and bacteriophages, or any expression system used conventionally in genetic engineering, that comprise a polynucleotide encoding a chimeric polypeptide of the invention. The vector can be an expression vector and/or a gene transfer or targeting vector. Expression vectors derived from viruses such as retroviruses, vaccinia virus, adeno-associated virus, herpes viruses, or bovine papilloma virus, may be used for delivery of the polynucleotides or vectors of the invention into targeted cell populations. Methods which are well known to those skilled in the art can be used to construct recombinant vectors; see, for example, the techniques described in Sambrook, Molecular Cloning: A Laboratory Manual, Cold Spring Harbor Laboratory (1989) N.Y. and Ausubel, Current Protocols in Molecular Biology, Green Publishing Associates and Wiley Interscience, N.Y. (1989). Alternatively, the polynucleotides and vectors of the invention can be reconstituted into liposomes for delivery to target cells. The vectors containing the polynucleotides of the invention can be transferred into the host cell by well-known methods, which vary depending on the type of cellular host. For example, calcium chloride transfection is commonly utilized for prokaryotic cells, whereas calcium phosphate treatment or electroporation may be used for other cellular hosts; see Sambrook, supra.

Once expressed, the polypeptides of the present invention can be purified according to standard procedures of the art, including ammonium sulfate precipitation, affinity columns, column chromatography, gel electrophoresis and the like; see, Scopes, "Protein Purification", Springer-Verlag, N.Y. (1982). In alternative aspects, the invention is directed to substantially pure chimeric polypeptides of at least about 90% to about 95% homogeneity; between about 95% to 98% homogeneity; and about 98% to about 99% or more homogeneity; these "substantially pure" polypeptides can be used in the preparation of pharmaceuticals. Once purified, partially or to a homogeneity as desired, the polypeptides may then be used therapeutically (including extracorporeally) or in developing and performing assay procedures.

In a still further embodiment, the present invention relates to a cell containing the polynucleotide or vector of the invention, or to a host cell transformed with a polynucleotide or vector of the invention. In alternative aspects, the host/cell is a eukaryotic cell, such as a mammalian cell, particularly if therapeutic uses of the polypeptide are envisaged. Of course, yeast and prokaryotic, e.g., bacterial cells, may serve as well, in particular, if the produced polypeptide is used for non-pharmaceutical purposes, e.g., as in diagnostic tests or kits or in screening methods.

The polynucleotide or vector of the invention that is present in the host cell may either be integrated into the genome of the host cell or it may be maintained extrachromosomally, e.g., as an episome.

The term "prokaryotic" is meant to include all bacteria that can be transformed or transfected with a DNA or RNA molecules for the expression of a polypeptide of the invention. Prokaryotic hosts may include gram negative as well as gram positive bacteria such as, for example, *E. coli, S. typhimurium, Serratia marcescens* and *Bacillus subtilis*. The term "eukaryotic" is meant to include yeast, higher plant, insect and mammalian cells. Depending upon the host employed in a recombinant production procedure, the polypeptides of the present invention may be glycosylated or may be non-glycosylated. Polypeptides of the invention may also include an initial methionine amino acid residue. A polynucleotide coding for a polypeptide of the invention can be used to transform or transfect the host using any of the techniques commonly known to those of ordinary skill in the art. In one aspect, the nucleic acids encoding the chimeric polypeptide of the invention (including those sequences in vectors, e.g., plasmid or virus) further comprise, genetically fused thereto, sequences encoding an epitope tag, e.g., an N-terminal FLAG-tag and/or a C-terminal His-tag. In one aspect, the length of said FLAG-tag is about 4 to 8 amino acids; or, is about 8 amino acids in length. Methods for preparing fused, operably linked genes and expressing them in, e.g., mammalian cells and bacteria are well-known in the art (Sambrook, Molecular Cloning: A Laboratory Manual, Cold Spring Harbor Laboratory, Cold Spring Harbor, N.Y., 1989). The genetic constructs and methods described therein can be utilized for expression of the polypeptide of the invention in eukaryotic or prokaryotic hosts. In general, expression vectors containing promoter sequences which facilitate the efficient transcription of the inserted polynucleotide are used in connection with the host. The expression vector typically contains an origin of replication, a promoter, and a terminator, as well as specific genes which are capable of providing phenotypic selection of the transformed cells. Furthermore, transgenic non-human animals, such as mammals (e.g., mice, goats), comprising nucleic acids or cells of the invention may be used for the large scale production of the chimeric polypeptides (e.g., the antibody- and/or chemokine construct) of the invention. For example, in one aspect, a transgenic non-human animal of the invention is used to produce an antibody or a chemokine construct of the invention.

In a further embodiment, the invention is directed to a process for the preparation of a polypeptide of the invention comprising cultivating a (host) cell of the invention under conditions suitable for the expression of the antibody- and/or chemokine construct and isolating the polypeptide from the cell or the culture medium. The transformed hosts can be grown in fermentors and cultured according to techniques known in the art to achieve optimal cell growth. The produced constructs of the invention can then be isolated from the growth medium, cellular lysates, or cellular membrane fractions. The isolation and purification of the expressed polypeptides of the invention (e.g., microbially expressed) may be by any conventional means such as, e.g., preparative chromatographic separations and immunological separations, such as those involving the use of monoclonal or polyclonal antibodies directed against, e.g., a tag of the polypeptide of the invention or as described in the appended examples.

Depending on the host cell, renaturation techniques may be required to attain proper conformation. If necessary, point substitutions seeking to optimize binding may be made in the DNA using conventional cassette mutagenesis or other protein engineering methodology such as is disclosed herein. Preparation of the polypeptides of the invention may also be dependent on knowledge of the amino acid sequence (or corresponding DNA or RNA sequence) of bioactive proteins such as enzymes, toxins, growth factors, cell differentiation factors, receptors, anti-metabolites, hormones or various cytokines or lymphokines. Such sequences are reported in the literature and available through computerized data banks. The present invention further relates to a chimeric polypeptide, e.g., an antibody construct or a chemokine construct, encoded by a polynucleotide of the invention or produced by the method described hereinabove.

Additionally, the present invention provides for compositions comprising the polynucleotide, the vector, the host cell, the chimeric polypeptide (e.g., antibody construct and/or the chemokine construct) of the invention.

The term "composition", in context of this invention, comprises at least one polynucleotide, vector, host cell, chimeric polypeptide (e.g., antibody construct and/or chemokine construct) of the invention, as described herein. Said composition, optionally, further comprises other molecules, either alone or in combination, such as molecules which are capable of modulating and/or interfering with the immune system. The composition may be in solid, liquid or gaseous form and may be, inter alia, in a form of a powder(s), a tablet(s), a solution(s) or an aerosol(s). In alternative embodiments, the composition comprises at least two, at least three, at least four, or more than four, compounds of the invention. The composition can be a pharmaceutical composition further comprising, optionally, a pharmaceutically acceptable carrier, diluent and/or excipient.

Examples of suitable pharmaceutical carriers are well known in the art and include phosphate buffered saline solutions, water, emulsions, such as oil/water emulsions, various types of wetting agents, sterile solutions, etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical, intraarticular (including into or near the joint space) or intradermal administration. The dosage regiment can be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Generally, the regimen as a regular administration of the pharmaceutical composition should be in the range of about 1 μg to 10 mg units per day. If the regimen is a continuous infusion, it can also be in the range of about 1 μg to 10 mg units per kilogram of body weight per minute, respectively. An alternative dosage for continuous infusion may be in the range of about 0.01 μg to 10 mg units per kilogram of body weight per hour. Other exemplary dosages are recited herein below. Progress can be monitored by periodic assessment. Dosages will vary; for example, a dosage for intravenous administration of DNA can be from approximately $10^6$ to $10^{12}$ copies of the DNA molecule. The compositions of the invention may be administered locally or systematically. Administration can be parenterally, e.g., intravenously; and, by external administration. DNA may also be administered directed to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishes, electrolyte replenishers (such as those based on Ringer's dextrose), and the like. Preservatives and other additives may also be present such as, for example, antimicrobials, anti-oxidants, chelating agents, and inert gases and the like. In addition, the pharmaceutical composition of the present invention may comprise proteinaceous carriers, like, e.g., serum albumin or immunoglobulin, including those of human origin. Furthermore, it is envisaged that the pharmaceutical composition of the invention may comprise further biologically active agents, depending on the intended use of the pharmaceutical composition. Such agents might be drugs acting on the immunological system, drugs used in anti-viral treatment, in particular in HIV-treatment (for example, HAART) and AIDS management and/or anti-inflammatory drugs. It is, for example, envisaged that patients are treated as early as possible with HAART until viral load is below detection level for several weeks to months. Early treatment of infected patients with HAART prevents the transition of viral strains from usage of CCR5 to other chemokine receptors, like CXCR4 (Connor (1997) J. Exp. Med. 185, 621–628). Pharmaceuticals of the present invention, for example, one comprising a CCR5xCD3 construct is administered in addition to HAART to eliminate latently infected cells, as well as cells that are prone to reinfection by HIV-1. The procedures for the depletion of CCR5$^+$ cells can be repeated from one to about 10 or more times. Doses of CCR5xCD3 can be in the range of about 0.5 μg/m$^2$ to 10 mg/m$^2$, or between about 10 μg/m$^2$ to 100 μg/m$^2$. Doses can be administered intravenously, subcutaneously and/or into the cerebra-spinal fluid. After several treatment cycles with the bispecific antibody HAART is discontinued and viral load is closely monitored. If viral load increases above detection level, a new cycle of HAART and the bispecific antibody is initiated as described above.

In one aspect, the various polynucleotides and vectors of the invention are administered either alone or in any combination using standard vectors and/or gene delivery systems, and, optionally, together with a pharmaceutically acceptable carrier or excipient. Subsequent to administration, the polynucleotides or vectors may be stably integrated into the genome of the subject, such as a human.

Alternatively, pharmaceutical compositions, including, e.g., vectors, such as viral vectors, of the invention are designed to be specific for (e.g., "target to") certain cells or tissues; they can also be designed to persist in cells. Suitable pharmaceutical carriers and excipients are well known in the art. The pharmaceutical compositions of the invention can be used for the prevention or treatment or delaying of different kinds of immunological diseases, e.g., autoimmune diseases, which may be related to inflammation, such as inflammatory bowel diseases, inflammatory renal diseases, inflammatory joint diseases like arthritis, e.g., chronic arthritis. Furthermore, the pharmaceutical composition of the invention may be employed to eliminate cells which are infected, e.g., with a virus, such as cells latently infected with a virus, e.g., a lentivirus or a primate immunodeficiency virus, as HIV-1.

Furthermore, it is possible to use a pharmaceutical composition of the invention comprising a polynucleotide or vector of the invention in gene therapy. Suitable gene delivery systems may include liposomes, receptor-mediated delivery systems, naked DNA, and viral vectors such as herpes viruses, retroviruses, adenoviruses, and adeno-associated viruses, among others. Delivery of nucleic acids to a specific site in the body for gene therapy may also be accomplished using a biolistic delivery system, such as that described by Williams (Proc. Natl. Acad. Sci. USA 88 (1991), 2726–2729). Further methods for the delivery of nucleic acids comprise particle-mediated gene transfer as, e.g., described in Verma, Gene Ther.15 (1998), 692–699.

It is to be understood that the introduced polynucleotides and vectors express a gene product after introduction into the cell; they can remain in this status during the lifetime of the cell. For example, cell lines that stably express the polynucleotide under the control of appropriate regulatory sequences may be engineered according to methods well known to those skilled in the art. Rather than using expression vectors that contain viral origins of replication, host cells can be transformed with the polynucleotide of the invention and a selectable marker, either on the same or separate plasmids. Following the introduction of foreign DNA, engineered cells may be allowed to grow for about 1 to 2 days in an enriched media, and then are switched to a selective media. The selectable marker in the recombinant plasmid confers resistance to the selection. This allows for the selection of cells having stably integrated the plasmid into their chromosomes; the selected cells grow to form foci, which, in turn, can be cloned and expanded into cell lines.

A number of selection systems may be used, including but not limited to, the herpes simplex virus thymidine kinase (Wigler, Cell 11 (1977), 223), hypoxanthine-guanine phosphoribosyltransferase (Szybalska, Proc. Natl. Acad. Sci. USA 48 (1962), 2026), and adenine phosphoribosyltransferase (Lowy, Cell 22 (1980), 817) in tk$^-$, hgprt$^-$ or aprt$^-$ cells, respectively. Also, antimetabolite resistance can be used as the basis of selection for dhfr, which confers resistance to methotrexate (Wigler, Proc. Natl. Acad. Sci. USA 77 (1980), 3567; O'Hare, Proc. Natl. Acad. Sci. USA 78 (1981), 1527), gpt, which confers resistance to mycophenolic acid (Mulligan, Proc. Natl. Acad. Sci. USA 78 (1981), 2072); neo, which confers resistance to the aminoglycoside G-418 (Colberre-Garapin, J. Mol. Biol. 150 (1981), 1); hygro, which confers resistance to hygromycin (Santerre (1984) Gene 30:147); or puromycin (pat, puromycin N-acetyl transferase). Additional selectable genes have been described, e.g., trpB, which allows cells to utilize indole in place of tryptophan, hisD, which allows cells to utilize histinol in place of histidine (Hartman, Proc. Natl. Acad. Sci. USA 85 (1988), 8047); and ODC (ornithine decarboxylase) which confers resistance to the ornithine decarboxylase inhibitor, 2-(difluoromethyl)-DL-ornithine, DFMO (McCologue, 1987, In: Current Communications in Molecular Biology, Cold Spring Harbor Laboratory ed.).

In a further embodiment, the invention relates to a composition, such as a pharmaceutical composition, as described hereinabove, which further comprises a medicament for the treatment or prevention of an immunological (e.g., autoimmune) disorder or a medicament for treating or preventing an infection, e.g., an anti-HIV treatment. The anti-HIV treatment may comprise HAART. HAART therapy consists of a cocktail of three classes anti-viral drugs. The classes are, e.g., nucleosidal reverse transcriptase inhibitors (NRTI), non-nucleosidal reverse transcriptase inhibitors (NNRTI) and protease inhibitors (PI). Usually 2 to 4 drugs from preferentially more than one class are combined to reduce viral load to almost non-detectable levels. Products, dosing schedules and common side effects are given in appended Tables I to III.

The treatment of an immunological disorder may comprise anti-inflammatory agents and immunosuppressive agents. Anti-inflammatory agents may be selected from the group consisting of azathioprine, cyclophosphamide, glucocorticoids like prednisone and corticosteroids. Immunosuppressive agents may comprise cyclosporin A, Tacrolimus (FK506), Sirolimus (Rapamycin). Protein drugs may comprise calcineurin, beta-interferon, anti-TNF alpha monoclonal antibodies (remicade). Dosing and use of anti-inflammatory agents and immunosuppressive agents is described, inter alia, in Fauci et al., sic. Further treatment options are known to the skilled artisan and, inter alia, described hereinabove.

In one embodiment, the invention relates to a method for treating, preventing and/or alleviating an immunological disorder, or for the elimination of infected cells, e.g., cells which are infected with a virus, e.g., cells latently infected with a primate immunodeficiency virus, comprising administering to a subject in need of such a treatment, prevention and/or alleviation, an effective amount of a compound and/or composition of the invention, such as a pharmaceutical composition of the present invention.

The constructs described herein are particularly useful in specifically destroying chemokine receptor-positive cells. For example, a bispecific antibody, binding simultaneously to CCR5 on target cells and to CD3 on T-cells, redirects cytotoxic T-cells to the CCR5 positive target cells. As shown in the appended examples the antibody construct specifically depletes CCR5 positive T-cells and monocytes, but is inactive against cells that do not express CCR5, such as CCR5 deficient Δ32/Δ32 PBMC. Furthermore, in vitro/ex vivo experiments, the bispecific antibody construct eliminated more than 95% of CCR5 positive monocytes and T-cells from the synovial fluid of patients with arthritis.

Other constructs, like chemokine constructs, for example, a fusion protein of the chemokine RANTES and a truncated version of the Pseudomonas exotoxin A (PE38), are able to bind to CCR5 and to downmodulate the receptor from the cell surface, as exemplified in the appended examples. Within 48 hours, RANTES-PE38 completely destroyed CCR5 positive CHO cells at a concentration of 2 nM. No cytotoxic effect was detectable against CCR5 negative CHO cells. Based on the predominance of CCR5 positive T-cells and monocytes in the infiltrate of chronically inflamed tissue, the specific depletion of CCR5 positive cells represents a new concept in the treatment of immunological disorders.

As described herein, due to the fact that specific chemokine receptors are present on immunodeficiency virus-infected cells (e.g., HIV-infected cells), such as CCR5, the compounds and compositions of the invention are particularly useful for the depletion/elimination of cells latently infected with primate immunodeficiency virus.

The present invention also relates to the use of the polynucleotide, the vector, the host, the chimeric polypeptides (e.g., antibody constructs and/or chemokine constructs) of the present invention for the preparation of a pharmaceutical composition for treating, preventing and/or alleviating an immunological disorder, or for the preparation of a pharmaceutical composition for treating infected cells, e.g., virally infected cells, e.g., eliminating latently infected cells, such as cells infected with a primate immunodeficiency virus, e.g., a human immunodeficiency virus, such as HIV-1.

The immunological disorders may be autoimmune diseases, skin diseases, allergic diseases, inflammatory diseases, diabetes and transplant rejections, wherein said autoimmune disease is selected from the group consisting of multiple sclerosis, type I diabetes, rheumatoid arthritis. Said skin diseases, may comprise psoriatic lesions, psoriasis, atrophic dermatitis and the like. Inflammatory disease are mentioned hereinabove is selected from the group consisting of inflammatory joint diseases, inflammatory renal diseases, inflammatory bowel diseases. In particular, said inflammatory bowel disease may comprise Morbus Crohn, sarcoidosis, systemic sclerosis, collagenosis, myositis, neuritis. Inflammatory renal diseases may comprise nephritis, glomerulonephritis, lupus nephritis, or IgA nephropathy.

In a variety of chronic inflammatory diseases, an impressive accumulation of CCR5 positive T-cells and macrophages is found at the site of inflammation. An accumulation of CCR5$^+$ cells has been demonstrated in several types of inflammatory diseases, like arthritis, inflammatory renal diseases, transplant rejection, auto-immune diseases like multiple sclerosis and inflammatory bowel diseases. In contrast, in the peripheral blood of these patients, only a minority of T-cells and monocytes express CCR5. Therefore, CCR5 appears to be an excellent marker to identify and target leukocytes that are involved in chronic inflammation. The occurrence of a 32 bp deletion in the CCR5 gene that prevents expression of CCR5 facilitates the study the pathophysiological role of CCR5 in chronic inflammatory diseases. In patients with rheumatoid arthritis, the frequency of CCR5 deficient (Δ32/Δ32) individuals is significantly reduced. Moreover, the mean survival of the kidney transplants is significantly longer in CCR5-Δ32/Δ32 patients. These results make CCR5 a target for therapeutic intervention. Furthermore, the prevalence of CCR5 positive leukocytes in the diseased tissue, in contrast to the rare expression of CCR5 on the peripheral blood leukocytes, means that a specific elimination of CCR5 positive leukocytes may be therapeutically useful by reducing the number of infiltrating cells in chronic inflammation, transplant rejection and autoimmune disease, like multiple sclerosis, without significantly depleting peripheral blood leukocytes. Eliminating CCR5 positive leukocytes from the inflammatory infiltrate will be of greater therapeutic benefit than simply blocking chemokine receptors of these cells, as they have already infiltrated the tissue.

As documented in the appended examples, the antibody and/or chemokine constructs of the invention are useful in the treatment, prevention and/or alleviation of inflammatory joint diseases. Therefore, the compositions of the present invention are useful for the treatment of inflammatory joint diseases, like arthritis, including, chronic arthritis.

The present invention furthermore, provides for medical methods and uses, wherein the composition, e.g., a pharmaceutical composition of the invention, is to be administered in combination with antiviral agents and/or in combination with drugs to be employed in AIDS management. As mentioned hereinabove, the main problem in AIDS management is the occurrence of latently HIV-infected cells. The current treatment options are based on anti-viral agents interfering with two enzymes of the HIV-1 virus, its protease and reverse transcriptase. The protease is essential to cleave the inactive viral pre-proteins to form the active products, while the reverse transcriptase is required to generate a DNA intermediate of the viral RNA genome. The DNA intermediate can then integrate into the host genome and remain there in a silent, i.e., latent, form. The most efficient treatment option consists of highly active antiretroviral therapy (HAART); this a treatment regimen that usually consists of a combination of three or more anti-retroviral drugs, usually including at least one drug of the protease inhibitor class. The advent of highly active anti-retroviral therapy (HAART) has had a significant impact on HIV-1-infected individuals, lowering circulating virus to undetectable levels (Oxenius (2000) Proc. Natl Acad. Sci. 97, 3383–3387; Perelson (1997) Nature (London) 387, 188–191; Hammer (1997) N. Engl. J. Med. 337, 725–733; Gulick (1997) N. Engl. J. Med. 337:734–739). Despite this, latently infected cells can remain in these individuals for significant periods of time (Chun (1997) Nature (London) 387, 183–188; Chun (1998) Proc. Natl. Acad. Sci. USA 95, 8869–8873; Zhang (1999) N. Engl. J. Med. 340, 1605–1613); if HAART is withdrawn, these cells can produce virus (Harrigan (1999) AIDS 13, F59–F62). A pool of latently infected cells is generated early during primary HIV-1 infection (Chun (1998) Proc. Natl. Acad. Sci. 95, 8869–8873). Considering the postulated long half-life of latent viral reservoirs (Zhang (1999) N. Engl. J. Med. 340, 1605–1613, Finzi (1999) Nat. Med 5, 512–517) and the side effects and cost of chronic HAART (Flexner (1998) N. Engl. J. Med. 338, 1281–1292; Carr (1998) Lancet 351, 1881–1883), it is important to develop new strategies to eliminate the latent reservoir. While HAART treatment has been highly successful in suppressing plasma viremia in HIV-infected individuals, there are still persistent reservoirs of HIV including in latently infected CD4+ T-cells and other cells in the brain, gut associated lymphoid tissue and the genital tract (Chun (1999) Proc. Natl. Acad. Sci. 96, 10958–10961). Re-emergence of plasma viremia after discontinuation of HAART is due to those pre-existing viral reservoirs and HAART cannot eliminate those reservoirs (Chun (2000) Nature Med. 6, 757–761). Therefore, even HAART merely suppresses viral replication and reduces the viral load but does not prevent the occurrence of latent infected cells or eliminates such cells.

Transmission of HIV-1 depends on the presence of CCR5, as individuals with a homozygous Δ32 deletion of the CCR5 allele are highly resistant against infection with HIV-1. Although highly active antiretroviral therapy can efficiently suppress replication of HIV-1, complete eradication of HIV has not been achieved to date. The main obstacle appears to be the inactivity of antiretroviral therapy against latently infected cells that can survive for several years and function as endogenous source for HIV-1. Many of these cells fail to express viral proteins and can evade the immune response. However, the majority of latently infected cells may still express CCR5, as this receptor is necessary for their initial infection. Thus, the compounds of the present invention are useful in the depletion of CCR5$^+$ cells and in the significant reduction of the number of latently infected HIV$^+$-cells. Other strategies to eliminate HIV-1 infected cells that depend on a specific recognition of viral proteins, e.g., surface expressed gp120, would be less effective against latently infected cells, as the virus is dormant in these cells.

Therefore, the compositions of the invention are useful in co-therapy approaches, which lead to a depletion of HIV-infected cells, such as CCR5-positive cells. In one aspect, the composition of the present invention is employed in combination with HAART. Products, dosing schedules and common side effects of HAART are known and illustrated, inter alia, in Tables I, II and III. The combination treatments may comprise co-administration, as well as an administration before or after treatment, with other anti-viral, preferably anti-retroviral (e.g. anti-HIV) medication.

The present invention also provides for a kit comprising a polynucleotide, a vector, a host cell, a chimeric polypeptide (e.g., an antibody construct and/or a chemokine construct) of the present invention. The kit of the invention may further comprise a storage solution(s) and/or other reagents or materials required for the conduct of scientific or therapeutic methods. The kit may, inter alia, comprise drugs and/or medicaments employed in the treatment of immunological disorders as defined herein and/or in AIDS management. Furthermore, parts of the kit of the invention can be packaged individually in vials or bottles or in combination in containers or multicontainer units. The kits may further comprise instructions for using the compositions of the invention in the treatment or prevention of infections or immune-related diseases, their use in screening or diagnostic procedures, or other methods and protocols.

EXAMPLES

The following example is offered to illustrate, but not to limit the claimed invention.

Example 1

Cloning, Recombinant Expression and Characterization of Nucleic Acids and Polypeptides of the Invention The following example describes the initial cloning and recombinant expression of exemplary nucleic acids and polypeptides of the invention and their characterization.

1.1 Generation of a CHO Cell Line Expressing Human CCR5

The cDNA sequence of CCR5 was amplified from genomic DNA of human peripheral blood mononuclear cells (PBMC) by PCR with Pfu-polymerase (Stratagene, San Diego, Calif.), oligonucleotide primers were:

```
SEQ ID NO.1:
5' GGA ACA AGA TGG ATT ATC AAG TGT C 3'

SEQ ID NO.2:
5' CTG TGT ATG AAA ACT AAG CCA TGT G 3'
```

The amplified fragment was gel purified, ligated into the PCR-Script Amp Sk(+) script vector (Stratagene) and sequenced. After subcloning into the PEF-DHFR vector, DHFR-deficient CHO cells were transfected by electroporation and selected for stable expression in nucleoside free MEM medium with 10% dialyzed FCS as described. The CHO/CCR5 transfected cells were shown to be homogeneous by FACS-analysis.

1.2 PBMC Purification

PBMC were isolated from buffy coats or full blood of healthy donors by Ficoll density gradient centrifugation. Where indicated PBMC were used from donors with a homozygous 32 base pair deletion in the CCR5 allele (Δ32/Δ32) preventing surface expression of CCR5. Specifically, buffy coats were diluted 1:2 in 0.9% NaCl, and 35 ml were layered onto 15 ml of Ficoll Paque and centrifuged for 25 min at 400 g. The white interphase was harvested and thrombocytes depleted by three subsequent washing and centrifugation steps at 100 g for 6 min in RPMI with 10% FCS. Freshly isolated monocytes expressed a very low level of CCR5, but expression was strongly induced after culture of PBMC in RPMI with 10% FCS for 24 to 48 h at 37° C. The amount of FCS did not influence this induction. The expression of CCR5 on lymphocytes was not altered during culture.

1.3 Synovial Fluid

Synovial fluid of patients with arthritis was obtained from diagnostic or therapeutic arthrocentesis and used for the experiments without further preparation. Informed consent was obtained from all patients. Synovial fluid and blood samples were simultaneously obtained from 23 patients who presented with gonarthritis for diagnostic or therapeutic arthrocentesis. Diagnoses included rheumatoid arthritis (7), reactive arthritis (3), undifferentiated gonarthritis (4), psoriatic arthritis (3), osteoarthritis (2), ancylosing spondylitis (1) and gout (3) according to ACR criteria, where applicable. Written informed consent was obtained from all patients. Synovial fluid was analyzed by light microscopy. Crystals were identified by polarized light microscopy. Student's t-test and paired t-test was applied for statistical analysis.

1.4 Analysis of Chemokine Receptor Expression in Whole Blood Samples and Synovial Fluid Immediately after arthrocentesis SF (synovial fluid) leukocytes were isolated by two washing steps with 5% PBS in NaCl 0.9%. Synovial fluid cells and whole blood (containing 1 mM EDTA) were incubated on ice with monoclonal antibodies against chemokine receptors and the appropriate isotype controls at a concentration of 10 µg/ml. The antibodies were for CCR5: MC-1 (Mack (1998) J. Exp. Med. 187, 1215–1224), for CCR2: DOC-3, which specifically binds to CCR2 (9), for CCR1: Clone 53504 (R&D-Systems), for CXCR1: 5A12 (Pharmingen), for CXCR2: 6C6 (Pharmingen), and for CXCR4 12G5 (Pharmingen), IgG1-, IgG2a- and IgG2b-isotype controls (Sigma). After two washing steps cells were incubated for 30 min on ice with a PE-conjugated rabbit-anti-mouse F(ab)2 fragment (R439, DAKO). Cells were washed twice and incubated with 10% mouse serum followed by a combination of CD4-FITC, CD8-PECy5 and CD14-APC (Immunotech). After lysis of erythrocytes, cells were immediately analyzed by flow cytometry (Becton-Dickinson). Calculations were performed with Cell Quest™ analysis software. Helper T cells, cytotoxic T cells, monocytes and neutrophils were identified by their light scatter properties and the expression or absence of CD4, CD8 and CD 14. Chemokine receptor expression was calculated after defining a cutoff according to the isotype control.

In both acute and chronic joint effusions, a consistently increased percentage of CD4+ and CD8+ T cells that expressed the chemokine receptor CCR5 was found, compared to the peripheral blood. These data are in good agreement with previous reports (Mack (1999) Arthritis Rheum. 42, 981–988; Qin (1998) J. Clin. Invest. 101, 746–754).

Figure 2:
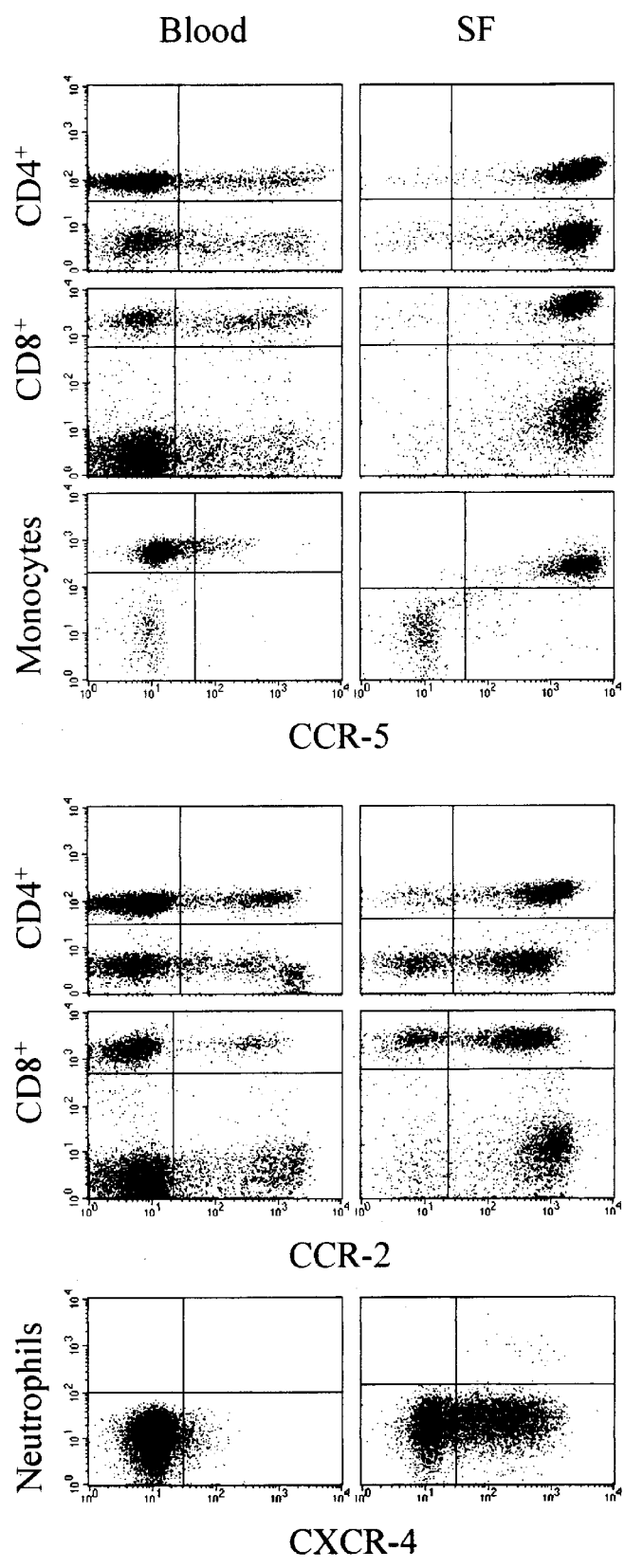
FIG. 2 panels represent FACS dot plots showing the expression of CCR5, CCR2 and CXCR4 on leukocytes in the peripheral blood (left) and synovial fluid (right) of one patient with rheumatoid arthritis. The cut-offs were set according to the isotype controls and are shown as vertical lines. In the synovial fluid the majority of T-cells and monocytes show a high level of CCR5 expression, while in the peripheral blood only a minority of these cells express low levels of CCR5.

Chemokine receptor expression on T cells in non-crystal induced arthritis: Approximately 88% of CD4+ T cells and 93% of the CD8+ T cells from the synovial fluid stained positive for the chemokine receptor CCR5. Similarly, a major proportion of CD8+ and CD4+ T cells in the SF expressed CCR2 (66% and 48%) (FIG. 1). In contrast, in the peripheral blood only a minority of T cells expressed the chemokine receptors CCR5 or CCR2. The enrichment in the synovial fluid was most pronounced for the CCR5+ helper-T cells (blood: SF ratio=1:4). The majority of T lymphocytes stained positive for CXCR4 in both compartments. CXCR1, CXCR2 and CCR1 were only expressed by a minor and variable percentage of T cells (FIG. 1). A typical example of one patient is shown in FIG. 2, showing the expression of CCR5, CCR2 and CXCR4 on leukocytes in the peripheral blood and synovial fluid.

Chemokine receptor expression on monocytes in non-crystal induced arthritis: Consistent with previous data, the majority of monocytes in the synovial fluid (SF) expressed CCR5. In addition, a reduced expression of CXCR1, CXCR2, CXCR4 and CCR1 is here reported on monocytes in the synovial fluid compared to the peripheral blood (FIGS. 1, 2). Not only was a lower frequency of receptor positive cells found, but also a lower density of chemokine receptors on the cell surface (data not shown). No differences could be detected in relation to the underlying diagnoses, duration of joint effusion or pretreatment. CCR2 was equally expressed by all monocytes in both compartments (FIGS. 1, 2).

Chemokine receptor expression on neutrophils in non-crystal induced arthritis: Acute arthritis is characterized by a rapid influx of neutrophils into the inflamed joint. Therefore, the chemokine receptor expression on neutrophils from inflamed joint effusions was analyzed. For the first time a high expression of CXCR4 is described on a large fraction of neutrophils (60%) from the synovial fluid of patients with acute and chronic arthritis, while a much lower expression was found in the peripheral blood (24%) (FIGS. 1, 2). In arthritis other than gout CXCR1 and CXCR2 was reduced on neutrophils from the synovial fluid by approximately 50% compared to the peripheral blood. CCR1 was expressed only by a minority of neutrophils in both compartments.

1.5 Determination of CCR5 Genotype

Genomic DNA was prepared from frozen blood samples by affinity chromatography (Roche Diagnostics). Subsequently a fragment of the CCR5 gene containing the potential 32 base pair deletion was amplified by a 40 cycle PCR with Taq polymerase. The primers were

SEQ ID NO.3:  5' TTT ACC AGA TCT CAA AAA GAA G 3'

SEQ ID NO.4:  5' GGA GAA GGA CAA TGT TGT AGG 3'

Differences in the length of the PCR fragments (274 or 242 bp) allowed to identify CCR5-wildtype and CCR5-Δ32 alleles.

Example 2

Construction of an Exemplary Bispecific Antibody of the Invention

The following example describes the construction of an exemplary bispecific antibody of the invention and its characterization.

2.1 Generation of Monoclonal Antibodies Against Human CCR5

To generate monoclonal antibodies against human CCR5, five BALB/c mice were immunized intraperitoneally (i.p.) at four week intervals, first with 1×10⁷ PBMC cultured for 10 days in IL-2 (100 U/ml) and six subsequent i.p. injections of 1×10⁷ CHO cells expressing high levels of CCR5. For this purpose, CCR5 transfected CHO cells were grown in the presence of 20 nM methotrexate to amplify expression of CCR5 and one clone expressing high levels of CCR5 was chosen. Four days after the last i.p. injection of CHO/CCR5 cells, the spleens were removed and the cells fused with the P3X63-Ag8 cell line. Supernatants from approximately 6000 hybridomas were screened per fusion by flow cytometry on stable CHO/CCR5 cells and monoclonal antibodies against CCR5 (MC-1, MC-4, MC-5) were detected after the third fusion. The specificity of MC-1 (IgG1), MC-4, MC-5 were tested on CHO cells stably transfected with CCR1-3 and CXCR4. In all cases no binding was detected. In addition the antibodies did not react with freshly isolated PBMCs and cultured PBMCs from a donor homozygous for the Δ32 deletion in the CCR5 gene.

2.2 Cloning of the Variable Domains of MAb MC-1 Against CCR5

The light (VL) and heavy (VH) variable domains from the αCCR5 hybridoma MC-1 were cloned using PCR amplification (Orlandi (1989) Proc. Natl. Acad. Sci. 86, 3833). Reverse transcription was carried out with random hexamer nucleotides and SuperScript reverse transcriptase (Gibco). The variable domains were amplified by PCR with Pfu-polymerase, subcloned into the vector PCR-script Amp SK+ (Stratagene) and sequenced.

For PCR amplification of VL(1) the following primers were used:

SEQ ID NO.5: 5' GACATTCAGC TGACCCAGTC TCCA 3'

SEQ ID NO.6: 5' GTTTTATTTC CAGCTTGGTC CC 3'

SEQ ID NO.7: 5' ACCATGGGAT GGAGCTGTGT CATGCTCTT and

SEQ ID NO.8: 5' TGAGGAGACG GTGACCGTGG TCCCTTGGCC CCAG

For PCR amplification of VH(1) the following primers were used:

The nucleotide sequence of VL(1) obtained by RT PCR is SEQ ID NO. 9:

```
  1  GACATTCAGC TGACCCAGTC TCCAGCCTCC CTATCTGCAT CTGTGGGAGA AACTGTCACC
 61  ATCACATGTC GAGCAAGTGA GAATATTTAC AGTTATTTAG CATGGTATCA GCAGAAACAG
121  GGAAAATCTC CTCAACTCCT GGTCTATAAT GCAAAAACCT TAACAGAAGG TGTGCCATCA
181  AGGTTCAGTG GCAGTGGATC AGGCACACAG TTTTCTCTGA AGATCAACAG CCTGCAGCCT
241  GAAGATTTTG GGAATTATTT CTGTCAACAT CATTATGATA CTCCTCGGAC GTTCGGTGGA
301  GGGACCAAGC TGGAAATAAA AC
```

The corresponding translated protein sequence to VL(1) is SEQ ID NO. 10:

```
  1  D I Q L T Q S P A S L S A S V G E T V T I T C R A S E N I Y
 31  S Y L A W Y Q Q K Q G K S P Q L L V Y N A K T L T E G V P S
 61  R F S G S G S G T Q F S L K I N S L Q P E D F G N Y F C Q H
 91  H Y D T P R T F G G G T K L E I K
```

The nucleotide sequence of VL(1) without the primer sequences used for amplification, SEQ ID NO. 11:

```
  1  GCCTCCCTAT CTGCATCTGT GGGAGAAACT GTCACCATCA CATGTCGAGC AAGTGAGAAT
 61  ATTTACAGTT ATTTAGCATG GTATCAGCAG AAACAGGGAA AATCTCCTCA ACTCCTGGTC
121  TATAATGCAA AAACCTTAAC AGAAGGTGTG CCATCAAGGT TCAGTGGCAG TGGATCAGGC
181  ACACAGTTTT CTCTGAAGAT CAACAGCCTG CAGCCTGAAG ATTTTGGGAA TTATTTCTGT
241  CAACATCATT ATGATACTCC TCGGACGTTC GGTGGA
```

The corresponding translated protein sequence to SEQ ID NO. 11: of VL(1) is SEQ ID NO. 12:

```
  1  A S L S A S V G E T V T I T C R A S E N I Y S Y L A W Y Q Q
 31  K Q G K S P Q L L V Y N A K T L T E G V P S R F S G S G S G
 61  T Q F S L K I N S L Q P E D F G N Y F C Q H H Y D T P R T F
 91  G G
```

The sequence of VH(1) including the leader sequence obtained by RT PCR is SEQ ID NO. 13:

```
  1  ATGGGATGGA GCTGTGTCAT GCTCTTCTTG GTAGCAACAG CTACAGGTGT CCACTCCCAG
 61  GTCCAACTGC AGCAGCCTGG GGCTGGGAGG GTGAGGCCTG GAGCTTCAGT GAAGCTGTCC
121  TGCAAGGCTT CTGGCTACTC CTTCACCAGT TACTGGATGA ACTGGGTGAA GCAGAGGCCT
```

```
181   GGACAAGGCC TTGAGTGGAT TGGCATGATT CATCCTTCCG ATAGTGAAAC TAGGTTAAAT

241   CAGAAGTTCA ACGACAGGGC CACATTGACT GTTGACAAAT ATTCCAGCAC AGCCTATATA

301   CAACTCAGCA GCCCGACATC TGAGGACTCT GCGGTCTATT ACTGTGCAAG AGGAGAATAT

361   TACTACGGTA TATTTGACTA CTGGGGCCAA GGGACCACGG TCACCGTCTC CTCA
```

The corresponding translated protein sequence to VH(1) is SEQ ID NO. 14:

```
  1 M G W S C V M L F L V A T A T G V H S Q V Q L Q Q P G A G R

31 V R P G A S V K L S C K A S G Y S F T S Y W M N W V K Q R P

61 G Q G L E W I G M I H P S D S E T R L N Q K F N D R A T L T

91 V D K Y S S T A Y I Q L S S P T S E D S A V Y Y C A R G E Y

121 Y Y G I F D Y W G Q G T T V T V S S
```

The nucleotide sequence of VH(1) without the leader sequence and primer sequences used for amplification, SEQ ID NO. 15:

```
  1 CTTGGTAGCA ACAGCTACAG GTGTCCACTC CCAGGTCCAA CTGCAGCAGC CTGGGGCTGG

61 GAGGGTGAGG CCTGGAGCTT CAGTGAAGCT GTCCTGCAAG GCTTCTGGCT ACTCCTTCAC

121 CAGTTACTGG ATGAACTGGG TGAAGCAGAG GCCTGGACAA GGCCTTGAGT GGATTGGCAT

181 GATTCATCCT TCCGATAGTA AAACTAGGTT AAATCAGAAG TTCAACGACA GGGCCACATT

241 GACTGTTGAC AAATATTCCA GCACAGCCTA TATACAACTC AGCAGCCCGA CATCTGAGGA

301 CTCTGCGGTC TATTACTGTG CAAGAGGAGA ATATTACTAC GGTATATTTG ACTA
```

The corresponding translated protein sequence to SEQ ID NO. 15 of VH(1) is SEQ ID NO. 16:

```
 1 L V A T A T G V H S Q V Q L Q Q P G A G R V R P G A S V K L

31 S C K A S G Y S F T S Y W M N W V K Q R P G Q G L E W I G M

61 I H P S D S E T R L N Q K F N D R A T L T V D K Y S S T A Y

91 I Q L S S P T S E D S A V Y Y C A R G E Y Y Y G I F D
```

2.3 Construction and Expression of the Bispecific Single Chain Antibody CCR5xCD3

Figure 3:
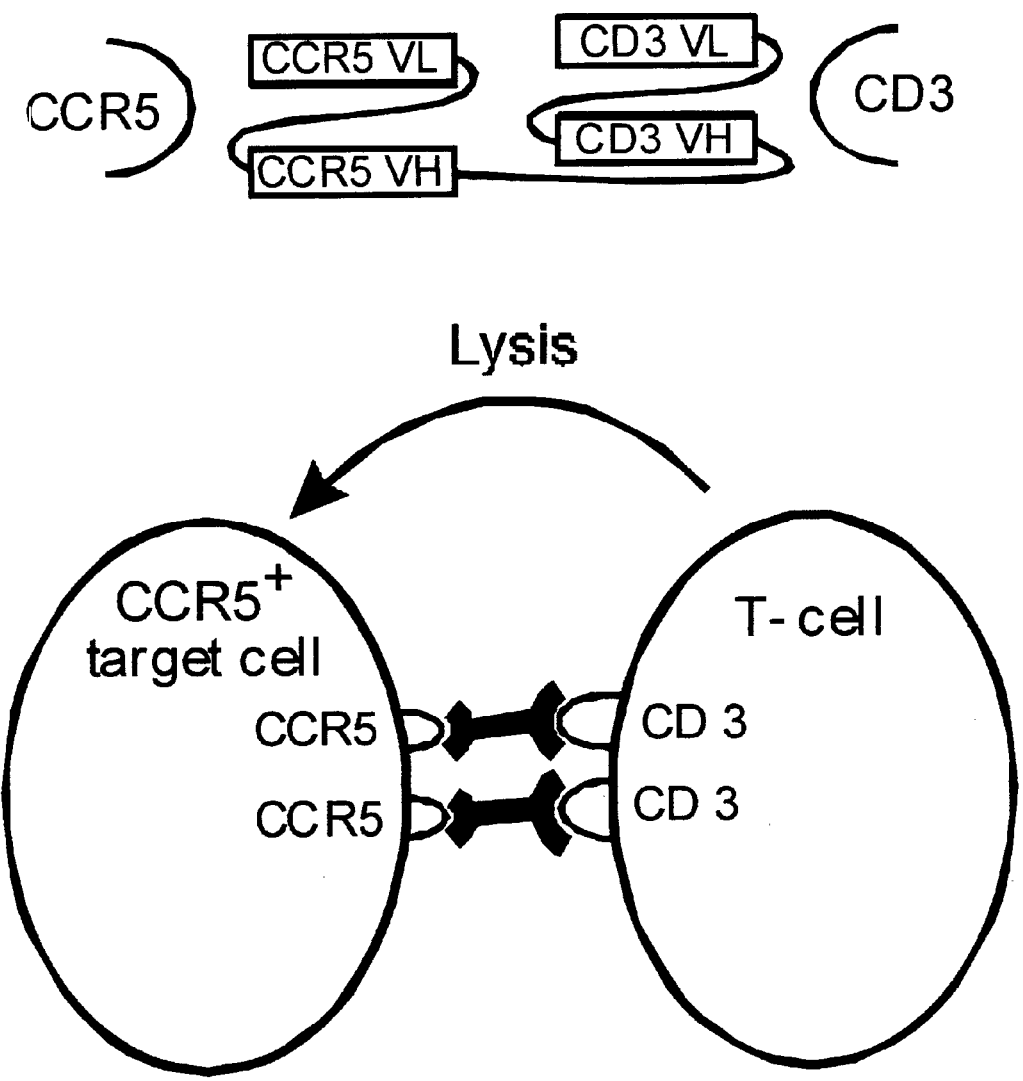
FIG. 3 shows a schematic of the bispecific single-chain antibody, and its simultaneous binding to a CCR5+ target cell and a CD3+ T cell, e.g., a cytotoxic T cell. The αCCR5 single-chain fragment (CCR5 VL/CCR5 VH) derived from the hybridoma MC-1 is fused to the N-terminus of a single-chain fragment directed against CD3 (CD3 VH/CD3 VL). Binding of the bispecific antibody to CD3+ T cells and CCR5 positive target cells results in crosslinkage of CD3, activation of effector T cells (e.g., cytotoxic T cells) and lysis of CCR5+ positive target cells.

A schematic depiction of structure and mode of action of the CCR5xCD3 bispecific single chain antibody is shown in FIG. 3. As described previously, the light and heavy variable domains were joined to a single-chain fragment using a (Gly4Ser1)3 linker and expressed in the periplasmic space of E. coli to test binding of the recombinant protein to CCR5. Subsequently, the DNA sequence of the αCCR5 single-chain fragment was subcloned with BsrG1 and BspE1 into an eukaryotic expression vector (pEF-DHFR) that already contained a single-chain fragment directed against CD3 with a C-terminally attached tail of 6 histidine residues (Mack (1995) Proc. Natl. Acad. Sci. 92, 7021). The αCCR5 and αCD3 single-chain fragments were joined by a linker coding for Gly4Ser1 (see FIG. 3).

The following order of the domains is chosen: VL(1)-VH(1)-VH(2)-VL(2), with (1) being the specificity against CCR5 and (2) the specificity against CD3.

The bispecific CCR5xCD3 antibody has the following nucleotide sequence, SEQ ID NO:17:

```
 1 ATGGGATGGA GCTGTATCAT CCTCTTCTTG GTAGCAACAG CTACAGGTGT ACACTCCGAT

61 ATCGTGCTGA CCCAGTCTCC AGCCTCCCTA TCTGCATCTG TGGGAGAAAC TGTCACCATC
```

-continued

```
 121 ACATGTCGAG CAAGTGAGAA TATTTACAGT TATTTAGCAT GGTATCAGCA GAAACAGGGA
 181 AAATCTCCTC AACTCCTGGT CTATAATGCA AAAACCTTAA CAGAAGGTGT GCCATCAAGG
 241 TTCAGTGGCA GTGGATCAGG CACACAGTTT TCTCTGAAGA TCAACAGCCT GCAGCCTGAA
 301 GATTTTGGGA ATTATTTCTG TCAACATCAT TATGATACTC CTCGGACGTT CGGTGGAGGG
 361 ACCAAGCTCG AGATCAAAGG TGGTGGTGGT TCTGGCGGCG GCGGCTCCGG TGGTGGTGGT
 421 TCTCAGGTCC AACTGCAGCA GCCTGGGGCT GGAGGGTGA GGCCTGGAGC TTCAGTGAAG
 481 CTGTCCTGCA AGGCTTCTGG CTACTCCTTC ACCAGTTACT GGATGAACTG GGTGAAGCAG
 541 AGGCCTGGAC AAGGCCTTGA GTGGATTGGC ATGATTCATC CTTCCGATAG TGAAACTAGG
 601 TTAAATCAGA AGTTCAACGA CAGGGCCACA TTGACTGTTG ACAAATATTC CAGCACAGCC
 661 TATATACAAC TCAGCAGCCC GACATCTGAG GACTCTGCGG TCTATTACTG TGCAAGAGGA
 721 GAATATTACT ACGGTATATT TGACTACTGG GGCCAAGGGA CCACGGTCAC CGTCTCCTCC
 781 GGAGGTGGTG GATCCGATAT CAAACTGCAG CAGTCAGGGG CTGAACTGGC AAGACCTGGG
 841 GCCTCAGTGA AGATGTCCTG CAAGACTTCT GGCTACACCT TTACTAGGTA CACGATGCAC
 901 TGGGTAAAAC AGAGGCCTGG ACAGGGTCTG GAATGGATTG GATACATTAA TCCTAGCCGT
 961 GGTTATACTA ATTACAATCA GAAGTTCAAG GACAAGGCCA CATTGACTAC AGACAAATCC
1021 TCCAGCACAG CCTACATGCA ACTGAGCAGC CTGACATCTG AGGACTCTGC AGTCTATTAC
1081 TGTGCAAGAT ATTATGATGA TCATTACTGC CTTGACTACT GGCGCCAAGG CACCACTCTC
1141 ACAGTCTCCT CAGTCGAAGG TGGAAGTGGA GGTTCTGGTG AAGTGGAGG TTCAGGTGGA
1201 GTCGACGACA TTCAGCTGAC CCAGTCTCCA GCAATCATGT CTGCATCTCC AGGGGAGAAG
1261 GTCACCATGA CCTGCAGAGC CAGTTCAAGT GTAAGTTACA TGAACTGGTA CCAGCAGAAG
1321 TCAGGCACCT CCCCCAAAAG ATGGATTTAT GACACATCCA AGTGGCTTC TGGAGTCCCT
1381 TATCGCTTCA GTGGCAGTGG GTCTGGGACC TCATACTCTC TCACAATCAG CAGCATCGAG
1441 GCTGAAGATG CTGCCACTTA TTACTGCCAA CAGTGGAGTA GTAACCCGCT CACGTTCGGA
1501 GCTGGGACCA AGCTGGAGCT GAAACATCAT CACCATCATC ATTAG
```

The bispecific CCR5xCD3 antibody has the following protein sequence, SEQ ID NO:18:

```
  1 D I V L T Q S P A S L S A S V G E T V T I T C R A S E N I Y
 31 S Y L A W Y Q Q K Q G K S P Q L L V Y N A K T L T E G V P S
 61 R F S G S G S G T Q F S L K I N S L Q P E D F G N Y F C Q H
 91 H Y D T P R T F G G G T K L E I K G G G G S G G G G S G G G
121 G S Q V Q L Q Q P G A G R V R P G A S V K L S C K A S G Y S
151 F T S Y W M N W V K Q R P G Q G L E W I G M I H P S D S E T
181 R L N Q K F N D R A T L T V D K Y S S T A Y I Q L S S P T S
211 E D S A V Y Y C A R G E Y Y Y G I F D Y W G Q G T T V T V S
241 S G G G G S D I K L Q Q S G A E L A R P G A S V K M S C K T
271 S G Y T F T R Y T M H W V K Q R P G Q G L E W I G Y I N P S
301 R G Y T N Y N Q K F K D K A T L T T D K S S S T A Y M Q L S
331 S L T S E D S A V Y Y C A R Y Y D D H Y C L D Y W R Q G T T
```

```
                                              -continued
361 L T V S S V E G G S G G S G G S G G S G G V D D I Q L T Q S

391 P A I M S A S P G E K V T M T C R A S S S V S Y M N W Y Q Q

421 K S G T S P K R W I Y D T S K V A S G V P Y R F S G S G S G

451 T S Y S L T I S S M E A E D A A T Y Y C Q Q W S S N P L T F

481 G A G T K L E L K H H H H H H *
```

The bispecific antibody was expressed in DHFR-deficient CHO cells and purified from the culture supernatant by affinity chromatography on immobilized $Ni^{2+}$ ions (Hochuli (1988) Biotechnology 6:1321–1325; Ni-NTA, Qiagen, Valencia, Calif.).

In summary, for the construction of bispecific antibodies, for example, the single-chain technique may be used, see, e.g., Mack (1995) Proc. Natl. Acad. Sci. USA 92:7021–7025; Mack (1997) J. Immunol. 158:3965–3970. In this case, as shown schematically in FIG. 3 (top), the variable domains of the light (VL) and the heavy (VH) immunoglobulin chains of two different antibodies are fused in a particular order, optionally a histidine chain of 6×His is attached in addition. The fusion is effected on a DNA basis so that a protein chain with four different variable domains is formed after expression (cf. FIG. 3 (top)). The attached histidine chain enables a simple and efficient purification via immobilized Ni ions in one step. FIG. 3 (top) shows a preferred embodiment of the bispecific antibody binding to the CD3 antigen on the surface of the effector cell and the human CCR5 on the surface of leukocytes as target cells.

Figure 5:
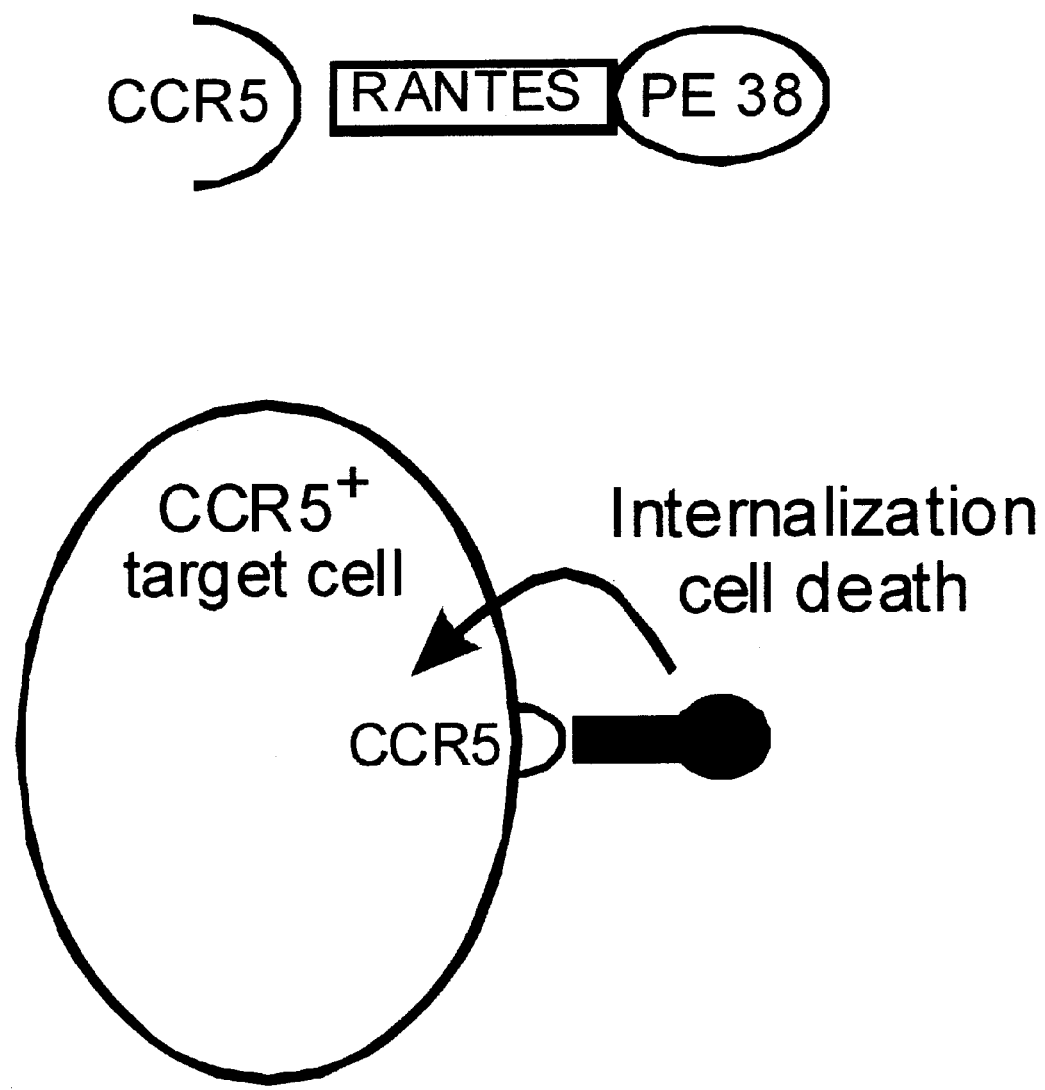
FIG. 5 is a schematic of the chemokine-toxin RANTES-PE38. The chemokine RANTES is fused to the N-terminus of a truncated version of the Pseudomonas exotoxin A (PE38). While the truncated toxin alone is unable to bind to eukaryotic cells, the fusion protein binds with the RANTES moiety to CCR5 and becomes internalized into the cell and, once intracellular, the toxin can inhibit protein synthesis and induce cell death.

Subsequently, a single-chain antibody with a specificity is generated by means of fusion PCR by inserting a linker of A schematic depiction of structure and mode of action of the RANTES-PE38 chemokine-toxin fusion protein is shown in FIG. 5. A PCR fragment of RANTES, generated with the primers P1 and P2, was subcloned with StuI and SalI into a vector for periplasmic expression in *E. coli* (Mack (1995) Proc. Natl. Acad. Sci. 92, 7021). The restriction site StuI had previously been introduced at the 3' terminus of the OmpA signal sequence. The DNA of a truncated version of Pseudomonas exotoxin A (PE38; Theuer (1993) Cancer Res. 53, 340), was amplified by PCR with Pfu-polymerase using the primers P3 and P4 and subcloned with BspE1 and Hind III into the vector that already contained the cDNA of RANTES. Primer P4 also added a tail of 6 histidine residues at the 3' terminus of PE38. During the periplasmic expression the OmpA signal sequence is cleaved off such that the recombinant protein starts with the first aminoacid of RANTES. The C-terminally attached tail of 6 histidine residues allowed purification by affinity chromatography on Ni-NTA (Qiagen).

List of Primers:

```
SEQ ID NO. 19: 5' AAAGGCCTCCCCATATTCCTCGGA

SEQ ID NO. 20: 5' AAAGTCGACTCCGGACATCTCCAAAGAGTTGATGTAC

SEQ ID NO. 21: 5' AATCCGGAGGCGGCAGCCTGGCCGC

SEQ ID NO: 22: 5' GGGAAGCTTAGTGATGGTGATGGTGATGCTTCAGGTCCTCGCGCGG
```

$(Gly_4Ser_1)_3$ between the two variable antibody domains. In a further fusion PCR, the antibody fragment against CCR5 is fused to the already published antibody fragment against CD3, with a linker consisting of $Gly_4Ser_1$ is inserted (cf. Mack et al. supra).

Figure 4:
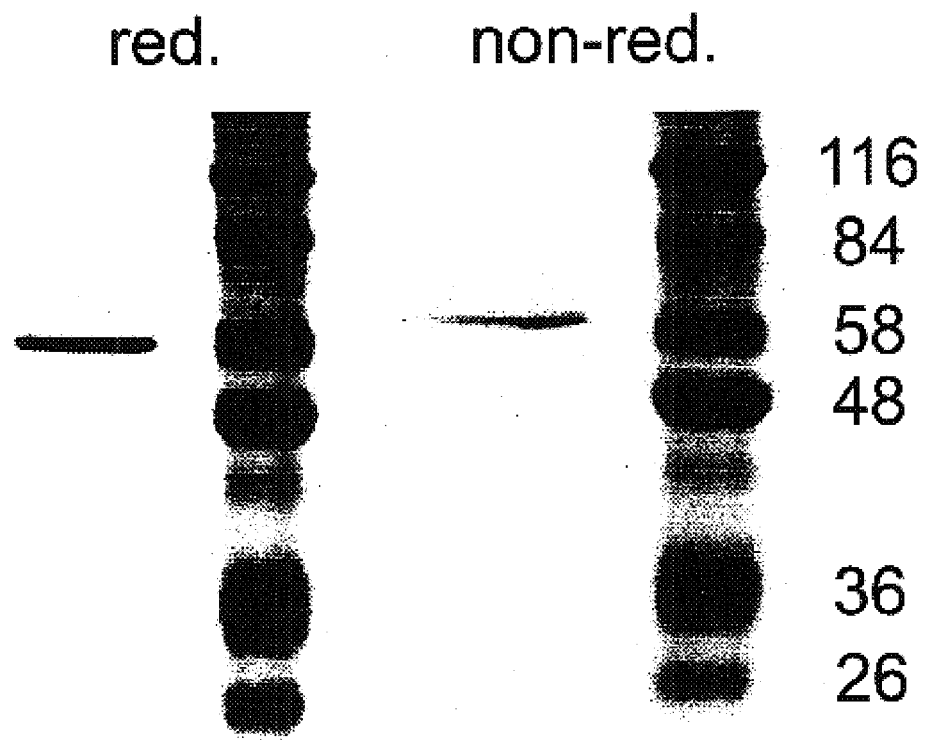
FIG. 4 is a representation of an SDS-PAGE of the purified bispecific single-chain antibody αCCR5-αCD3. A single band of approx. 60 kD is visible under reducing (red.) (left) and non-reducing ("non-red.") (right) conditions. No degradation or proteolysis of the bispecific antibody is detectable. Molecular weight (MW) markers in kilodaltons (kd) are shown to the right.

In order to express the bispecific antibody, the corresponding DNA sequence is subcloned in a eukaryotic expression vector (e.g. PEF-DHFR, Mack (1995) PNAS, supra) and transfected in DHFR-deficient CHO cells by means of electroporation. The bispecific antibody is purified from the supernatant of stably transfected CHO cells by means of affinity chromatography at Ni-NTA, with elution taking place by lowering the pH value. Subsequently, the pH is adjusted and the protein is adjusted to a suitable concentration. Overall purification yield was approx. 900 μg/l culture supernatant. SDS-PAGE showed a single band of approx. 60 kD under reducing and non-reducing conditions without any detectable proteolysis or degradation of the protein (FIG. 4).

Example 3
Expression and Purification of an Exemplary Chemokine-toxin Fusion Protein of the Invention The following example describes the expression and purification of an exemplary chemokine-toxin fusion protein of the invention and its characterization.

Figure 6:
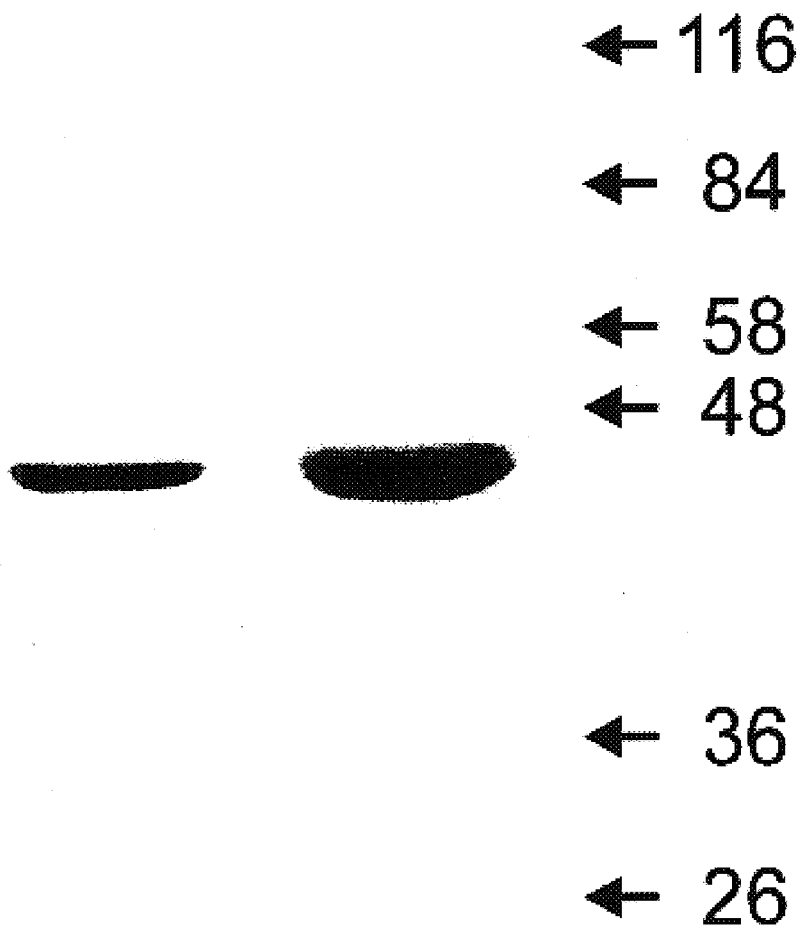
FIG. 6 is a representation of an SDS-PAGE (left) and Western blot (right) of the purified protein RANTES-PE38. A distinct band with the expected size of approx. 46 kD is visible in the Coomassie (protein-) stained SDS-PAGE and Western blot. Molecular weight (MW) markers in kilodaltons (kd) are shown to the right.

As described in the above, the DNA sequence of RANTES was fused with the sequence of a truncated version of the Pseudomonas exotoxin A (PE38) (Theuer (1993) Cancer Res. 53, 340). In a first version of the construct a Gly-Ser linker was spaced between RANTES and PE38. However, this resulted in a considerable proteolytic degradation of the fusion protein during expression in *E. coli* (data not shown). In an attempt to stabilize the construct the linker and the fist three amino acids of PE38 were removed. The new fusion protein showed no proteolysis during expression in the periplasmic space of *E. coli* as demonstrated by SDS-PAGE (FIG. 6 left panel) and Western-blot (FIG. 6 right panel). The corresponding constructs are depicted in SEQ ID NOs: 23 and 24, respectively.

Example 4
Binding of an Exemplary Bispecific Antibody of the Invention to the Target Antigens CCR5 and CD3

The following example describes the binding of an exemplary bispecific antibody to the target antigens CCR5 and CD3.

Figure 7:
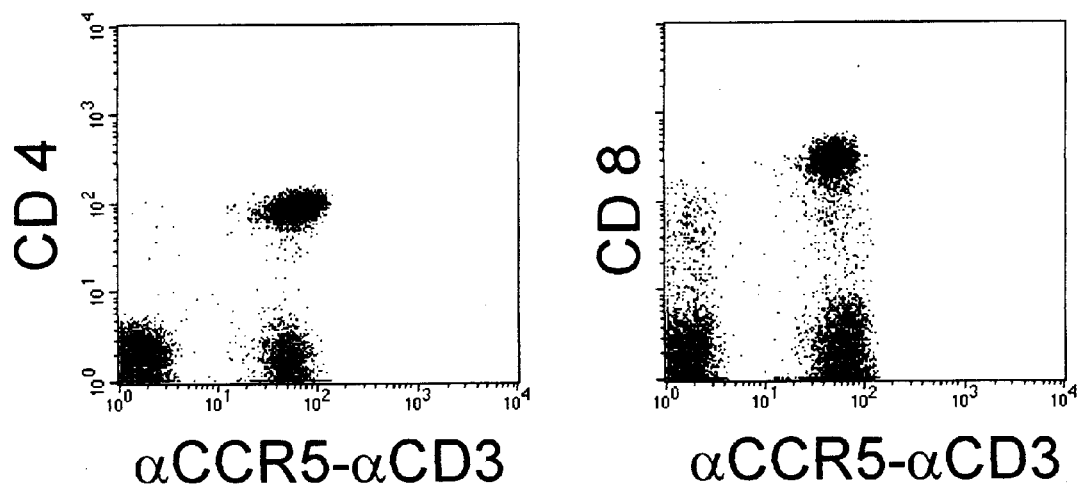
FIG. 7 panels represent FACS histograms showing the binding of the αCCR5-αCD3 bispecific antibody to CD3 on CCR5 deficient lymphocytes. Co-staining of the cells with CD4 specific antibody and CD8 specific antibody demonstrated that the bispecific antibody binds to a subpopulation of CD4+/CD8+ T cells. Multicolor analysis showed that no binding to other cell populations occurred.
Figure 8:
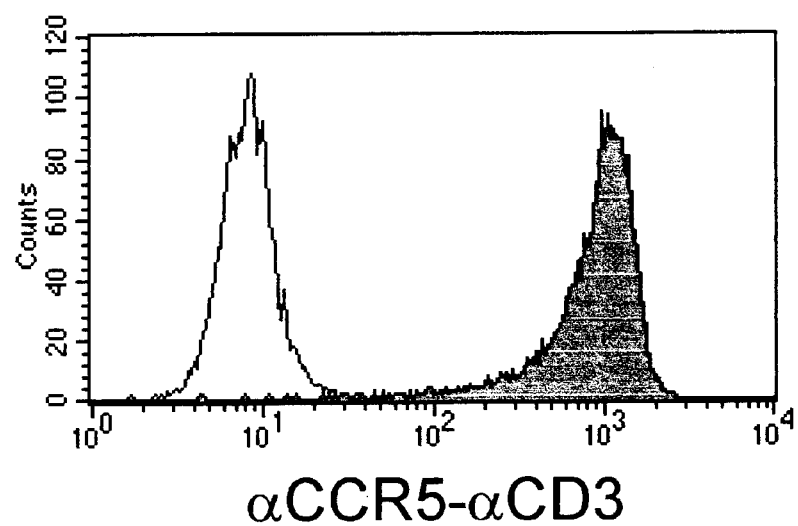
FIG. 8 summarizes data measuring the binding of the αCCR5-αCD3 bispecific antibody to CCR5 on transfected CHO cells. CHO cells transfected with CCR5 are shown in black, while CXCR4 positive CHO cells served as negative control and are shown in white.
Figure 9:
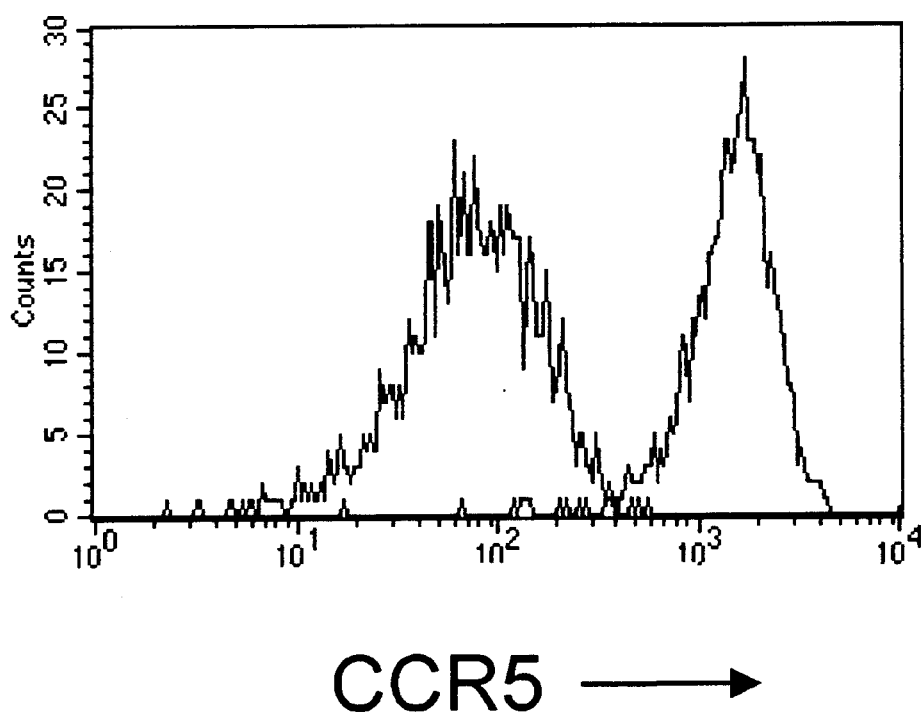
FIG. 9 summarizes data measuring the binding of the αCCR5-αCD3 bispecific antibody to CCR5 on cultured monocytes. Monocytes from a CCR5 positive donor are shown in black, while monocytes from a CCR5 deficient (Δ32/Δ32) donor served as negative control and are shown in white.

Binding of the bispecific single-chain antibody to CHO cells or PBMC was determined by FACS-analysis (FIGS. 7 to 9). The cells were incubated with the bispecific antibody for 60 min on ice followed by an antibody against 6×His (Dianova, Hamburg, Germany) and a PE-conjugated polyclonal rabbit-anti mouse F(ab)2 fragment (R439, Dako, Hamburg, Germany). As the bispecific antibody would also bind to CCR5, an analysis using PBMC that lack expression of CCR5 (due to a homozygous 32 base pair deletion in the CCR5 alleles) was performed. The antibody showed good binding to a subpopulation of lymphocytes. Co-staining with antibodies against CD4 and CD8 identified this subpopulation as CD4 and CD8 positive T lymphocytes (FIG. 7). In addition, the bispecific antibody competed with the monoclonal CD3 antibody OKT-3 for binding to T cells (data not shown).

Binding of the bispecific antibody to CCR5 was demonstrated on CCR5 overexpressing CHO cells and human monocytes (FIGS. 8 and 9). The antibody showed excellent binding to CCR5 transfected CHO cells (FIG. 8) and cultured monocytes (FIG. 9), while no binding was detectable on CHO cells transfected with CXCR4 or on cultured monocytes from a donor with a homozygous CCR5-Δ32/Δ32 deletion. Overnight cultivation of monocytes induces expression of CCR5 on wild-type monocytes, while monocytes from donors with a homozygous CCR5-Δ32/Δ32 deletion fail to express CCR5. Moreover, it was demonstrated that the CCR5 signal detectable with the bispecific antibody on cultured monocytes could be reduced to values below 15% by preincubation of monocytes for 30 min at 37° C. with AOP-RANTES (data not shown) that is known to efficiently induce internalization of CCR5 and reduce binding of CCR5 antibodies (25).

Example 5
Downmodulation of Chemokines Receptors Using an Exemplary Bispecific Antibody of the Invention The following example describes the downmodulation of chemokines receptors using an exemplary bispecific antibody of the invention.

5.1 Downmodulation of CCR5 With mAb MC-1 Against CCR5

Figure 10:
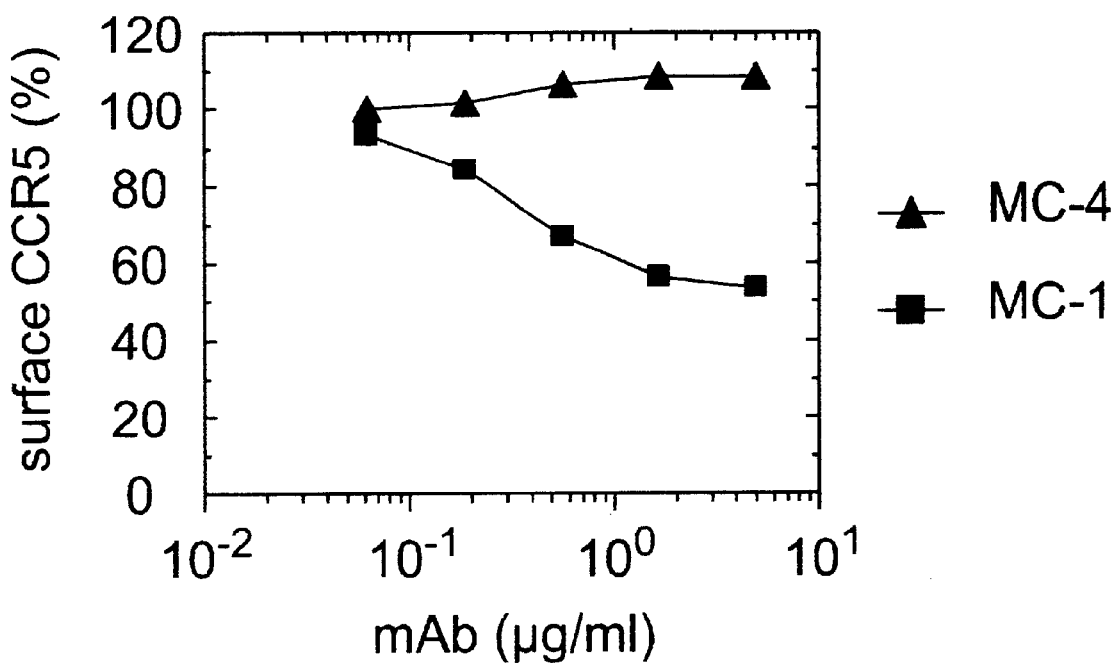
FIG. 10 summarizes data measuring the binding of CCR5 specific monoclonal antibodies to compare their ability to induce downmodulation of CCR5, as analyzed by FACS. MAb MC-1 (squares), the parental antibody of the αCCR5-αCD3 bispecific antibody, showed significant internalization, while MC-4 (triangle) showed no induction of CCR5 internalization. CHO-CCR5 cells were incubated with various concentrations for 30 min at 37° C.

The effect of MC-1 one on the surface expression of human CCR5 was measured. For comparison a different monoclonal antibody MC-4 against CCR5 was used. CHO-CCR5 cells were incubated with various concentrations of antibody MC-1 and MC-4 for 30 min. at 37° C. Cells were placed on ice and stained with MC-1 and MC-4 respectively at a concentration of 15 ug/ml for one hour on ice, followed by detection with a secondary antibody (rabbit anti-mouse FITC, F313 from DAKO). Analysis was performed on a FACSCalibur. Incubation with MC-1 at 37° C. for 30 min resulted in a downmodulation of human CCR5 by 40% at a concentration of 10 ug/ml (FIG. 10).

5.2 Downmodulation of CCR5 By Chemokine-Toxin

Figure 11:
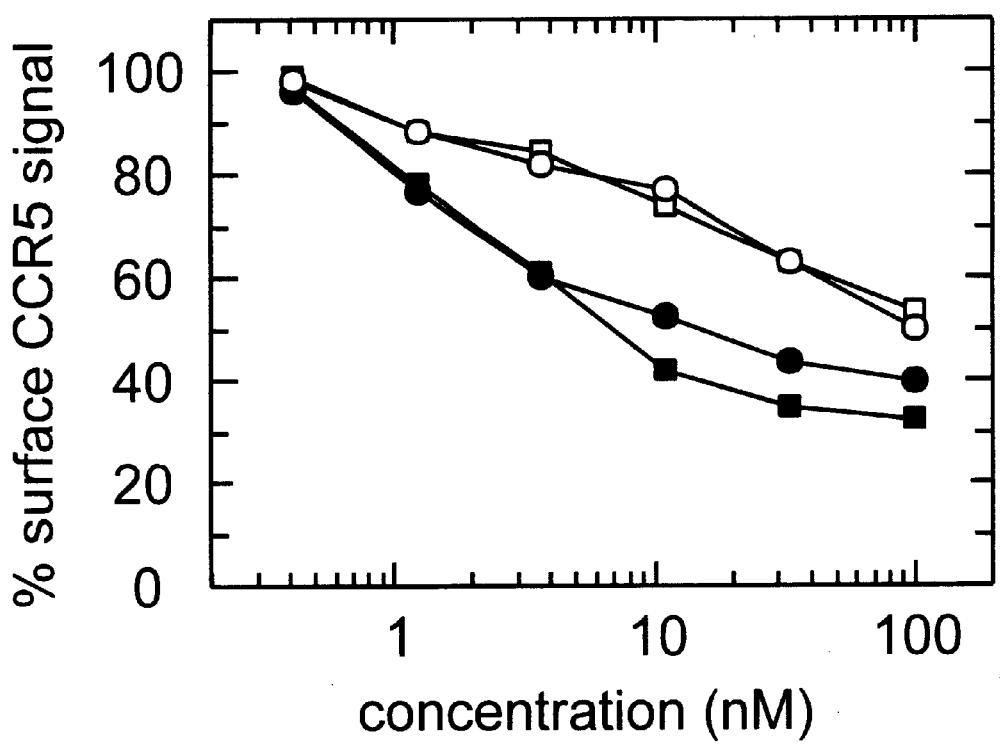
FIG. 11 summarizes data measuring the downmodulation of CCR5 from the surface of PBMC with RANTES-PE38 (open symbols) and RANTES (closed symbols). Surface expression of CCR5 was determined on lymphocytes (squares) and monocytes (circles) and is given as % of the medium control. The fusion protein RANTES-PE38 is able to downmodulate CCR5 from the cell surface with a somewhat lower efficiency than unmodified RANTES.

The fusion of RANTES to the N-terminus of a truncated version of the Pseudomonas exotoxin A is supposed to result in specific binding of the construct to cells expressing RANTES receptors such as CCR5, CCR1 and CCR3. Internalization of the chemokine receptors upon binding of the modified toxin would enhance the cellular uptake and cytotoxic activity of the construct (FIG. 5 lower panel). Therefore, it was analyzed whether RANTES-PE38 is able to internalize CCR5 from the surface of primary monocytes and T cells (FIG. 11, open symbols). Internalization of CCR5 would indicate that the construct is able to bind to CCR5 and that RANTES remains functionally active after fusion to PE38. As shown in FIG. 11 the construct is able to internalize CCR5 from the surface of monocytes and lymphocytes. Unmodified RANTES served as positive control and was somewhat more efficient than RANTES-PE38 (FIG. 11, closed symbols).

PBMC were incubated for 30 min at 37° C. with various concentrations of RANTES or RANTES-PE38 diluted in RPMI with 10% FCS in a volume of 100 μl. Medium alone was used as control. The cells were then stained on ice for surface CCR5 expression using the monoclonal antibody MC-1 or medium as negative control followed by the PE-conjugated anti-mouse antibody R439. The FACS-analysis was performed on a FACSCalibur™ (Becton Dickinson) and CellQuest™ software. Lymphocytes and monocytes were distinguished by their forward and sideward light scatter properties and expression of CD14, CD4 and CD8. Relative surface CCR5 expression was calculated as [mean channel fluorescence (exp.)–mean channel fluorescence (negative control)]/[mean channel fluorescence (medium)–mean channel fluorescence (negative control)].

Example 6
Depletion of Cells with the Exemplary Chimeric Polypeptide: Bispecific CCR5xCD3 Antibody and RANTES-PE38

The following example describes the depletion of cells with the exemplary bispecific chimeric polypeptide of the invention comprising the bispecific CCR5xCD3 antibody and RANTES-PE38.

6.1 CCR5 Specific Depletion of Monocytes from Cultured PBMCs

PBMC from CCR5-wildtype (WT) or CCR5 deficient (Δ32/Δ32) donors were incubated over night to induce expression of CCR5 on monocytes. Cultured PBMC were incubated with different concentrations of purified αCCR5-αCD3 bispecific antibodies or medium as control for 20 h. Surviving cells were analyzed on a FACSCalibur and counted.

Figure 12:
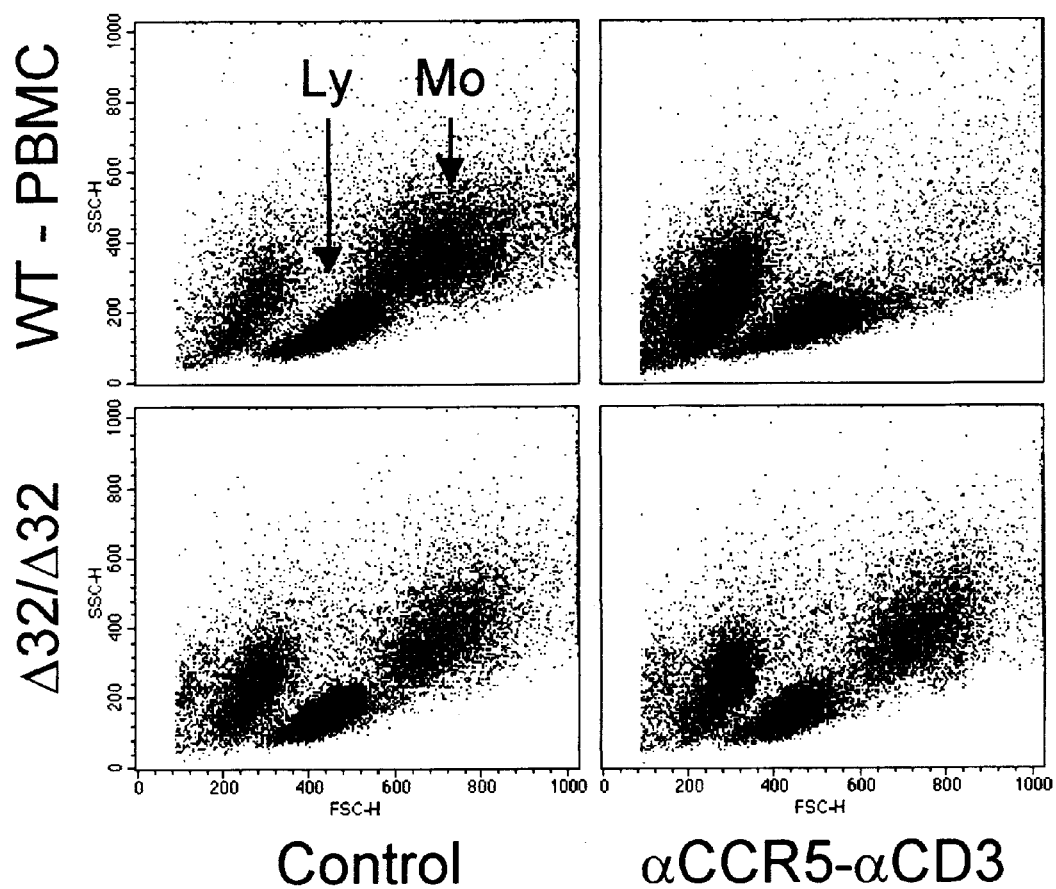
FIG. 12 shows data measuring depletion of CCR5 positive monocytes by a bispecific antibody of the invention. CCR5 deficient PBMC (Δ32/Δ32) or wildtype PBMC (WT-PBMC) were cultured overnight and incubated with the bispecific antibody (100 ng/ml) or medium as control for 20 hours (h). Remaining monocytes (Mo) and lymphocytes (Ly) were identified by their light scatter properties in FACS. The CCR5 positive wildtype monocytes were completely depleted by the bispecific antibody, while the CCR5 deficient monocytes survived.
Figure 13:
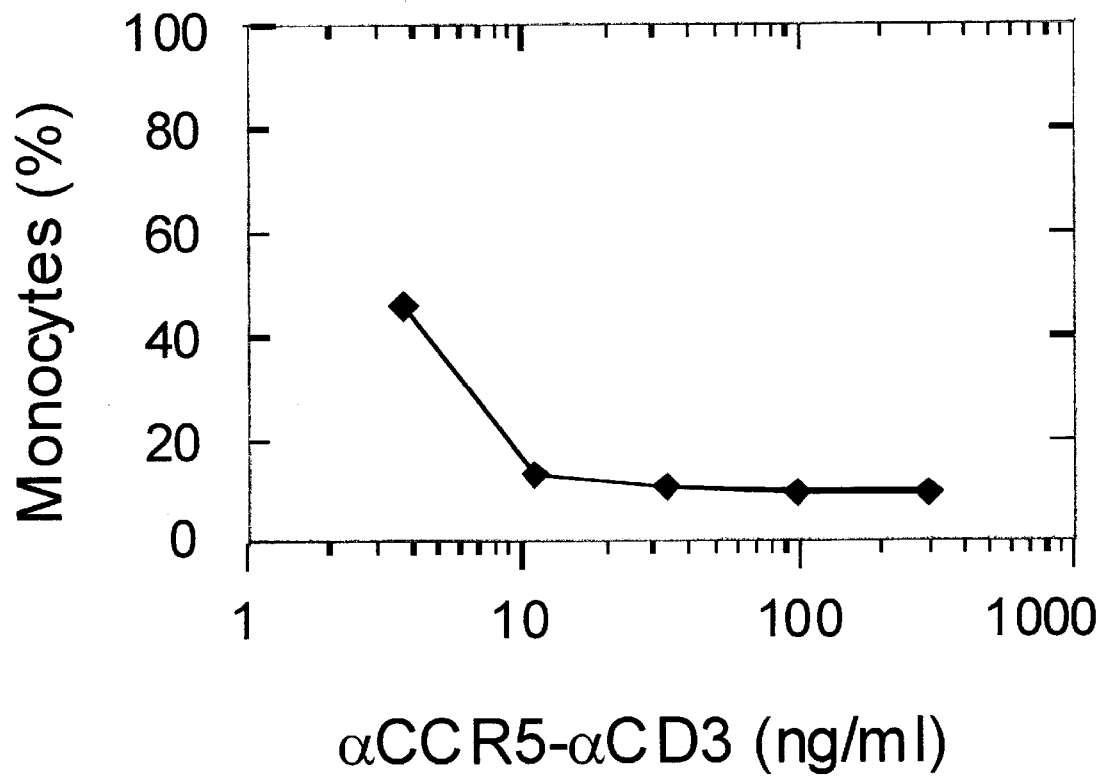
FIG. 13 summarizes data measuring depletion of CCR5 positive monocytes by a bispecific antibody of the invention. Dose response showing depletion of cultured monocytes with various concentrations of the αCCR5-αCD3 bispecific antibody. More than 90% of monocytes were depleted at a concentration of 33 ng/ml.

In order to test the ability of the αCCR5-αCD3 bispecific single-chain antibody to deplete CCR5 positive primary cells, human PBMC were incubated with the antibody (FIG. 12). Prior to incubation the PBMC were cultured overnight to upregulate CCR5 expression on monocytes. By retargeting cytotoxic T cells the bispecific antibody depleted the majority of monocytes within 20 h in a concentration dependent manner (FIG. 13) with an almost complete elimination of CCR5 positive cells at concentration of 10 ng/ml. To verify that the depletion of monocytes was due to their induced expression of CCR5, the same experiment was performed with PBMC from a donor with a homozygous 32 bp deletion in the CCR5 allele that prevents surface expression of CCR5. No depletion of CCR5 deficient monocytes was detectable after 20 h, indicating that the depletion of cells with the bispecific antibody is restricted to monocytes that express CCR5 (FIG. 12), compare lower right panel to upper right panel, left panels serve as negative controls. Monocytes (Mo) and lymphocytes (Ly) were identified by their forward and sidewards light scatter properties. Monocytes appear in the lower left quadrant see arrows.

6.2 Depletion of Monocytes and T Lymphocytes from the Synovial Fluid of Patients with Arthritis Freshly drawn synovial fluid of patients with arthritis were incubated with different concentrations of purified αCCR5-αCD3 bispecific antibodies or medium as control for 20 h. Surviving cells were analyzed on a FACSCalibur™ and counted.

The bispecific single-chain antibody could potentially be applied to deplete CCR5 positive T cells and monocytes from the inflamed joints of patients with arthritis. Therefore, the depletion of CCR5 positive cells from the synovial fluid of patients with various types of arthritis was determined. It was shown previously that the majority of T cells and monocytes in the inflamed synovial fluid express CCR5

(Mack (1999) loc. cit.). In synovial samples obtained before depletion experiments, it was confirmed by FACS analysis that the majority of lymphocytes and monocytes express CCR5, while no expression of CCR5 was detectable on granulocytes (data not shown).

Figure 14:
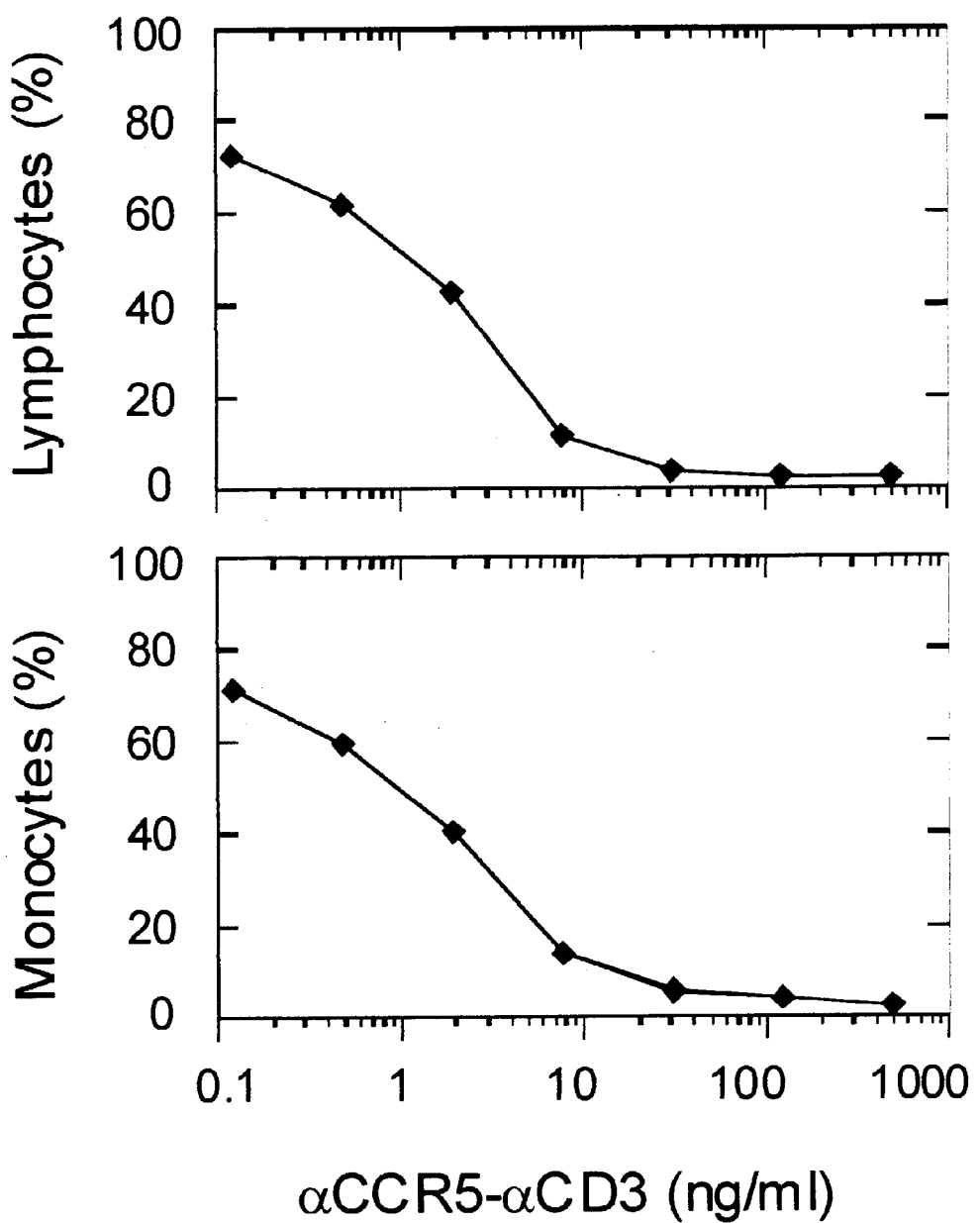
FIG. 14 summarizes data measuring depletion of lymphocytes and monocytes from the synovial fluid of a patient with chronic arthritis by the bispecific αCCR5-αCD3 antibody of the invention. Freshly draw synovial fluid was incubated with various concentrations of the bispecific antibody or medium as control for 20 h and analyzed by FACS. More than 95% of both cell types were depleted at a concentration of 31 ng/ml.
Figure 15:
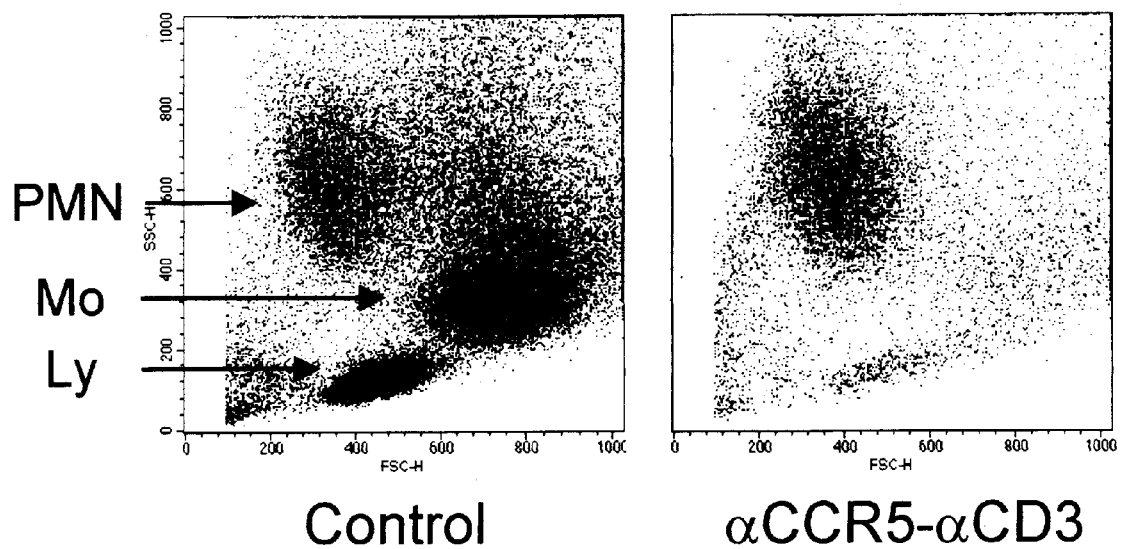
FIG. 15 shows data measuring depletion of lymphocytes and monocytes from the synovial fluid of a patient with chronic arthritis by the bispecific αCCR5-αCD3 antibody of the invention, as measured by FACS analysis. Freshly draw synovial fluid was incubated with the bispecific antibody (500 ng/ml) or medium as control for 20 h and analyzed by FACS (forward and sideward light scatter analysis). The bispecific antibody completely depleted the CCR5 positive monocytes and lymphocytes, while the CCR5 negative granulocytes (PMN) survived. Consistent with our previous data all monocytes and lymphocytes in this synovial fluid expressed CCR5, while no expression of CCR5 was found on granulocytes (PMN).

For the depletion experiments the synovial fluid was incubated ex vivo with different concentrations of the bispecific antibody for 20 h (FIG. 14). The synovial fluid was incubated immediately after puncture without any preparation to ensure that the conditions in vitro resemble most closely the situation in vivo when the antibody would be present within inflamed joints. As shown in FIG. 14 the bispecific antibody induced a depletion of the majority of lymphocytes and monocytes from the synovial fluid, while granulocytes that do not express CCR5 remained unaffected. A representative FACS analysis of the depletion of monocytes and lymphocytes in synovial fluid at a concentration of 0.5 ug/ml CCR5xCD3 is shown in FIG. 15. Only the CCR5 negative neutrophils (PMN: polymorpho-nuclear cells) are unaffected by the bispecific antibody.

The chimeric antibodies were incubated with synovial fluid for one or several days. After 24 hours, the CCR5 positive lymphocytes and monocytes have already almost disappeared. When the medium is controlled after longer incubation, the monocytes have differentiated into macrophages which are visible at the bottom of the culture flask. After an appropriate incubation with the bispecific antibody, no macrophages are visible.

A corresponding result can be obtained when cultivated PBMC are incubated with the bispecific antibody as described above. In this case, there is an almost complete depletion of CCR5 positive monocytes and an almost complete depletion of CCR5 positive T-lymphocytes. The depletion of CCR5 positive T-cells and monocytes is shown in FIG. 15. The results show that the construct of the present invention is capable of destroying CCR5 positive monocytes. This applies to both monocytes from the joint aspirate and blood monocytes which express CCR5 when being differentiated into macrophages. Depletion of the monocytes/macrophages takes place within a few hours (<24 hrs). In particular, the depletion of monocytes/macrophages in the joint is of great advantage in therapy since it is these cells that are mainly responsible for the joint destruction. Moreover, for the activation of T-lymphocytes an interaction with macrophages is also required so that, at the same time, the function of the T-lymphocytes is suppressed. In addition to the depletion of monocytes/macrophages, a considerable reduction in the number of CCR5 positive T-lymphocytes could be observed.

6.3 Comparison of the Efficacy of the Exemplary Bispecific Antibody CCR5xCD3 Versus Monoclonal Antibodies The efficacy of the exemplary αCCR5-αCD3 bispecific single-chain antibody in depleting CCR5 positive monocytes was compared with the efficacy of two unmodified monoclonal antibodies. PBMC from two different donors (F and N) were cultured overnight and then incubated for 24 h with medium, the bispecific single-chain antibody (125 ng/ml), MC-1 (5 µg/ml) and MC-5 (5 µg/ml). The monoclonal antibody MC-1, the parental antibody for the bispecific single-chain antibody has the isotype mouse IgG-1 and the antibody MC-5 has the isotype IgG-2a. The cells were completely recovered and analyzed by FACS to quantify surviving monocytes and lymphocytes.

Figure 16:
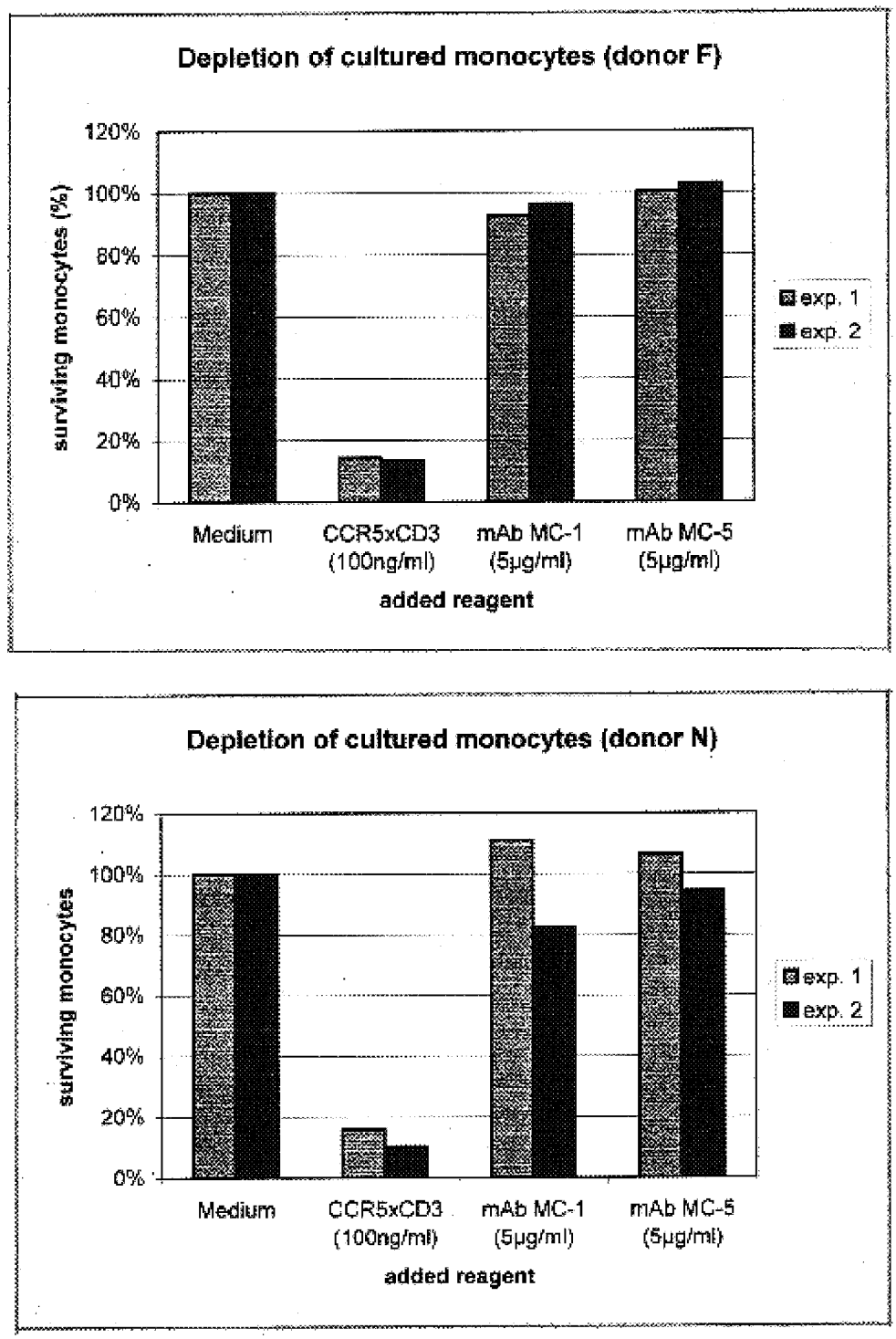
FIG. 16 summarizes data measuring the efficacy of the αCCR5-αCD3 bispecific single-chain antibody of the invention in depleting CCR5 positive monocytes, the antibody was compared with the efficacy of two unmodified monoclonal antibodies MC-1 and MC-5. PBMC from two different donors (F and N) were cultured overnight and then incubated for 24 h with medium in the presence or absence of antibody construct and antibody. Concentrations were as indicated. The cells were completely recovered and analyzed by FACS to quantify surviving monocytes and lymphocytes. Shown are the results of two experiments per PBMC donor. Surprisingly only the bispecific antibody was able to considerably deplete CCR5 positive monocytes, while the unmodified monoclonal antibodies were largely ineffective.
Figure 17:
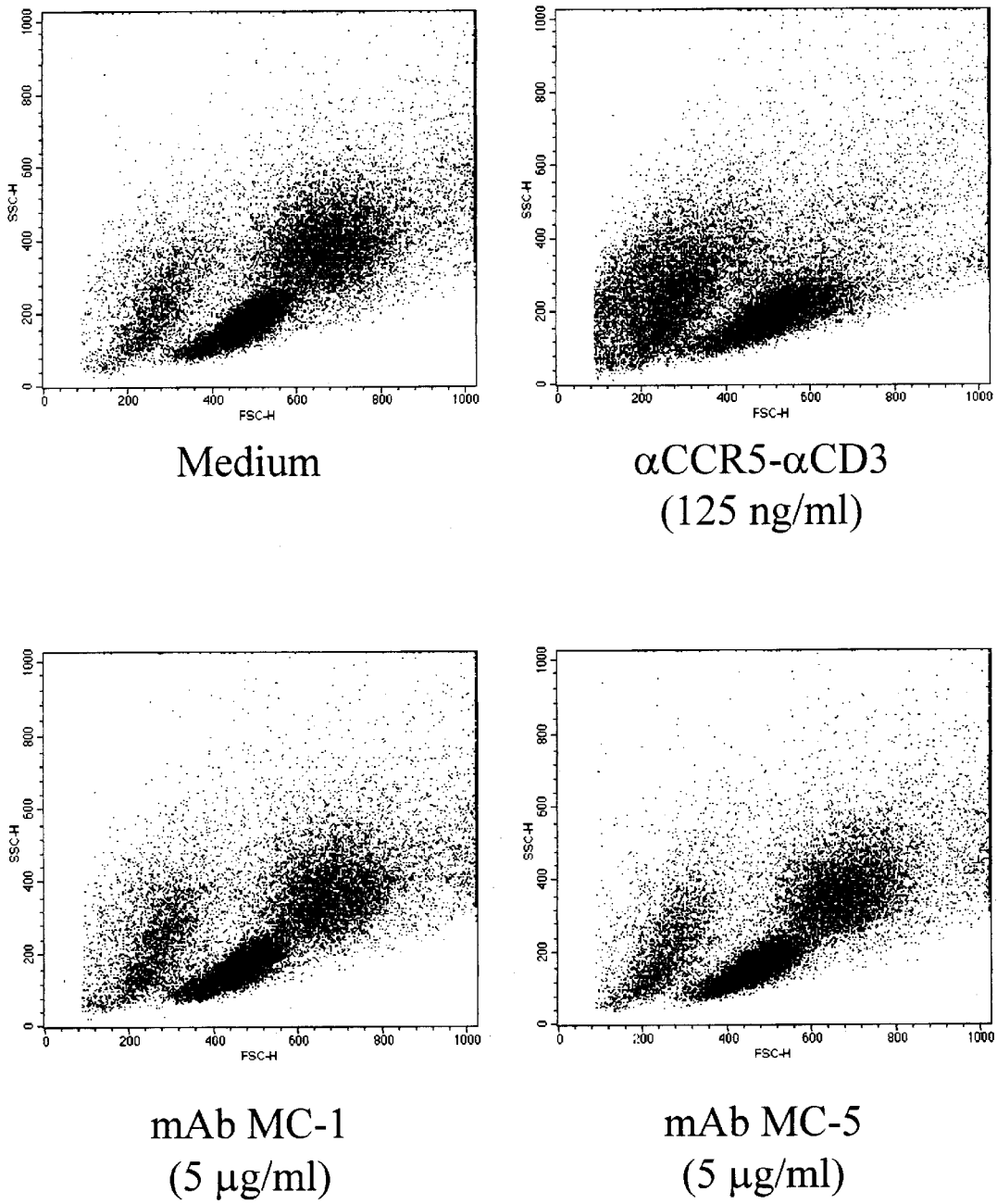
FIG. 17 shows examples of the forward and sideward light scatter analysis of a representative experiment as shown in FIG. 16, indicating that only the αCCR5-αCD3 bispecific single-chain antibody of the invention was capable of depleting the monocytes in the left lower quadrants. For comparison of the localization of different cell types also see FIG. 12 left panel.

FIG. 16 shows that surprisingly only the bispecific antibody was able to considerably deplete CCR5 positive monocytes, while the unmodified monoclonal antibodies were largely ineffective, even when used in a 40 fold excess over the bispecific antibody CCR5xCD3. By FACS analysis using forward and sideward light scatter properties of lymphocytes and monocytes demonstrates that only the CCR5xCD3 bispecific antibody, but not the monoclonal antibodies are capable of depleting cultured monocytes (FIG. 17 compare right upper panel to lower panels).

6.4 Depletion of Chemokine Receptor Expressing Cells With RANTES-PE38

CHO cells expressing CCR5 or CXCR4 were grown to subconfluence on 24 well culture plates and incubated with different concentrations of purified RANTES-PE38 or medium as control. After 40 hours the adherent and non-adherent cells were recovered and analyzed by FACS to measure the percentage of dead cells. It was previously established that dead (propidium iodide positive) CHO cells can be identified by their light scatter properties.

Figure 18:
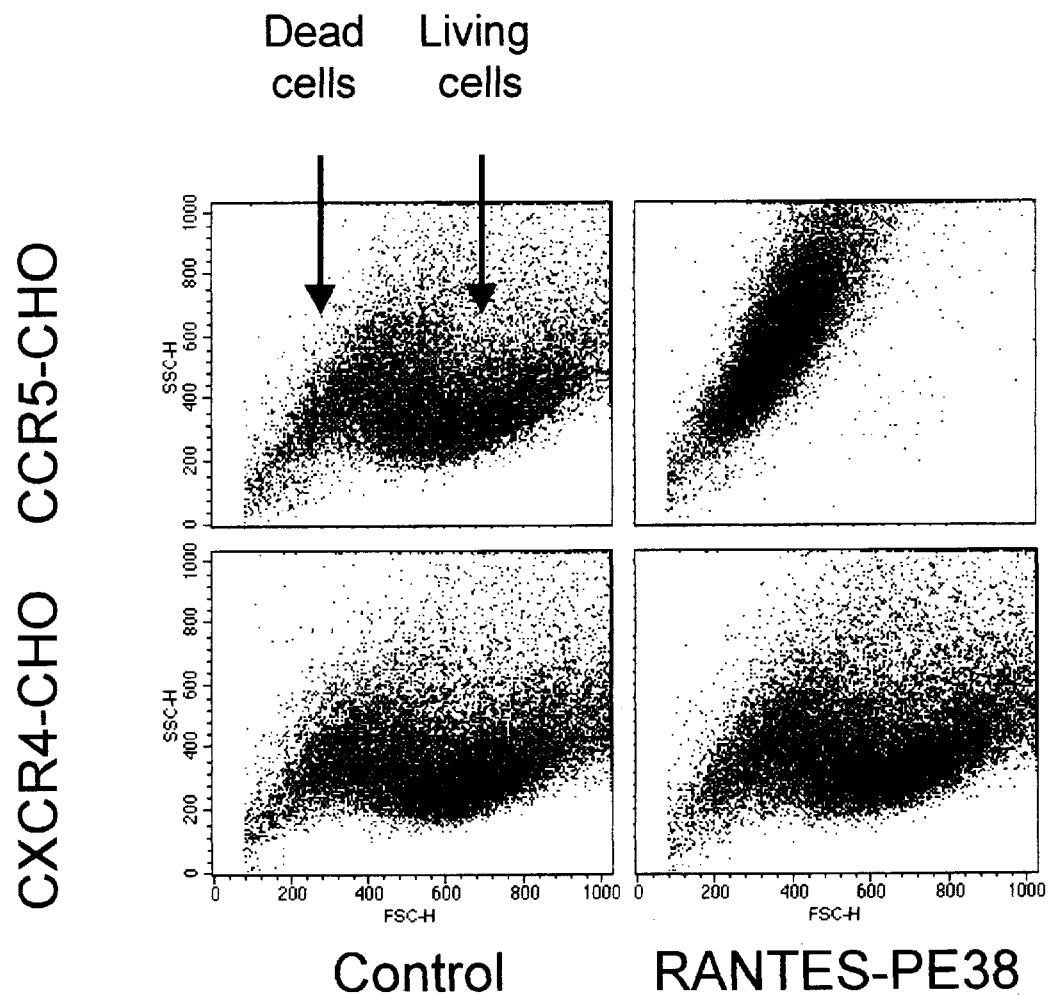
FIG. 18 shows FACS data demonstrating the destruction of CCR5 positive CHO cells with the chemokine-toxin of the invention, RANTES-PE38. CCR5 positive CHO cells and CXCR4 positive CHO cells were incubated for 40 h with the chemokine-toxin (10 nM) and analyzed by FACS. Dead cells appear in the left upper region of the forward and sideward light scatter plot. RANTES-PE38 completely destroyed the CCR5 positive CHO cells while it had no effect on the CXCR4 positive CHO cells.
Figure 19:
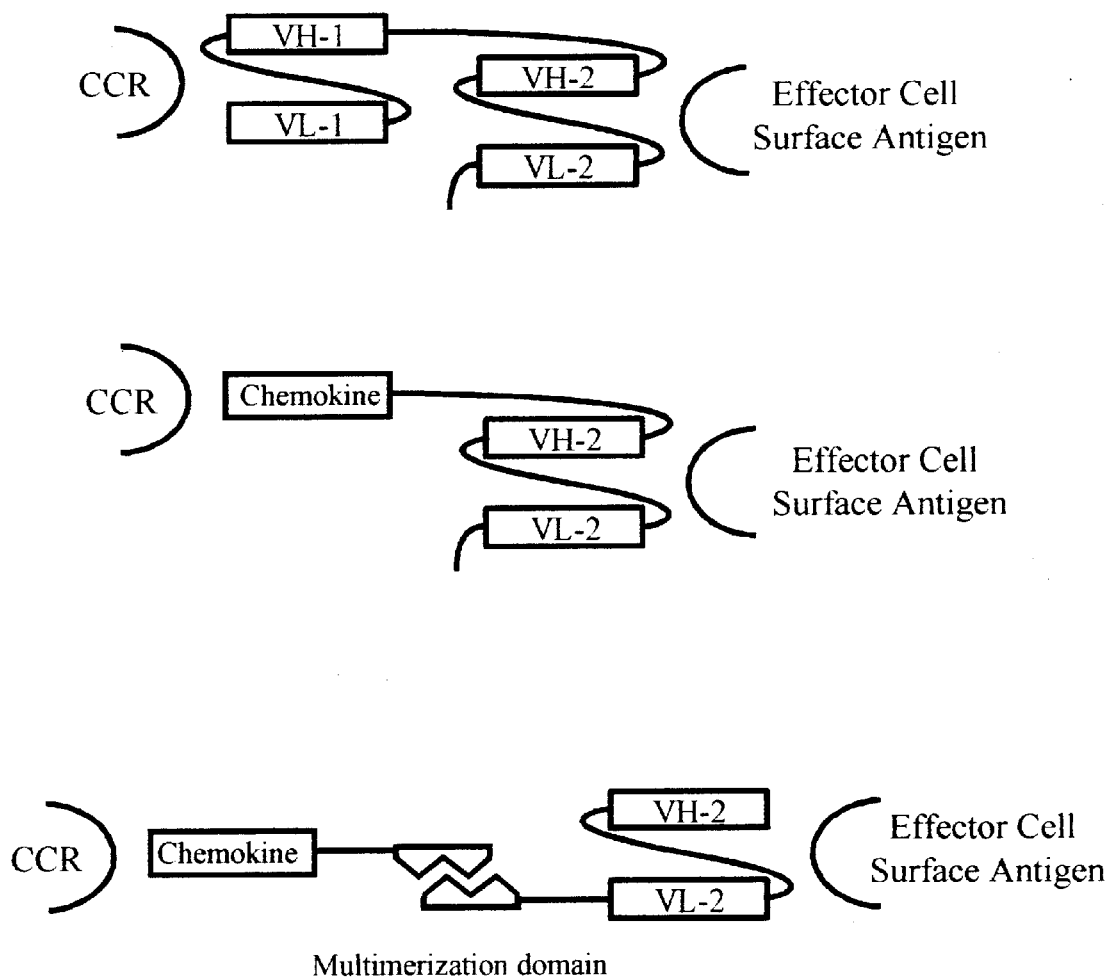
FIGS. 19A, 19B, 19C are a schematic of exemplary antibody and/or chemokine constructs of the invention binding to chemokine receptor (CCR) expressing cells that are combined by peptide linkage or by multimerization domains: (A) shows various examples of antibody and chemokine constructs that interact with an effector cell by binding to an effector cell surface antigen, (B) shows examples of antibody and chemokine constructs that are linked to a toxin, (C) shows examples of antibody and chemokine constructs, that contain an antibody binding site for a toxin.
Figure 19:
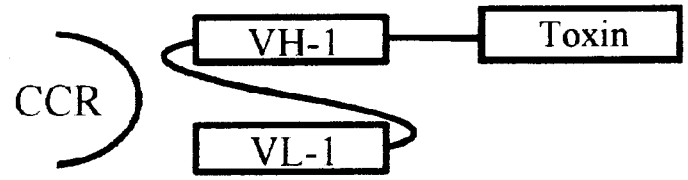
Figure 19:
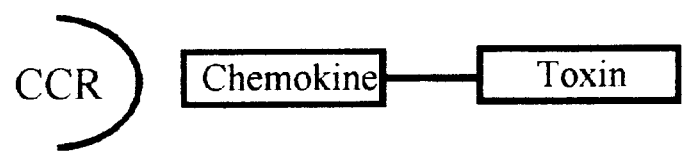
Figure 19:
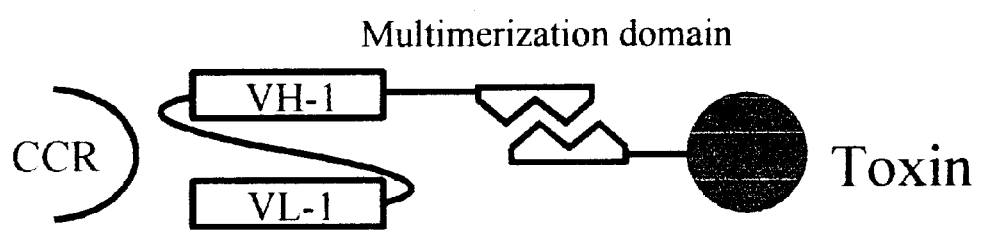

The cytotoxic activity of RANTES-PE38 was further analyzed. For that purpose, CHO cells expressing human CCR5, murine CCR5 and human CXCR4 were incubated with various concentrations of the chemokine-toxin or medium. No surviving (adherent) human or murine CCR5 positive CHO cells were detectable by light microscopy after 40 h incubation with as little as 10 nM RANTES-PE38. In contrast, regular growth and survival was observed when the CCR5 positive cells were incubated with medium or when CXCR4 positive CHO cells were incubated with equal concentrations of the chemokine-toxin (data not shown). To quantify the percentage of dead cells, the adherent and non-adherent cells were analyzed by FACS. It was previously established that living and dead CHO cells can be identified by their light scatter properties, the position of dead and alive cells is indicated by arrows (FIG. 18). As shown in FIG. 18 no cytotoxic effect of RANTES-PE38 was seen on CHO cells expressing CXCR4, while CHO cells expressing human CCR5 were completely killed by 10 nM RANTES-PE38.

These experiments show that RANTES-PE 38 is able to internalize CCR5 from the surface of cells and induces depletion of cells expressing the RANTES receptors hCCR5 or mCCR5. The inactivity of the construct against CXCR4 positive CHO cells demonstrates that the cytotoxic activity of the construct is restricted to cells that express specific chemokine receptors.

Example 7

Viral Infection Assay With Stably Transfected Cells

The following example describes a virus infection assay with stably transfected cells.

GHOST 34 CCR5 cells were derived from HOS/CD4 cells stably expressing CCR5 and were provided by Dan Littman (Skirball Institute, New York). 2.5×104 cells in 48-well trays were exposed to 100 µl of chemokine at appropriate dilution for 30 min at 37° C. 100 µl of the NSI, CCR5-dependent HIV-1 strain, SF162 was added at 1000 focus forming units/ml (FFU/ml) and the cells incubated for a further 3 h. The cells were then washed and incubated in medium containing the appropriate chemokine for 4 days before fixing, staining in situ for p24 production and estimating foci of infection as previously described.

TABLE I

Nucleosidal Reverse Transcriptase Inhibitors (nucleoside analogs, NRTI)

| Substance | Trade-name | Dosing Schedule | Common Side Effects and General Remarks |
|---|---|---|---|
| Zidovudine (AZT) | Retrovir | 300 mg, 2x daily | Initial gastrointestinal (GI) side effects, anemia, neutropenia, myopathy |
| Lamivudine (3TC) | Epivir | 150 mg, 2x daily | Generally well tolerated. Effective against hepatitis |
| Zidovudine, Lamiduvine (AZT + 3TC) | Combivir | 1 tablet 2x daily | Combination-tablet containing 300 mg AZT and 150 mg 3TC |
| Didanosine (ddI) | Videx | 200 mg, 2x daily or 400 mg, 1x daily on an empty stomach (>60 kg weight) | 15% peripheral neuropathy, pancreatitis; avoid alcohol. Contents alcohol: could be given simultaneously with all NRTIs, Adefovir, Nevirapine, and Efavirence; Delavirdine and Indinavir should be given at least 1 hour before ddI; Nelfinavir to be given 1 hour after ddI. |
| Zalcitabine (ddC) | Hivid | 0.375–0.75 mg, 3x daily | 17–31% peripheral neuropathy in different studies; aphteous ulcerations |
| Stavudine (d4T) | Zerit | 20–40 mg, 2x daily | Peripheral neuropathy (1–4% in earlier studies; 24% in 'expanded access' patients with CD4 > 50) |
| Abacavir (ABA) | Ziagen | 300 mg, 2x daily | About 3% reaction for hypersensitivity: fever, indisposition, possibly transient rash, gastrointestinal side effects. |

TABLE II

Protease Inhibitors

| Substance | Trade-name | Dosing Schedule | Common Side Effects and General Remarks |
|---|---|---|---|
| Saquinavir (hard gelatine capsule, SQV-H) | Invirase | 600 mg, 3x daily, take with high-fat meal | Well tolerated. Limited efficacy due to poor resorption. |
| Saquinavir (soft gelatine capsule, SQV-S) | Fortovase | 1200 mg, 3x daily, take with high-fat meal (>28 g) | Improved resorption compared to Invirase. |
| Ritonavir (RTV) | Norvir | 600 mg, (6 cap./7.5 ml) 2x daily. Start with 300 mg, 2x daily, then increase within 10 days to 600 mg, 2x daily; | Nausea and numb lips for up to 5 weeks. Occasionally hepatitis. Not tolerated by up to 50% of the patients. |
| Indinavir (IDV) | Crixivan | 800 mg, every 8 hours on an empty stomach or with snack (<2 g fat) | Neural calculus with 6–8%; requires large liquid intake. Occasionally nausea and gastrointestinal side effects. |
| Nelfinavir (NFV) | Viracept | 750 mg, 3x daily, or 1250 mg, 2x daily with meals | Often diarrhea, sometimes nausea. |

TABLE III

Non-Nucleosidal Reverse Transcriptase Inhibitors (NNRTI)

| Substance | Trade-name | Dosing Schedule | Common Side Effects and General Remarks |
|---|---|---|---|
| Nevirapine (NVP) | Viramune | 200 mg, 1x daily | Transient skin, hepatitis, induced liver enzymes P450 3A4 |
| Delavirdine (DLV) | Rescriptor | 400 mg, 3x daily | Transient skin, suppresses P450 3A4 |
| Efavirence (EFV) | Sustiva | 600 mg, 1x daily in the evening | Initially dizziness, insomnia, momentary transient skin: Induces P450 3A4; avoid Claritithromycin. |

TABLE IV

Chemokine receptors and chemokine ligands

| Chemokine Receptors | Chemokine Ligands |
|---|---|
| CXCR3 | I-TAC (CXCL11), IP-10 (CXCL-10), Mig (CXCL9) |
| CXCR4 | SDF-1 (CXCL12) |
| CXCR5 | BCA1 (CXCL13) |
| CXCR6 | CXCL76 |
| CCR1 | MIP1alpha (CCL3), RANTES (CCL5), MCP-3 (CCL7), MCP-4 (CCL13), HCC1 (CCL14), LKN1 (CCL15) |
| CCR2 | MCP-1 (CCL2), MCP-2 (CCL8), MCP-3 (CCL7), MCP-4 (CCL13) |
| CCR3 | RANTES (CCL5), MCP-2 (CCL8), MCP-3 (CCL7), MCP-4 (CCL13), eotaxin (CCL11), LKN1 (CCL15), MPIF-2 (CCL24), eotaxin-3 (CCL26) |
| CCR4 | TARC (CCL17), MDC (CCL22) |
| CCR5 | MIP1alpha (CCL3), MIP1 beta (CCL4), RANTES (CCL5), MCP-2 (CCL8), MCP-3 (CCL7), MCP-4 (CCL13), eotaxin (CCL11) |
| CCR6 | LARC (CCL20) |
| CCR7 | ELC (CCL19), SLC (CCL21) |
| CCR8 | I-309 (CCL1), MIP1 beta (CCL4), TARC (CCL17) |
| CCR9 | TECK (CCL25) |
| XCR1 | XCL1, XCL2 |
| CCR10 | CTACK (CCL27), MEC |

Example 8
Concentration Dependent Binding of CCR5xCD3 To CCR5 Expressing CHO Cells The following example describes the concentration dependent binding of the bispecific scFv CCR5xCD3 to CCR5-expressing CHO cells.

Chinese hamster ovary cells stably transfected with CCR5 (CCR5+CHO) were used as target cells for binding studies of bispecific scFv CCR5xCD3 (as described in Example 2 and FIG. 3). These cells were negative for CD3 and >95% positive for CCR5 as evaluated by binding assays with the parental antibody MC-1 (as described in Example 5 and FIG. 10). Binding was evaluated by a flow cytometry based binding assay.

$4 \times 10^5$ CCR5+CHO cells were resuspended in 50 µl FACS buffer (PBS with 1% fetal calf serum (FCS) and 0.05% sodium azide) containing different dilutions of scFV CCR5xCD3 ranging from 20 µg/ml to 19.5 ng/ml.

Figure 20:
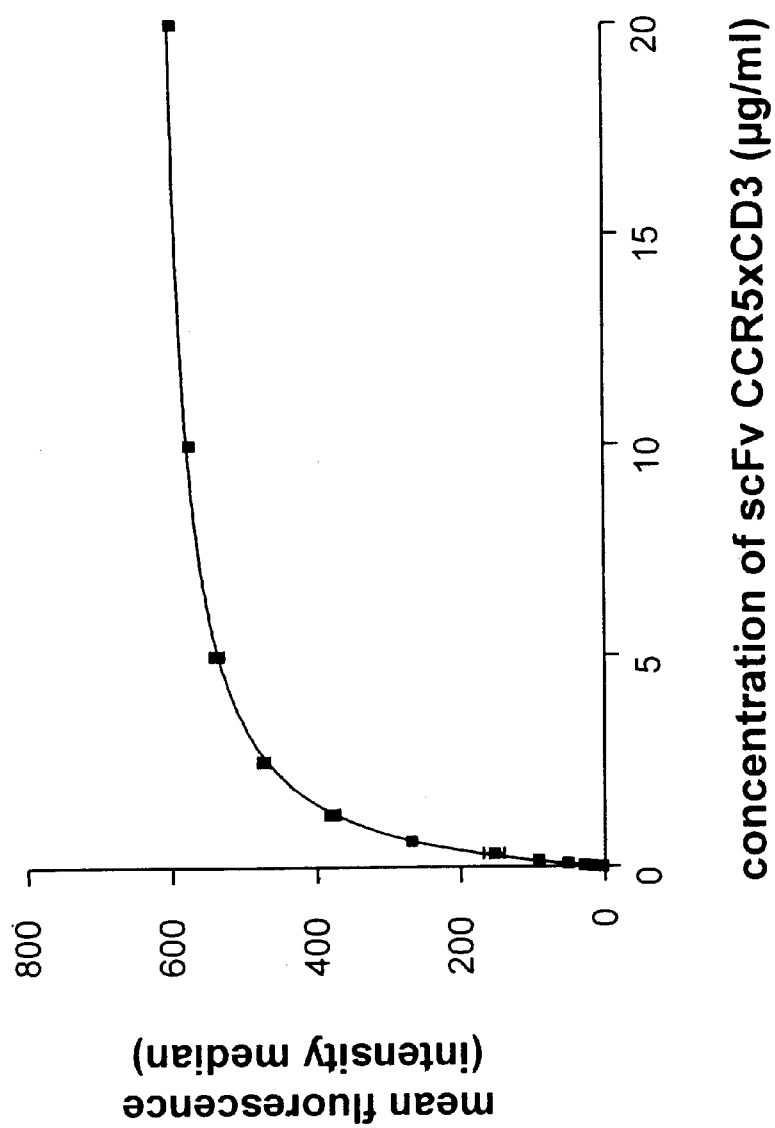
FIG. 20 graphically summarizes data showing the concentration dependent binding of scFv CCR5xCD3 to CCR5 expressing CHO cells, as described in detail in Example 8, below.

4×10⁵ CCR5+CHO cells were incubated with 19.5 ng/ml scFV CCR5xCD3 for 30 minutes at 4° C. after washing cells were incubated for 45 minutes at 4° C. with 20 µg/ml anti-His-Tag monoclonal antibody. In FIG. 20, cells were incubated in a 96 well microtiter plate for 30 minutes at 4° C. Cells were washed twice with FACS buffer and incubated for 45 minutes at 4° C. with 20 µg/ml anti-His-Tag monoclonal antibody (Dianova GmbH, Hamburg). Specifically bound scFV CCR5xCD3 was detected with a monoclonal goat anti-mouse IgG F(ab')2-PE conjugated antibody (Dianova). After washing, the cells were analyzed in a flow cytometer (FACSCalibur™, Becton Dickinson) using the CellQuest™ software (Becton Dickinson, Franklin Lakes, N.J.) to calculate the median values of the fluorescence intensities of the different concentration samples. Nonlinear regression analysis was performed with GraphPad Prizm™ (Version 3.02) (San Diego, Calif.). Concentration dependent binding of scFv CCR5xCD3 to CCR5 expressing CHO cells was observed with a $K_D$ value of 0.86 µg/ml (FIG. 20).

Example 9

Cytotoxic Activity of CCR5xCD3 With Primary T Lymphocytes as Effector Cells

The following example demonstrates the cytotoxic activity of the scFv CCR5xCD3 with primary T lymphocytes as effector cells; and, that no cytotoxic effect of scFv CCR5xCD3 was observed using CXCR4+CHO cells as target cells.

The capacity of scFv CCR5xCD3 (as described in Example 2 and FIG. 3) to mediate cytotoxicity to CCR5-positive cells was tested using stably transfected CCR5+CHO as target cells and CD3 positive T-lymphocytes derived from peripheral blood as effector cells. For detection of cytotoxicity, a FACS based assay was performed.

CD3+ T-cells (include CD4+ and CD8+ cells) were isolated from peripheral blood by negative selection using a human T cell enrichment column (R&D Systems, Minneapolis, Minn.). For this purpose, PBMC were prepared by standard Ficoll-Hypaque density gradient separation and applied to the column. B cells and monocytes were bound to the column matrix, while T cells were eluted. The enriched T cells were washed in medium and used as effector cells.

For discrimination of target cells from effector cells by flow cytometry, CCR5+CHO cells were labeled with the aliphatic membrane dye PKH26 (Sigma, St. Louis, Mo.) in a final concentration of 12 µM. 0.5×10⁵ labeled CCR5+CHO cells and 2.5×10⁵ CD3+ T-cells were seeded in a 96-well microtiter plate in a effector:target ratio of 5:1. 100 µl dilutions of scFv CCR5xCD3 ranging from 320 ng/ml to 0.3 pg/ml were incubated with the cells for 16 hours at 37° C. in a humified atmosphere at 5% $CO_2$. Subsequently cells were centrifuged for 3 minutes at 600×g, and the cell pellets were resuspended in 200 µl FACS buffer (PBS, 1% FCS, 0.05% sodium azide). After staining with 1 µg/ml propidium iodine (PI), cells were analyzed in duplicate in a flow cytometer (FACSCalibur™, Becton Dickinson).

The cytotoxic activity of scFv CCR5xCD3 was tested in a FACS based assay with CCR5+CHO as target and CD3+ T-lymphocytes as effector cells. CD3+ T-cells were isolated from peripheral blood. CCR5+CHO cells were labeled with 12 µM PKH26. Effector:target cells in a ratio of 5:1 were incubated with dilutions of scFv CCR5xCD3 ranging from 320 ng/ml to 0.3 pg/ml for 16 hours at 37° C. and 5% $CO_2$. After staining with 1 µg/ml propidium iodine (PI), cells were analyzed by flow cytometry.

In order to verify the specificity of scFv CCR5xCD3 mediated lysis, stably CXCR4 transfected CHO cells were used as negative control target cells. The cytotoxicity assay was performed under identical conditions as described for CCR5+CHO cells.

Figure 21:
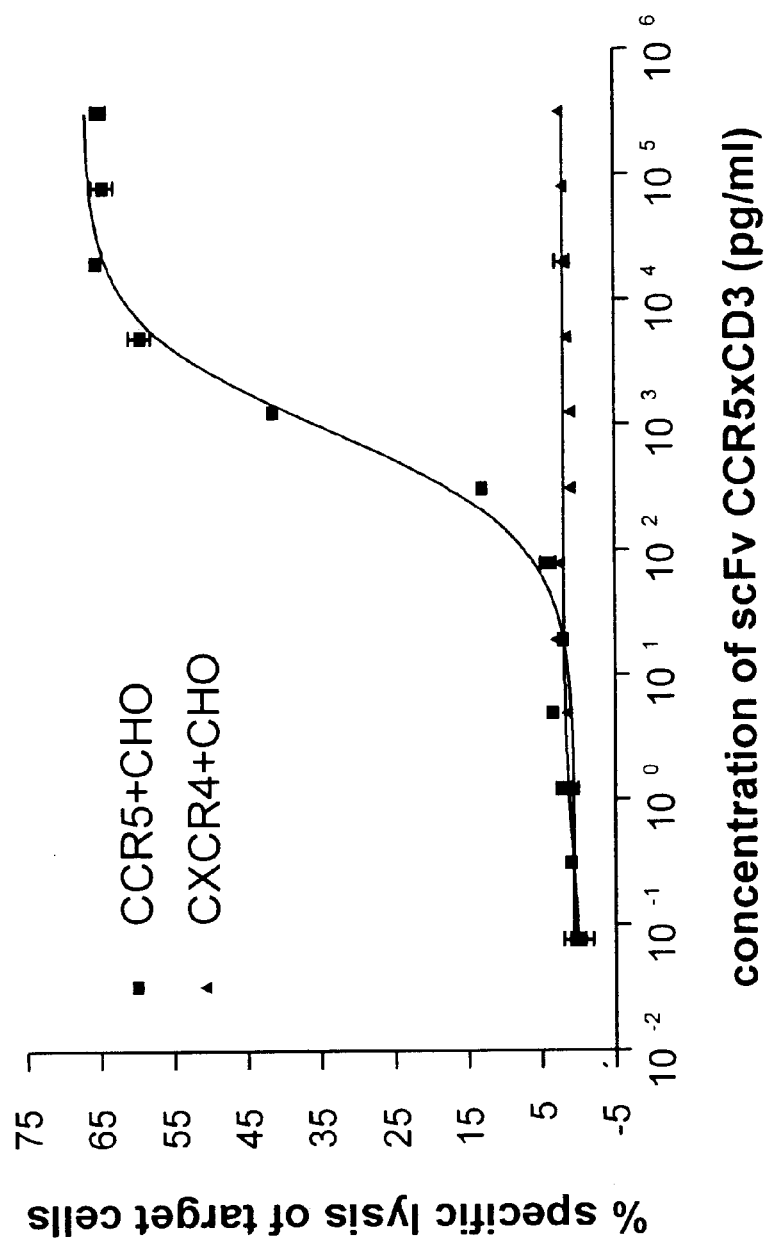
FIG. 21 graphically summarizes data as a dose response curve showing the specific lysis of CCR5+CHO cells with primary T lymphocytes as effector cells, as described in detail in Example 9, below.

Specific lysis of CCR5+CHO cells was calculated using the CellQuest™ software (Becton Dickinson) and a nonlinear regression analysis was performed with GraphPad Prizm. A sigmoidal dose response curve was obtained (FIG. 21) revealing an EC50 value of 912 pg/ml. No cytotoxic effect of scFv CCR5xCD3 was observed using CXCR4+ CHO cells as target cells.

Example 10

Cytotoxic Activity of CCR5xCD3 With T Cell Clones as Effector Cells

This example demonstrates the cytotoxic activity of scFv CCR5xCD3 with the T cell clone CB15 as effector cells; and, that specific lysis mediated by scFv CCR5xCD3 is not restricted to the cytotoxic activity of CD8+CTL but that CD4+ T cells are also involved in this process. The cytotoxic activity of scFv CCR5xCD3 on CCR5-positive cells was tested using the CD3 positive T-cell line CB15 as effector cells in a FACS based assay.

The cytotoxic activity of scFv CCR5xCD3 (as described in Example 2 and FIG. 3) on CCR5-positive cells was also tested using the CD3 positive T-cell line CB15 (CD4+) as effector cells. For detection of cytotoxicity, a FACS based assay was performed with CCR5 transfected CHO cells (CCR5+CHO) as target cells.

CCR5+CHO target cells labeled with 10 µM PKH26 were used in a effector:target ratio of 10:1. CCR5+CHO cells were labeled with the aliphatic membrane dye PKH26 (Sigma) in a final concentration of 10 µM. Effector and target cells were incubated in a microtiter plate in a ratio of 10:1 with 100 µl of scFv CCR5xCD3 in dilutions ranging from 40 µg/ml to 0.15 ng/ml for 6 hours at 37° C. in a humified atmosphere with 5% $CO_2$. Cells were centrifuged for 3 minutes at 600×g and the cell pellets were resuspended in 200 µl FACS buffer (PBS, 1% FCS, 0.05% sodium azide). Cells were stained with 1 µg/ml propidium iodine (PI) and analyzed in duplicate in a flow cytometer (FACSCalibur™, Becton Dickinson).

Figure 22:
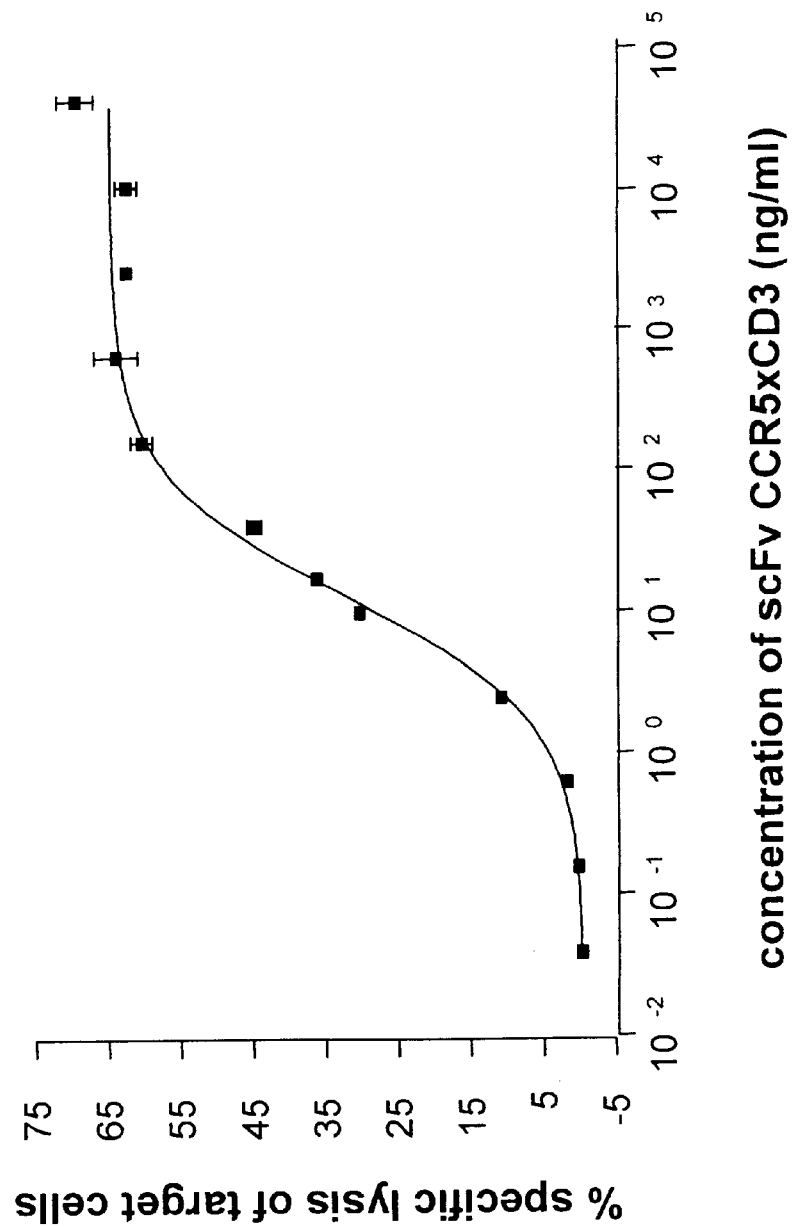
FIG. 22 graphically summarizes data demonstrating the cytotoxic activity of scFv CCR5xCD3 with the T cell clone CB15 as effector cells, as described in detail in Example 10, below.

Specific lysis of CCR5+CHO cells was calculated using the CellQuest™ software (Becton Dickinson) and a nonlinear regression analysis was performed with GraphPad Prizm™. A sigmoidal dose response curve was obtained (FIG. 22) revealing an EC50 value of 12.8 ng/ml.

The results obtained with T cell clone CB15 as effector cells in bioactivity assay demonstrate that specific lysis mediated by scFv CCR5xCD3 is not restricted to the cytotoxic activity of CD8+CTL but that CD4+ T cells are also involved in this process.

Example 11

Epitope Mapping of Parental CCR5 Specific Monoclonal Antibody MC-1

The following example describes the epitope mapping of parental CCR5 specific monoclonal antibody MC-1 used for construction of scFv CCR5xCD3. These data show that the epitope recognized by MC-1 is specific for human CCR5 and that lysine at position aa (amino acid residue) 171 and isoleucine at position aa 198 in human CCR5 sequence are essential for this specificity.

Epitope of parental CCR5 specific monoclonal antibody (Mab) MC-1 used for construction of scFv CCR5xCD3 (as described in Example 2 and FIG. 3) was mapped by flow cytometry using a panel of about 70 CHO-K1 cell lines stably expressing chimeric and point mutant receptors (Samson, J. Biol. Chem., 1997, 272, 24934–24941; Lee, J. Biol. Chem., 1999, 274, 9617–9626; Blanpain, J. Biol. Chem., 1999, 274, 34719–34727; Blanpain, Blood, 2000, 96, 1638–1645). Cells were incubated for 30 min on ice with Mab MC-1, washed and stained with PE-conjugated anti-mouse Ig antibody (Sigma). CHO-K1 cells expressing CCR2b were used as negative control. MC-1 was shown to recognize the first part of the second extracellular loop (ECL2) of the CCR5 molecule. ECL2 ranges from aa 168–199; RSQ KEGLHYTCSS HFPYSQYQFW KNFQTLKIV (SEQ ID NO: 35) and is located between the transmembrane regions 4 and 5 of CCR5 as described by Chen, J. Virol., 1997, 71, 2705–2714.

The amino acid sequences of human and rhesus macaque CCR5 differ in eight amino acids with two amino acid changes are situated at position aa 171 (K-->R) and aa 198 (I-->M) in the ECL2 (Chen, J. Virol., 1997, 71, 2705–2714). Due to these amino acid changes, potential cross-reactivity of MC-1 with the ECL2 of rhesus macaque CCR5 was analyzed with human and rhesus PBMCs in a FACS based assay. PBMC of both species were isolated by standard Ficoll gradient centrifugation. $5 \times 10^5$ cells were suspended in 50 µl FACS buffer and 50 µg/ml of MC-1 was added. After 30 min incubation at 4° C., the cells were washed and stained with goat anti-mouse IgG F(ab')2-PE conjugated monoclonal antibody (Dianova) for 30 min at 4° C. in the dark. Cells were washed and analyzed in a flow cytometer (FACSCalibur™, Becton Dickinson).

Figure 23:
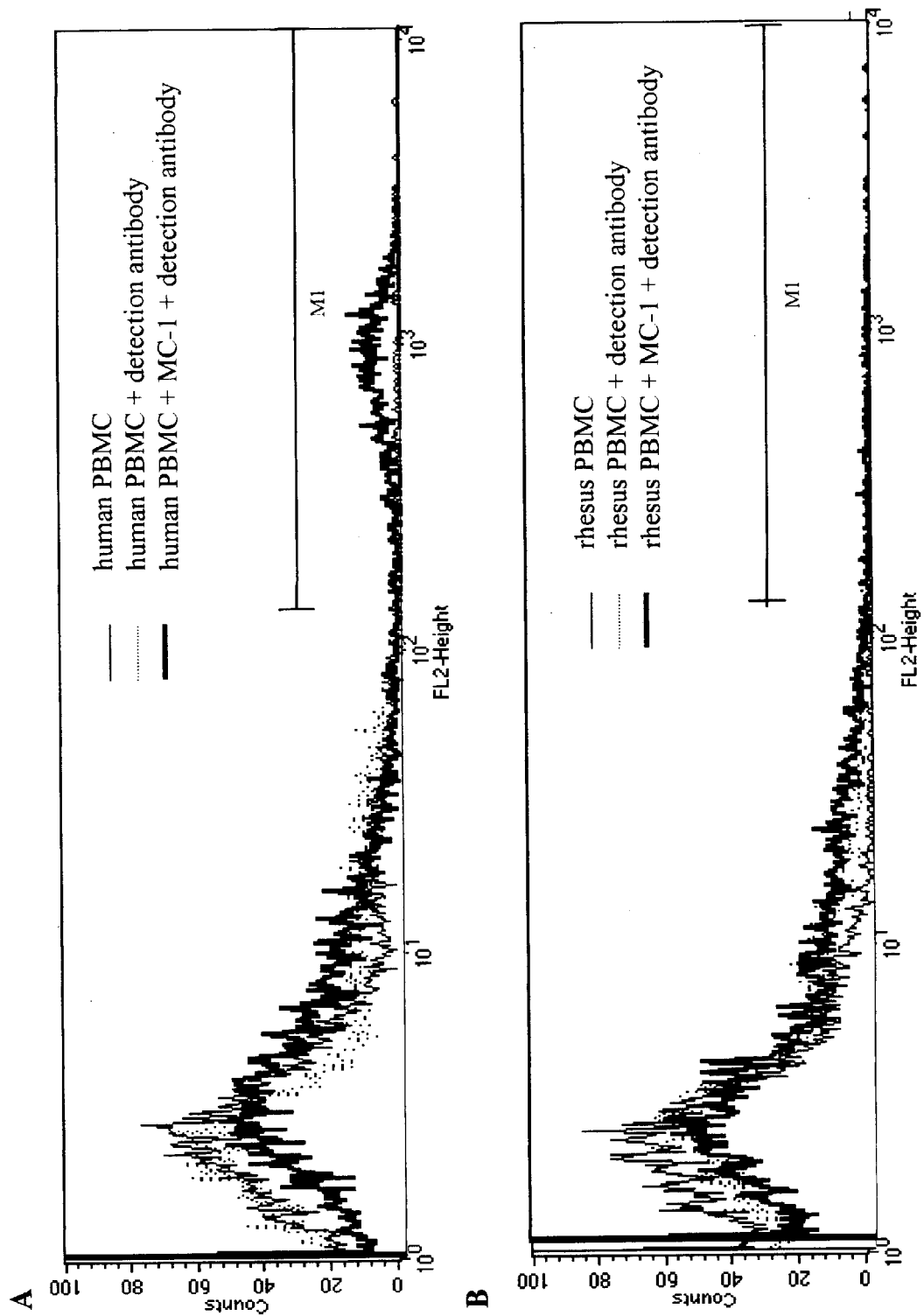
FIG. 23 graphically summarizes data demonstrating that the Mab MC-1 exclusively bound to human CCR5 but did not react with CCR5 derived from rhesus macaques, as described in detail in Example 11, below.

In FIG. 23, reactivity of MC-1 with A) human PBMC and B) rhesus PBMC. PBMC (solid line), PBMC with PE conjugated goat anti-mouse antibody (dotted line) and PBMC with MC-1 and PE conjugated goat anti-mouse antibody (solid bold line). Binding of MC-1 to human PBMC (A), but not to rhesus PBMC (B) is indicated by the M1 marker line.

As shown in FIG. 23 MC-1 exclusively bound to human CCR5 but did not react with CCR5 derived from rhesus macaques. These data show that the epitope recognized by MC-1 is specific for human CCR5 and that lysine at position aa 171 and isoleucine at position aa 198 in human CCR5 sequence are essential for this specificity. Especially lysine at position aa 171 which is located in the first part of ECL2 contributes to the specific recognition of the human epitope of CCR5 by Mab MC-1.

Example 12 scFv CCR5xCD3 Mediated Reduction of Virus Production in HIV-1 Infected Monocytes The following example demonstrates the scFv CCR5xCD3 mediated reduction of virus production in HIV-1 infected monocytes.

Peripheral blood mononuclear cells (PBMC) were prepared from fresh buffy coats of healthy donors by Ficoll density centrifugation and monocytes were isolated by over night adherence to culture flasks. Remaining PBL were removed and cultured separately at 37° C. in a humidified atmosphere at 5% $CO_2$.

Monocytes were seeded into a 48 well microtiter plate at a density of $5 \times 10^4$ cells/well and infected with the M-tropic HIV-1 strain BaL (moi=1) overnight at 37° C. in a humidified atmosphere at 5% $CO_2$. The virus was removed by washing and the monocytes were further cultured with unstimulated PBL ($15 \times 10^4$ per well)+scFv CCR5xCD3 (1 µg/ml)+AZT (75 µM) or with unstimulated PBL ($15 \times 10^4$ per well) alone as negative control. 5 days post infection (p.i.) monocytes were washed and cultured in the absence of AZT or antibody. Supernatant was harvested on day 15 p.i. and HIV-1 replication was quantified by measurement of p24 in an ELISA. This demonstrates that the scFv CCR5xCD3 of the invention led to a reduction of virus replication of 75% in samples containing scFV CCR5xCD3 (75 ng/ml p24) compared to the control without scFv CCR5xCD3 (300 ng/ml p24).

A number of embodiments of the invention have been described. Nevertheless, it will be understood that various modifications may be made without departing from the spirit and scope of the invention. Accordingly, other embodiments are within the scope of the following claims.

What is claimed is:

1. A bispecific antibody comprising a first antigen binding domain that specifically binds to a chemokine receptor; and, a second antigen binding domain that specifically binds to a CD3 antigen wherein the bispecific antibody comprises an amino acid sequence encoded by a nucleic acid as set forth in SEQ ID NO: 17, or, the bispecific antibody comprises an amino acid sequence as set forth in SEQ ID NO: 18.

2. The bispecific antibody of claim 1, wherein the bispecific antibody is a single chain antibody construct.

3. The bispecific antibody of claim 1, wherein the single chain antibody construct comprises a $V_L$ and a $V_H$ domain capable of specifically binding the chemokine receptor and a $V_H$ and a $V_L$ domain capable of specifically binding a T cell surface polypeptide.

4. The bispecific antibody of claim 1, wherein the antigen binding domain that specifically binds to a chemokine receptor comprises a murine anti-human CCR5 antibody MC-1 or MC-5.

5. The bispecific antibody of claim 1, further comprising a cell toxin.

6. The bispecific antibody of claim 5, wherein the bispecific antibody is covalently bound to the cell toxin.

7. The bispecific antibody of claim 1, further comprising a second antibody that binds to a a cell toxin.

8. A method of making a chimeric composition that can specifically bind to a chemokine receptor and a CD3 antigen comprising the following steps:

providing a first polypeptide comprising at least one moiety that specifically binds to a chemokine receptor and a second polypeptide comprising at least one moiety that specifically binds to a CD3 antigen;

contacting the first polypeptide with the second polypeptide in vitro or in vivo under conditions wherein the first polypeptide specifically binds to the second polypeptide, wherein the chimeric composition comprises an amino acid sequence encoded by a nucleic acid as set forth in SEQ ID NO:17, or the chimeric composition comprises an amino acid sequence as set forth in SEQ ID NO: 18.

9. The method of claim 8, further comprising a cell toxin.

10. The method of claim 9, wherein the cell toxin is a truncated Pseudomonas exotoxin A (PE38).

11. A method for making a bispecific antibody comprising providing a nucleic acid as set forth in SEQ ID NO: 17, or, a nucleic acid encoding an amino acid sequence as set forth in SEQ ID NO: 18; and expressing the nucleic acid, thereby making the bispecific antibody.

* * * * *

SEQUENCE LISTING

<160> NUMBER OF SEQ ID NOS: 34

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 1
ggaacaagat ggattatcaa gtgtc                                    25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 2
ctgtgtatga aaactaagcc atgtg                                    25

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 3
tttaccagat ctcaaaaaga ag                                              22

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 4
ggagaaggac aatgttgtag g                                               21

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 5
gacattcagc tgacccagtc tcca                                            24

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 6
gttttatttc cagcttggtc cc                                              22

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 7
accatgggat ggagctgtgt catgctctt                                       29

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 8
tgaggagacg gtgaccgtgg tcccttggcc ccag                                 34

<210> SEQ ID NO 9
<211> LENGTH: 322
<212> TYPE: DNA
<213> ORGANISM: Mus sp.
<220> FEATURE:
<221> NAME/KEY: CDS

<222> LOCATION: (1)..(321)

<400> SEQUENCE: 9

```
gac att cag ctg acc cag tct cca gcc tcc cta tct gca tct gtg gga      48
Asp Ile Gln Leu Thr Gln Ser Pro Ala Ser Leu Ser Ala Ser Val Gly
1               5                   10                  15 gaa act gtc acc atc aca tgt cga gca agt gag aat att tac agt tat      96
Glu Thr Val Thr Ile Thr Cys Arg Ala Ser Glu Asn Ile Tyr Ser Tyr
            20                  25                  30 tta gca tgg tat cag cag aaa cag gga aaa tct cct caa ctc ctg gtc     144
Leu Ala Trp Tyr Gln Gln Lys Gln Gly Lys Ser Pro Gln Leu Leu Val
        35                  40                  45 tat aat gca aaa acc tta aca gaa ggt gtg cca tca agg ttc agt ggc     192
Tyr Asn Ala Lys Thr Leu Thr Glu Gly Val Pro Ser Arg Phe Ser Gly
    50                  55                  60 agt gga tca ggc aca cag ttt tct ctg aag atc aac agc ctg cag cct     240
Ser Gly Ser Gly Thr Gln Phe Ser Leu Lys Ile Asn Ser Leu Gln Pro
65                  70                  75                  80 gaa gat ttt ggg aat tat ttc tgt caa cat cat tat gat act cct cgg     288
Glu Asp Phe Gly Asn Tyr Phe Cys Gln His His Tyr Asp Thr Pro Arg
                85                  90                  95 acg ttc ggt gga ggg acc aag ctg gaa ata aaa c                       322
Thr Phe Gly Gly Gly Thr Lys Leu Glu Ile Lys
                100                 105
```

<210> SEQ ID NO 10
<211> LENGTH: 107
<212> TYPE: PRT
<213> ORGANISM: Mus sp.

<400> SEQUENCE: 10

```
Asp Ile Gln Leu Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Thr Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Asn Tyr Phe Cys Gln His His Tyr Asp Thr Pro Arg
                85                  90                  95

Thr Phe Gly Gly Gly Thr Lys Leu Glu Ile Lys
                100                 105
```

<210> SEQ ID NO 11
<211> LENGTH: 276
<212> TYPE: DNA
<213> ORGANISM: Mus sp.
<220> FEATURE:
<221> NAME/KEY: CDS
<222> LOCATION: (1)..(276)

<400> SEQUENCE: 11

```
gcc tcc cta tct gca tct gtg gga gaa act gtc acc atc aca tgt cga      48
Ala Ser Leu Ser Ala Ser Val Gly Glu Thr Val Thr Ile Thr Cys Arg
1               5                   10                  15 gca agt gag aat att tac agt tat tta gca tgg tat cag cag aaa cag      96
Ala Ser Glu Asn Ile Tyr Ser Tyr Leu Ala Trp Tyr Gln Gln Lys Gln
            20                  25                  30
```

```
gga aaa tct cct caa ctc ctg gtc tat aat gca aaa acc tta aca gaa      144
Gly Lys Ser Pro Gln Leu Leu Val Tyr Asn Ala Lys Thr Leu Thr Glu
         35                  40                  45 ggt gtg cca tca agg ttc agt ggc agt gga tca ggc aca cag ttt tct      192
Gly Val Pro Ser Arg Phe Ser Gly Ser Gly Ser Gly Thr Gln Phe Ser
 50                  55                  60 ctg aag atc aac agc ctg cag cct gaa gat ttt ggg aat tat ttc tgt      240
Leu Lys Ile Asn Ser Leu Gln Pro Glu Asp Phe Gly Asn Tyr Phe Cys
 65                  70                  75                  80 caa cat cat tat gat act cct cgg acg ttc ggt gga                      276
Gln His His Tyr Asp Thr Pro Arg Thr Phe Gly Gly
                 85                  90

<210> SEQ ID NO 12
<211> LENGTH: 92
<212> TYPE: PRT
<213> ORGANISM: Mus sp.

<400> SEQUENCE: 12

Ala Ser Leu Ser Ala Ser Val Gly Glu Thr Val Thr Ile Thr Cys Arg
 1               5                  10                  15

Ala Ser Glu Asn Ile Tyr Ser Tyr Leu Ala Trp Tyr Gln Gln Lys Gln
             20                  25                  30

Gly Lys Ser Pro Gln Leu Leu Val Tyr Asn Ala Lys Thr Leu Thr Glu
         35                  40                  45

Gly Val Pro Ser Arg Phe Ser Gly Ser Gly Ser Gly Thr Gln Phe Ser
 50                  55                  60

Leu Lys Ile Asn Ser Leu Gln Pro Glu Asp Phe Gly Asn Tyr Phe Cys
 65                  70                  75                  80

Gln His His Tyr Asp Thr Pro Arg Thr Phe Gly Gly
                 85                  90

<210> SEQ ID NO 13
<211> LENGTH: 414
<212> TYPE: DNA
<213> ORGANISM: Mus sp.
<220> FEATURE:
<221> NAME/KEY: CDS
<222> LOCATION: (1)..(414)

<400> SEQUENCE: 13 atg gga tgg agc tgt gtc atg ctc ttc ttg gta gca aca gct aca ggt       48
Met Gly Trp Ser Cys Val Met Leu Phe Leu Val Ala Thr Ala Thr Gly
 1               5                  10                  15 gtc cac tcc cag gtc caa ctg cag cag cct ggg gct ggg agg gtg agg       96
Val His Ser Gln Val Gln Leu Gln Gln Pro Gly Ala Gly Arg Val Arg
             20                  25                  30 cct gga gct tca gtg aag ctg tcc tgc aag gct tct ggc tac tcc ttc      144
Pro Gly Ala Ser Val Lys Leu Ser Cys Lys Ala Ser Gly Tyr Ser Phe
         35                  40                  45 acc agt tac tgg atg aac tgg gtg aag cag agg cct gga caa ggc ctt      192
Thr Ser Tyr Trp Met Asn Trp Val Lys Gln Arg Pro Gly Gln Gly Leu
 50                  55                  60 gag tgg att ggc atg att cat cct tcc gat agt gaa act agg tta aat      240
Glu Trp Ile Gly Met Ile His Pro Ser Asp Ser Glu Thr Arg Leu Asn
 65                  70                  75                  80 cag aag ttc aac gac agg gcc aca ttg act gtt gac aaa tat tcc agc      288
Gln Lys Phe Asn Asp Arg Ala Thr Leu Thr Val Asp Lys Tyr Ser Ser
                 85                  90                  95 aca gcc tat ata caa ctc agc agc ccg aca tct gag gac tct gcg gtc      336
```

-continued

```
Thr Ala Tyr Ile Gln Leu Ser Ser Pro Thr Ser Glu Asp Ser Ala Val
            100                 105                 110 tat tac tgt gca aga gga gaa tat tac tac ggt ata ttt gac tac tgg      384
Tyr Tyr Cys Ala Arg Gly Glu Tyr Tyr Tyr Gly Ile Phe Asp Tyr Trp
        115                 120                 125 ggc caa ggg acc acg gtc acc gtc tcc tca                              414
Gly Gln Gly Thr Thr Val Thr Val Ser Ser
    130                 135
```

<210> SEQ ID NO 14
<211> LENGTH: 138
<212> TYPE: PRT
<213> ORGANISM: Mus sp.

<400> SEQUENCE: 14

```
Met Gly Trp Ser Cys Val Met Leu Phe Leu Val Ala Thr Ala Thr Gly
 1               5                  10                  15

Val His Ser Gln Val Gln Leu Gln Gln Pro Gly Ala Gly Arg Val Arg
             20                  25                  30

Pro Gly Ala Ser Val Lys Leu Ser Cys Lys Ala Ser Gly Tyr Ser Phe
         35                  40                  45

Thr Ser Tyr Trp Met Asn Trp Val Lys Gln Arg Pro Gly Gln Gly Leu
     50                  55                  60

Glu Trp Ile Gly Met Ile His Pro Ser Asp Ser Glu Thr Arg Leu Asn
 65                  70                  75                  80

Gln Lys Phe Asn Asp Arg Ala Thr Leu Thr Val Asp Lys Tyr Ser Ser
                 85                  90                  95

Thr Ala Tyr Ile Gln Leu Ser Ser Pro Thr Ser Glu Asp Ser Ala Val
            100                 105                 110

Tyr Tyr Cys Ala Arg Gly Glu Tyr Tyr Tyr Gly Ile Phe Asp Tyr Trp
        115                 120                 125

Gly Gln Gly Thr Thr Val Thr Val Ser Ser
    130                 135
```

<210> SEQ ID NO 15
<211> LENGTH: 354
<212> TYPE: DNA
<213> ORGANISM: Mus sp.
<220> FEATURE:
<221> NAME/KEY: CDS
<222> LOCATION: (2)..(352)

<400> SEQUENCE: 15

```
c ttg gta gca aca gct aca ggt gtc cac tcc cag gtc caa ctg cag cag   49
  Leu Val Ala Thr Ala Thr Gly Val His Ser Gln Val Gln Leu Gln Gln
   1               5                  10                  15 cct ggg gct ggg agg gtg agg cct gga gct tca gtg aag ctg tcc tgc     97
Pro Gly Ala Gly Arg Val Arg Pro Gly Ala Ser Val Lys Leu Ser Cys
             20                  25                  30 aag gct tct ggc tac tcc ttc acc agt tac tgg atg aac tgg gtg aag    145
Lys Ala Ser Gly Tyr Ser Phe Thr Ser Tyr Trp Met Asn Trp Val Lys
         35                  40                  45 cag agg cct gga caa ggc ctt gag tgg att ggc atg att cat cct tcc    193
Gln Arg Pro Gly Gln Gly Leu Glu Trp Ile Gly Met Ile His Pro Ser
     50                  55                  60 gat agt gaa act agg tta aat cag aag ttc aac gac agg gcc aca ttg    241
Asp Ser Glu Thr Arg Leu Asn Gln Lys Phe Asn Asp Arg Ala Thr Leu
 65                  70                  75                  80 act gtt gac aaa tat tcc agc aca gcc tat ata caa ctc agc agc ccg    289
Thr Val Asp Lys Tyr Ser Ser Thr Ala Tyr Ile Gln Leu Ser Ser Pro
```

```
aca tct gag gac tct gcg gtc tat tac tgt gca aga gga gaa tat tac      337
Thr Ser Glu Asp Ser Ala Val Tyr Tyr Cys Ala Arg Gly Glu Tyr Tyr
            100                 105                 110 tac ggt ata ttt gac ta                                                354
Tyr Gly Ile Phe Asp
        115
```

<210> SEQ ID NO 16
<211> LENGTH: 117
<212> TYPE: PRT
<213> ORGANISM: Mus sp.

<400> SEQUENCE: 16

```
Leu Val Ala Thr Ala Thr Gly Val His Ser Gln Val Gln Leu Gln Gln
 1               5                  10                  15

Pro Gly Ala Gly Arg Val Arg Pro Gly Ala Ser Val Lys Leu Ser Cys
            20                  25                  30

Lys Ala Ser Gly Tyr Ser Phe Thr Ser Tyr Trp Met Asn Trp Val Lys
        35                  40                  45

Gln Arg Pro Gly Gln Gly Leu Glu Trp Ile Gly Met Ile His Pro Ser
    50                  55                  60

Asp Ser Glu Thr Arg Leu Asn Gln Lys Phe Asn Asp Arg Ala Thr Leu
65                  70                  75                  80

Thr Val Asp Lys Tyr Ser Ser Thr Ala Tyr Ile Gln Leu Ser Ser Pro
                85                  90                  95

Thr Ser Glu Asp Ser Ala Val Tyr Tyr Cys Ala Arg Gly Glu Tyr Tyr
            100                 105                 110

Tyr Gly Ile Phe Asp
        115
```

<210> SEQ ID NO 17
<211> LENGTH: 1545
<212> TYPE: DNA
<213> ORGANISM: Mus sp.
<220> FEATURE:
<221> NAME/KEY: CDS
<222> LOCATION: (58)..(1545)

<400> SEQUENCE: 17

```
atgggatgga gctgtatcat cctcttcttg gtagcaacag ctacaggtgt acactcc       57 gat atc gtg ctg acc cag tct cca gcc tcc cta tct gca tct gtg gga     105
Asp Ile Val Leu Thr Gln Ser Pro Ala Ser Leu Ser Ala Ser Val Gly
 1               5                  10                  15 gaa act gtc acc atc aca tgt cga gca agt gag aat att tac agt tat     153
Glu Thr Val Thr Ile Thr Cys Arg Ala Ser Glu Asn Ile Tyr Ser Tyr
            20                  25                  30 tta gca tgg tat cag cag aaa cag gga aaa tct cct caa ctc ctg gtc     201
Leu Ala Trp Tyr Gln Gln Lys Gln Gly Lys Ser Pro Gln Leu Leu Val
        35                  40                  45 tat aat gca aaa acc tta aca gaa ggt gtg cca tca agg ttc agt ggc     249
Tyr Asn Ala Lys Thr Leu Thr Glu Gly Val Pro Ser Arg Phe Ser Gly
    50                  55                  60 agt gga tca ggc aca cag ttt tct ctg aag atc aac agc ctg cag cct     297
Ser Gly Ser Gly Thr Gln Phe Ser Leu Lys Ile Asn Ser Leu Gln Pro
65                  70                  75                  80 gaa gat ttt ggg aat tat ttc tgt caa cat cat tat gat act cct cgg     345
Glu Asp Phe Gly Asn Tyr Phe Cys Gln His His Tyr Asp Thr Pro Arg
                85                  90                  95
```

-continued

| | |
|---|---|
| acg ttc ggt gga ggg acc aag ctc gag atc aaa ggt ggt ggt tct<br>Thr Phe Gly Gly Gly Thr Lys Leu Glu Ile Lys Gly Gly Gly Ser<br>100                    105                    110 | 393 |
| ggc ggc ggc ggc tcc ggt ggt ggt ggt tct cag gtc caa ctg cag cag<br>Gly Gly Gly Gly Ser Gly Gly Gly Gly Ser Gln Val Gln Leu Gln Gln<br>       115                    120                    125 | 441 |
| cct ggg gct ggg agg gtg agg cct gga gct tca gtg aag ctg tcc tgc<br>Pro Gly Ala Gly Arg Val Arg Pro Gly Ala Ser Val Lys Leu Ser Cys<br>130                    135                    140 | 489 |
| aag gct tct ggc tac tcc ttc acc agt tac tgg atg aac tgg gtg aag<br>Lys Ala Ser Gly Tyr Ser Phe Thr Ser Tyr Trp Met Asn Trp Val Lys<br>145                    150                    155                    160 | 537 |
| cag agg cct gga caa ggc ctt gag tgg att ggc atg att cat cct tcc<br>Gln Arg Pro Gly Gln Gly Leu Glu Trp Ile Gly Met Ile His Pro Ser<br>                165                    170                    175 | 585 |
| gat agt gaa act agg tta aat cag aag ttc aac gac agg gcc aca ttg<br>Asp Ser Glu Thr Arg Leu Asn Gln Lys Phe Asn Asp Arg Ala Thr Leu<br>            180                    185                    190 | 633 |
| act gtt gac aaa tat tcc agc aca gcc tat ata caa ctc agc agc ccg<br>Thr Val Asp Lys Tyr Ser Ser Thr Ala Tyr Ile Gln Leu Ser Ser Pro<br>            195                    200                    205 | 681 |
| aca tct gag gac tct gcg gtc tat tac tgt gca aga gga gaa tat tac<br>Thr Ser Glu Asp Ser Ala Val Tyr Tyr Cys Ala Arg Gly Glu Tyr Tyr<br>210                    215                    220 | 729 |
| tac ggt ata ttt gac tac tgg ggc caa ggg acc acg gtc acc gtc tcc<br>Tyr Gly Ile Phe Asp Tyr Trp Gly Gln Gly Thr Thr Val Thr Val Ser<br>225                    230                    235                    240 | 777 |
| tcc gga ggt ggt gga tcc gat atc aaa ctg cag cag tca ggg gct gaa<br>Ser Gly Gly Gly Gly Ser Asp Ile Lys Leu Gln Gln Ser Gly Ala Glu<br>                      245                    250                    255 | 825 |
| ctg gca aga cct ggg gcc tca gtg aag atg tcc tgc aag act tct ggc<br>Leu Ala Arg Pro Gly Ala Ser Val Lys Met Ser Cys Lys Thr Ser Gly<br>            260                    265                    270 | 873 |
| tac acc ttt act agg tac acg atg cac tgg gta aaa cag agg cct gga<br>Tyr Thr Phe Thr Arg Tyr Thr Met His Trp Val Lys Gln Arg Pro Gly<br>275                    280                    285 | 921 |
| cag ggt ctg gaa tgg att gga tac att aat cct agc cgt ggt tat act<br>Gln Gly Leu Glu Trp Ile Gly Tyr Ile Asn Pro Ser Arg Gly Tyr Thr<br>290                    295                    300 | 969 |
| aat tac aat cag aag ttc aag gac aag gcc aca ttg act aca gac aaa<br>Asn Tyr Asn Gln Lys Phe Lys Asp Lys Ala Thr Leu Thr Thr Asp Lys<br>305                    310                    315                    320 | 1017 |
| tcc tcc agc aca gcc tac atg caa ctg agc agc ctg aca tct gag gac<br>Ser Ser Ser Thr Ala Tyr Met Gln Leu Ser Ser Leu Thr Ser Glu Asp<br>                    325                    330                    335 | 1065 |
| tct gca gtc tat tac tgt gca aga tat tat gat gat cat tac tgc ctt<br>Ser Ala Val Tyr Tyr Cys Ala Arg Tyr Tyr Asp Asp His Tyr Cys Leu<br>            340                    345                    350 | 1113 |
| gac tac tgg cgc caa ggc acc act ctc aca gtc tcc tca gtc gaa ggt<br>Asp Tyr Trp Arg Gln Gly Thr Thr Leu Thr Val Ser Ser Val Glu Gly<br>355                    360                    365 | 1161 |
| gga agt gga ggt tct ggt gga agt gga ggt tca ggt gga gtc gac gac<br>Gly Ser Gly Gly Ser Gly Gly Ser Gly Gly Ser Gly Gly Val Asp Asp<br>370                    375                    380 | 1209 |
| att cag ctg acc cag tct cca gca atc atg tct gca tct cca ggg gag<br>Ile Gln Leu Thr Gln Ser Pro Ala Ile Met Ser Ala Ser Pro Gly Glu<br>385                    390                    395                    400 | 1257 |
| aag gtc acc atg acc tgc aga gcc agt tca agt gta agt tac atg aac<br>Lys Val Thr Met Thr Cys Arg Ala Ser Ser Ser Val Ser Tyr Met Asn<br>                    405                    410                    415 | 1305 |

-continued

```
tgg tac cag cag aag tca ggc acc tcc ccc aaa aga tgg att tat gac    1353
Trp Tyr Gln Gln Lys Ser Gly Thr Ser Pro Lys Arg Trp Ile Tyr Asp
            420                 425                 430 aca tcc aaa gtg gct tct gga gtc cct tat cgc ttc agt ggc agt ggg    1401
Thr Ser Lys Val Ala Ser Gly Val Pro Tyr Arg Phe Ser Gly Ser Gly
        435                 440                 445 tct ggg acc tca tac tct ctc aca atc agc agc atg gag gct gaa gat    1449
Ser Gly Thr Ser Tyr Ser Leu Thr Ile Ser Ser Met Glu Ala Glu Asp
    450                 455                 460 gct gcc act tat tac tgc caa cag tgg agt agt aac ccg ctc acg ttc    1497
Ala Ala Thr Tyr Tyr Cys Gln Gln Trp Ser Ser Asn Pro Leu Thr Phe
465                 470                 475                 480 gga gct ggg acc aag ctg gag ctg aaa cat cat cac cat cat cat tag    1545
Gly Ala Gly Thr Lys Leu Glu Leu Lys His His His His His His
                485                 490                 495

<210> SEQ ID NO 18
<211> LENGTH: 495
<212> TYPE: PRT
<213> ORGANISM: Mus sp.

<400> SEQUENCE: 18

Asp Ile Val Leu Thr Gln Ser Pro Ala Ser Leu Ser Ala Ser Val Gly
 1               5                  10                  15

Glu Thr Val Thr Ile Thr Cys Arg Ala Ser Glu Asn Ile Tyr Ser Tyr
                20                  25                  30

Leu Ala Trp Tyr Gln Gln Lys Gln Gly Lys Ser Pro Gln Leu Leu Val
            35                  40                  45

Tyr Asn Ala Lys Thr Leu Thr Glu Gly Val Pro Ser Arg Phe Ser Gly
        50                  55                  60

Ser Gly Ser Gly Thr Gln Phe Ser Leu Lys Ile Asn Ser Leu Gln Pro
65                  70                  75                  80

Glu Asp Phe Gly Asn Tyr Phe Cys Gln His His Tyr Asp Thr Pro Arg
                85                  90                  95

Thr Phe Gly Gly Gly Thr Lys Leu Glu Ile Lys Gly Gly Gly Gly Ser
            100                 105                 110

Gly Gly Gly Gly Ser Gly Gly Gly Ser Gln Val Gln Leu Gln Gln
        115                 120                 125

Pro Gly Ala Gly Arg Val Arg Pro Gly Ala Ser Val Lys Leu Ser Cys
    130                 135                 140

Lys Ala Ser Gly Tyr Ser Phe Thr Ser Tyr Trp Met Asn Trp Val Lys
145                 150                 155                 160

Gln Arg Pro Gly Gln Gly Leu Glu Trp Ile Gly Met Ile His Pro Ser
                165                 170                 175

Asp Ser Glu Thr Arg Leu Asn Gln Lys Phe Asn Asp Arg Ala Thr Leu
            180                 185                 190

Thr Val Asp Lys Tyr Ser Ser Thr Ala Tyr Ile Gln Leu Ser Ser Pro
        195                 200                 205

Thr Ser Glu Asp Ser Ala Val Tyr Tyr Cys Ala Arg Gly Glu Tyr Tyr
    210                 215                 220

Tyr Gly Ile Phe Asp Tyr Trp Gly Gln Gly Thr Thr Val Thr Val Ser
225                 230                 235                 240

Ser Gly Gly Gly Gly Ser Asp Ile Lys Leu Gln Gln Ser Gly Ala Glu
                245                 250                 255

Leu Ala Arg Pro Gly Ala Ser Val Lys Met Ser Cys Lys Thr Ser Gly
            260                 265                 270
```

Tyr Thr Phe Thr Arg Tyr Thr Met His Trp Val Lys Gln Arg Pro Gly
            275                 280                 285

Gln Gly Leu Glu Trp Ile Gly Tyr Ile Asn Pro Ser Arg Gly Tyr Thr
        290                 295                 300

Asn Tyr Asn Gln Lys Phe Lys Asp Lys Ala Thr Leu Thr Thr Asp Lys
305                 310                 315                 320

Ser Ser Ser Thr Ala Tyr Met Gln Leu Ser Ser Leu Thr Ser Glu Asp
                325                 330                 335

Ser Ala Val Tyr Tyr Cys Ala Arg Tyr Tyr Asp Asp His Tyr Cys Leu
            340                 345                 350

Asp Tyr Trp Arg Gln Gly Thr Thr Leu Thr Val Ser Ser Val Glu Gly
            355                 360                 365

Gly Ser Gly Gly Ser Gly Gly Ser Gly Gly Ser Gly Gly Val Asp Asp
        370                 375                 380

Ile Gln Leu Thr Gln Ser Pro Ala Ile Met Ser Ala Ser Pro Gly Glu
385                 390                 395                 400

Lys Val Thr Met Thr Cys Arg Ala Ser Ser Ser Val Ser Tyr Met Asn
                405                 410                 415

Trp Tyr Gln Gln Lys Ser Gly Thr Ser Pro Lys Arg Trp Ile Tyr Asp
            420                 425                 430

Thr Ser Lys Val Ala Ser Gly Val Pro Tyr Arg Phe Ser Gly Ser Gly
        435                 440                 445

Ser Gly Thr Ser Tyr Ser Leu Thr Ile Ser Ser Met Glu Ala Glu Asp
        450                 455                 460

Ala Ala Thr Tyr Tyr Cys Gln Gln Trp Ser Ser Asn Pro Leu Thr Phe
465                 470                 475                 480

Gly Ala Gly Thr Lys Leu Glu Leu Lys His His His His His
                485                 490                 495

<210> SEQ ID NO 19
<211> LENGTH: 24
<212> TYPE: DNA
<213> ORGANISM: Mus sp.

<400> SEQUENCE: 19
aaaggcctcc ccatattcct cgga                                         24

<210> SEQ ID NO 20
<211> LENGTH: 37
<212> TYPE: DNA
<213> ORGANISM: Mus sp.

<400> SEQUENCE: 20
aaagtcgact ccggacatct ccaaagagtt gatgtac                           37

<210> SEQ ID NO 21
<211> LENGTH: 25
<212> TYPE: DNA
<213> ORGANISM: Mus sp.

<400> SEQUENCE: 21
aatccggagg cggcagcctg gccgc                                        25

<210> SEQ ID NO 22
<211> LENGTH: 46
<212> TYPE: DNA
<213> ORGANISM: Mus sp.

-continued

<400> SEQUENCE: 22
gggaagctta gtgatggtga tggtgatgct tcaggtcctc gcgcgg    46

<210> SEQ ID NO 23
<211> LENGTH: 1245
<212> TYPE: DNA
<213> ORGANISM: Mus sp.
<220> FEATURE:
<221> NAME/KEY: CDS
<222> LOCATION: (1)..(1245)

<400> SEQUENCE: 23

| | | | | | | | | | | | | | | | | |
|---|---|---|---|---|---|---|---|---|---|---|---|---|---|---|---|---|
| tcc | cca | tat | tcc | tcg | gac | acc | aca | ccc | tgc | tgc | ttt | gcc | tac | att | gcc | 48 |
| Ser | Pro | Tyr | Ser | Ser | Asp | Thr | Thr | Pro | Cys | Cys | Phe | Ala | Tyr | Ile | Ala | |
| 1 | | | | 5 | | | | | 10 | | | | | 15 | | |
| cgc | cca | ctg | ccc | cgt | gcc | cac | atc | aag | gag | tat | ttc | tac | acc | agt | ggc | 96 |
| Arg | Pro | Leu | Pro | Arg | Ala | His | Ile | Lys | Glu | Tyr | Phe | Tyr | Thr | Ser | Gly | |
| | | | 20 | | | | | 25 | | | | | 30 | | | |
| aag | tgc | tcc | aac | cca | gca | gtc | gtc | ttt | gtc | acc | cga | aag | aac | cgc | caa | 144 |
| Lys | Cys | Ser | Asn | Pro | Ala | Val | Val | Phe | Val | Thr | Arg | Lys | Asn | Arg | Gln | |
| | | 35 | | | | | 40 | | | | | 45 | | | | |
| gtg | tgt | gcc | aac | cca | gag | aag | aaa | tgg | gtt | cgg | gag | tac | atc | aac | tct | 192 |
| Val | Cys | Ala | Asn | Pro | Glu | Lys | Lys | Trp | Val | Arg | Glu | Tyr | Ile | Asn | Ser | |
| | 50 | | | | | 55 | | | | | 60 | | | | | |
| ttg | gag | atg | tcc | gga | ggc | ggc | agc | ctg | gcc | gcg | ctg | acc | gcg | cac | cag | 240 |
| Leu | Glu | Met | Ser | Gly | Gly | Gly | Ser | Leu | Ala | Ala | Leu | Thr | Ala | His | Gln | |
| 65 | | | | | 70 | | | | | 75 | | | | | 80 | |
| gct | tgc | cac | ctg | ccg | ctg | gag | act | ttc | acc | cgt | cat | cgc | cag | ccg | cgc | 288 |
| Ala | Cys | His | Leu | Pro | Leu | Glu | Thr | Phe | Thr | Arg | His | Arg | Gln | Pro | Arg | |
| | | | | 85 | | | | | 90 | | | | | 95 | | |
| ggc | tgg | gaa | caa | ctg | gag | cag | tgc | ggc | tat | ccg | gtc | cag | cgg | ctg | gtc | 336 |
| Gly | Trp | Glu | Gln | Leu | Glu | Gln | Cys | Gly | Tyr | Pro | Val | Gln | Arg | Leu | Val | |
| | | | 100 | | | | | 105 | | | | | 110 | | | |
| gcc | ctc | tac | ctg | gcg | gcg | cgg | ctg | tcg | tgg | aac | cag | gtc | gac | cag | gtg | 384 |
| Ala | Leu | Tyr | Leu | Ala | Ala | Arg | Leu | Ser | Trp | Asn | Gln | Val | Asp | Gln | Val | |
| | | | 115 | | | | | 120 | | | | | 125 | | | |
| atc | cgc | aac | gcc | ctg | gcc | agc | ccc | ggc | agc | ggc | ggc | gac | ctg | ggc | gaa | 432 |
| Ile | Arg | Asn | Ala | Leu | Ala | Ser | Pro | Gly | Ser | Gly | Gly | Asp | Leu | Gly | Glu | |
| | 130 | | | | | 135 | | | | | 140 | | | | | |
| gcg | atc | cgc | gag | cag | ccg | gag | cag | gcc | cgt | ctg | gcc | ctg | acc | ctg | gcc | 480 |
| Ala | Ile | Arg | Glu | Gln | Pro | Glu | Gln | Ala | Arg | Leu | Ala | Leu | Thr | Leu | Ala | |
| 145 | | | | | 150 | | | | | 155 | | | | | 160 | |
| gcc | gcc | gag | agc | gag | cgc | ttc | gtc | cgg | cag | ggc | acc | ggc | aac | gac | gag | 528 |
| Ala | Ala | Glu | Ser | Glu | Arg | Phe | Val | Arg | Gln | Gly | Thr | Gly | Asn | Asp | Glu | |
| | | | | 165 | | | | | 170 | | | | | 175 | | |
| gcc | ggc | gcg | gcc | aac | ggc | ccg | gcg | gac | agc | ggc | gac | gcc | ctg | ctg | gag | 576 |
| Ala | Gly | Ala | Ala | Asn | Gly | Pro | Ala | Asp | Ser | Gly | Asp | Ala | Leu | Leu | Glu | |
| | | | 180 | | | | | 185 | | | | | 190 | | | |
| cgc | aac | tat | ccc | act | ggc | gcg | gag | ttc | ctc | ggc | gac | ggc | ggc | gac | gtc | 624 |
| Arg | Asn | Tyr | Pro | Thr | Gly | Ala | Glu | Phe | Leu | Gly | Asp | Gly | Gly | Asp | Val | |
| | | | 195 | | | | | 200 | | | | | 205 | | | |
| agc | ttc | agc | acc | cgc | ggc | acg | cag | aac | tgg | acg | gtg | gag | cgg | ctg | ctc | 672 |
| Ser | Phe | Ser | Thr | Arg | Gly | Thr | Gln | Asn | Trp | Thr | Val | Glu | Arg | Leu | Leu | |
| | | 210 | | | | | 215 | | | | | 220 | | | | |
| cag | gcg | cac | cgc | caa | ctg | gag | gag | cgc | ggc | tat | gtg | ttc | gtc | ggc | tac | 720 |
| Gln | Ala | His | Arg | Gln | Leu | Glu | Glu | Arg | Gly | Tyr | Val | Phe | Val | Gly | Tyr | |
| 225 | | | | | 230 | | | | | 235 | | | | | 240 | |
| cac | ggc | acc | ttc | ctc | gaa | gcg | gcg | caa | agc | atc | gtc | ttc | ggc | ggg | gtg | 768 |
| His | Gly | Thr | Phe | Leu | Glu | Ala | Ala | Gln | Ser | Ile | Val | Phe | Gly | Gly | Val | |
| | | | | 245 | | | | | 250 | | | | | 255 | | |

```
cgc gcg cgc agc cag gac ctc gac gcg atc tgg cgc ggt ttc tat atc      816
Arg Ala Arg Ser Gln Asp Leu Asp Ala Ile Trp Arg Gly Phe Tyr Ile
        260                 265                 270 gcc ggc gat ccg gcg ctg gcc tac ggc tac gcc cag gac cag gaa ccc      864
Ala Gly Asp Pro Ala Leu Ala Tyr Gly Tyr Ala Gln Asp Gln Glu Pro
            275                 280                 285 gac gca cgc ggc cgg atc cgc aac ggt gcc ctg ctg cgg gtc tat gtg      912
Asp Ala Arg Gly Arg Ile Arg Asn Gly Ala Leu Leu Arg Val Tyr Val
290                 295                 300 ccg cgc tcg agc ctg ccg ggc ttc tac cgc acc agc ctg acc ctg gcc      960
Pro Arg Ser Ser Leu Pro Gly Phe Tyr Arg Thr Ser Leu Thr Leu Ala
305                 310                 315                 320 gcg ccg gag gcg gcg ggc gag gtc gaa cgg ctg atc ggc cat ccg ctg     1008
Ala Pro Glu Ala Ala Gly Glu Val Glu Arg Leu Ile Gly His Pro Leu
                325                 330                 335 ccg ctg cgc ctg gac gcc atc acc ggc ccc gag gag gaa ggc ggg cgc     1056
Pro Leu Arg Leu Asp Ala Ile Thr Gly Pro Glu Glu Glu Gly Gly Arg
            340                 345                 350 ctg gag acc att ctc ggc tgg ccg ctg gcc gag cgc acc gtg gtg att     1104
Leu Glu Thr Ile Leu Gly Trp Pro Leu Ala Glu Arg Thr Val Val Ile
        355                 360                 365 ccc tcg gcg atc ccc acc gac ccg cgc aac gtc ggc ggc gac ctc gac     1152
Pro Ser Ala Ile Pro Thr Asp Pro Arg Asn Val Gly Gly Asp Leu Asp
370                 375                 380 ccg tcc agc atc ccc gac aag gaa cag gcg atc agc gcc ctg ccg gac     1200
Pro Ser Ser Ile Pro Asp Lys Glu Gln Ala Ile Ser Ala Leu Pro Asp
385                 390                 395                 400 tac gcc agc cag ccc ggc aaa ccg ccg cgc gag gac ctg aag taa          1245
Tyr Ala Ser Gln Pro Gly Lys Pro Pro Arg Glu Asp Leu Lys
                405                 410                 415

<210> SEQ ID NO 24
<211> LENGTH: 414
<212> TYPE: PRT
<213> ORGANISM: Mus sp.

<400> SEQUENCE: 24

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Met Ser Gly Gly Ser Leu Ala Ala Leu Thr Ala His Gln
65                  70                  75                  80

Ala Cys His Leu Pro Leu Glu Thr Phe Thr Arg His Arg Gln Pro Arg
                85                  90                  95

Gly Trp Glu Gln Leu Glu Gln Cys Gly Tyr Pro Val Gln Arg Leu Val
            100                 105                 110

Ala Leu Tyr Leu Ala Ala Arg Leu Ser Trp Asn Gln Val Asp Gln Val
        115                 120                 125

Ile Arg Asn Ala Leu Ala Ser Pro Gly Ser Gly Gly Asp Leu Gly Glu
    130                 135                 140

Ala Ile Arg Glu Gln Pro Glu Gln Ala Arg Leu Ala Leu Thr Leu Ala
145                 150                 155                 160

Ala Ala Glu Ser Glu Arg Phe Val Arg Gln Gly Thr Gly Asn Asp Glu
```

```
                      165                 170                 175
        Ala Gly Ala Ala Asn Gly Pro Ala Asp Ser Gly Asp Ala Leu Leu Glu
                        180                 185                 190

Arg Asn Tyr Pro Thr Gly Ala Glu Phe Leu Gly Asp Gly Asp Val
                    195                 200                 205

Ser Phe Ser Thr Arg Gly Thr Gln Asn Trp Thr Val Glu Arg Leu Leu
            210                 215                 220

Gln Ala His Arg Gln Leu Glu Glu Arg Gly Tyr Val Phe Val Gly Tyr
        225                 230                 235                 240

His Gly Thr Phe Leu Glu Ala Ala Gln Ser Ile Val Phe Gly Gly Val
                        245                 250                 255

Arg Ala Arg Ser Gln Asp Leu Asp Ala Ile Trp Arg Gly Phe Tyr Ile
                    260                 265                 270

Ala Gly Asp Pro Ala Leu Ala Tyr Gly Tyr Ala Gln Asp Gln Glu Pro
                275                 280                 285

Asp Ala Arg Gly Arg Ile Arg Asn Gly Ala Leu Leu Arg Val Tyr Val
            290                 295                 300

Pro Arg Ser Ser Leu Pro Gly Phe Tyr Arg Thr Ser Leu Thr Leu Ala
        305                 310                 315                 320

Ala Pro Glu Ala Ala Gly Glu Val Glu Arg Leu Ile Gly His Pro Leu
                        325                 330                 335

Pro Leu Arg Leu Asp Ala Ile Thr Gly Pro Glu Glu Gly Gly Arg
                    340                 345                 350

Leu Glu Thr Ile Leu Gly Trp Pro Leu Ala Glu Arg Thr Val Val Ile
                355                 360                 365

Pro Ser Ala Ile Pro Thr Asp Pro Arg Asn Val Gly Gly Asp Leu Asp
            370                 375                 380

Pro Ser Ser Ile Pro Asp Lys Glu Gln Ala Ile Ser Ala Leu Pro Asp
        385                 390                 395                 400

Tyr Ala Ser Gln Pro Gly Lys Pro Pro Arg Glu Asp Leu Lys
                        405                 410

<210> SEQ ID NO 25
<211> LENGTH: 363
<212> TYPE: DNA
<213> ORGANISM: Mus sp.
<220> FEATURE:
<221> NAME/KEY: CDS
<222> LOCATION: (1)..(363)

<400> SEQUENCE: 25 gat atc aaa ctg cag cag tca ggg gct gaa ctg gca aga cct ggg gcc      48
Asp Ile Lys Leu Gln Gln Ser Gly Ala Glu Leu Ala Arg Pro Gly Ala
  1               5                  10                  15 tca gtg aag atg tcc tgc aag act tct ggc tac acc ttt act agg tac      96
Ser Val Lys Met Ser Cys Lys Thr Ser Gly Tyr Thr Phe Thr Arg Tyr
                 20                  25                  30 acg atg cac tgg gta aaa cag agg cct gga cag ggt ctg gaa tgg att     144
Thr Met His Trp Val Lys Gln Arg Pro Gly Gln Gly Leu Glu Trp Ile
             35                  40                  45 gga tac att aat cct agc cgt ggt tat act aat tac aat cag aag ttc     192
Gly Tyr Ile Asn Pro Ser Arg Gly Tyr Thr Asn Tyr Asn Gln Lys Phe
         50                  55                  60 aag gac aag gcc aca ttg act aca gac aaa tcc tcc agc aca gcc tac     240
Lys Asp Lys Ala Thr Leu Thr Thr Asp Lys Ser Ser Ser Thr Ala Tyr
 65                  70                  75                  80 atg caa ctg agc agc ctg aca tct gag gac tct gca gtc tat tac tgt     288
```

```
Met Gln Leu Ser Ser Leu Thr Ser Glu Asp Ser Ala Val Tyr Tyr Cys
                85                  90                  95 gca aga tat tat gat gat cat tac tgc ctt gac tac tgg cgc caa ggc        336
Ala Arg Tyr Tyr Asp Asp His Tyr Cys Leu Asp Tyr Trp Arg Gln Gly
            100                 105                 110 acc act ctc aca gtc tcc tca gtc gaa                                    363
Thr Thr Leu Thr Val Ser Ser Val Glu
        115                 120

<210> SEQ ID NO 26
<211> LENGTH: 121
<212> TYPE: PRT
<213> ORGANISM: Mus sp.

<400> SEQUENCE: 26

Asp Ile Lys Leu Gln Gln Ser Gly Ala Glu Leu Ala Arg Pro Gly Ala
 1               5                  10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Arg Gln Gly
            100                 105                 110

Thr Thr Leu Thr Val Ser Ser Val Glu
        115                 120

<210> SEQ ID NO 27
<211> LENGTH: 324
<212> TYPE: DNA
<213> ORGANISM: Mus sp.
<220> FEATURE:
<221> NAME/KEY: CDS
<222> LOCATION: (1)..(324)

<400> SEQUENCE: 27 gtc gac gac att cag ctg acc cag tct cca gca atc atg tct gca tct         48
Val Asp Asp Ile Gln Leu Thr Gln Ser Pro Ala Ile Met Ser Ala Ser
 1               5                  10                  15 cca ggg gag aag gtc acc atg acc tgc aga gcc agt tca agt gta agt         96
Pro Gly Glu Lys Val Thr Met Thr Cys Arg Ala Ser Ser Ser Val Ser
            20                  25                  30 tac atg aac tgg tac cag cag aag tca ggc acc tcc ccc aaa aga tgg        144
Tyr Met Asn Trp Tyr Gln Gln Lys Ser Gly Thr Ser Pro Lys Arg Trp
        35                  40                  45 att tat gac aca tcc aaa gtg gct tct gga gtc cct tat cgc ttc agt        192
Ile Tyr Asp Thr Ser Lys Val Ala Ser Gly Val Pro Tyr Arg Phe Ser
    50                  55                  60 ggc agt ggg tct ggg acc tca tac tct ctc aca atc agc agc atg gag        240
Gly Ser Gly Ser Gly Thr Ser Tyr Ser Leu Thr Ile Ser Ser Met Glu
65                  70                  75                  80 gct gaa gat gct gcc act tat tac tgc caa cag tgg agt agt aac ccg        288
Ala Glu Asp Ala Ala Thr Tyr Tyr Cys Gln Gln Trp Ser Ser Asn Pro
                85                  90                  95 ctc acg ttc gga gct ggg acc aag ctg gag ctg aaa                        324
Leu Thr Phe Gly Ala Gly Thr Lys Leu Glu Leu Lys
```

Leu Thr Phe Gly Ala Gly Thr Lys Leu Glu Leu Lys
            100                 105

<210> SEQ ID NO 28
<211> LENGTH: 108
<212> TYPE: PRT
<213> ORGANISM: Mus sp.

<400> SEQUENCE: 28

Val Asp Asp Ile Gln Leu Thr Gln Ser Pro Ala Ile Met Ser Ala Ser
1               5                   10                  15

Pro Gly Glu Lys Val Thr Met Thr Cys Arg Ala Ser Ser Ser Val Ser
            20                  25                  30

Tyr Met Asn Trp Tyr Gln Gln Lys Ser Gly Thr Ser Pro Lys Arg Trp
        35                  40                  45

Ile Tyr Asp Thr Ser Lys Val Ala Ser Gly Val Pro Tyr Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Asn Pro
                85                  90                  95

Leu Thr Phe Gly Ala Gly Thr Lys Leu Glu Leu Lys
            100                 105

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: peptide

<400> SEQUENCE: 29

Arg Ala Ser Glu Asn Ile Tyr Ser Tyr Leu Ala
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: peptide

<400> SEQUENCE: 30

Asn Ala Lys Thr Leu Thr Glu
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: peptide

<400> SEQUENCE: 31

Gln His His Tyr Asp Thr Pro Arg Thr
1               5

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: peptide

```
-continued

<400> SEQUENCE: 32

Tyr Trp Met Asn
  1

<210> SEQ ID NO 33
<211> LENGTH: 19
<212> TYPE: PRT
<213> ORGANISM: Artificial Sequence
<220> FEATURE:
<223> OTHER INFORMATION: Description of Artificial Sequence: peptide

<400> SEQUENCE: 33

Gly Met Ile His Pro Ser Asp Ser Glu Thr Arg Leu Asn Gln Lys Phe
  1               5                  10                  15

Asn Asp Arg

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: peptide

<400> SEQUENCE: 34

Gly Glu Tyr Tyr Tyr Gly Ile Phe Asp Tyr
  1               5                  10
```